(12) United States Patent
Agresta

(10) Patent No.: US 10,105,369 B2
(45) Date of Patent: *Oct. 23, 2018

(54) THERAPEUTICALLY ACTIVE COMPOUNDS AND THEIR METHODS OF USE

(71) Applicant: Agios Pharmaceuticals, Inc., Cambridge, MA (US)

(72) Inventor: Samuel V. Agresta, Lexington, MA (US)

(73) Assignee: Agios Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/864,994

(22) Filed: Jan. 8, 2018

(65) Prior Publication Data

US 2018/0125850 A1 May 10, 2018

Related U.S. Application Data

(63) Continuation of application No. 15/612,984, filed on Jun. 2, 2017, now Pat. No. 9,889,137, which is a continuation of application No. 14/868,283, filed on Sep. 28, 2015, now Pat. No. 9,694,013.

(60) Provisional application No. 62/056,996, filed on Sep. 29, 2014.

(51) Int. Cl.
*A61K 31/53* (2006.01)
*A61K 9/00* (2006.01)
*A61K 31/185* (2006.01)

(52) U.S. Cl.
CPC ............ *A61K 31/53* (2013.01); *A61K 9/0053* (2013.01); *A61K 31/185* (2013.01)

(58) Field of Classification Search
CPC ..... A61K 31/53; A61K 9/0053; A61K 31/185
USPC ....................................................... 514/245
See application file for complete search history.

(56) References Cited

U.S. PATENT DOCUMENTS

| | | | |
|---|---|---|---|
| 9,512,107 B2 | 12/2016 | Cianchetta et al. | |
| 9,579,324 B2 | 2/2017 | Konteatis et al. | |
| 9,656,999 B2 | 5/2017 | Cianchetta et al. | |
| 9,694,013 B2 | 7/2017 | Agresta | |
| 9,724,350 B2 | 8/2017 | Travins et al. | |
| 9,732,062 B2 | 8/2017 | Cianchetta et al. | |
| 9,738,625 B2 | 8/2017 | Agresta et al. | |
| 9,751,863 B2 | 9/2017 | Zhang | |
| 2016/0194305 A1* | 7/2016 | Agresta ............... | A61K 31/444 514/245 |
| 2017/0157132 A1 | 6/2017 | Wu et al. | |
| 2017/0246174 A1 | 8/2017 | Amatangelo et al. | |
| 2017/0266193 A1 | 9/2017 | Agresta | |
| 2017/0298045 A1 | 10/2017 | Cianchetta et al. | |
| 2017/0305885 A1 | 10/2017 | Agresta et al. | |

FOREIGN PATENT DOCUMENTS

| | | |
|---|---|---|
| WO | 2013102431 A1 | 7/2013 |
| WO | 2016126798 A1 | 8/2016 |
| WO | 2017066599 A1 | 4/2017 |

OTHER PUBLICATIONS

Balss et al. "Analysis of the IDH1 codon 132 mutation in brain tumors" Acta Neuropathol 116:597-602 (2008).
Dang et al. "Cancer-associated IDH1 mutations produce 2-hydroxyglutarate," Nature, 462:739-744 (2009).
Final office action for U.S. Appl. No. 13/735,467 dated Dec. 3, 2015 (15 pages).
Final office action for U.S. Appl. No. 14/904,032 dated Dec. 15, 2016 (32 pages).
Gerhard et al., Genome Res. 14:2121 2127(2004).
International Search Report for PCT/US2015/052598 dated Jan. 13, 2016 (5 pages).
Non final office action for U.S. Appl. No. 13/735,467 dated May 22, 2015 (17 pages).
Non final office action for U.S. Appl. No. 14/904,032 dated Jun. 14, 2016 (31 pages).
Non final office action for U.S. Appl. No. 14/909,451 dated Aug. 8, 2016 (9 pages).
Non final office action for U.S. Appl. No. 14/868,283 dated Oct. 27, 2016 (9 pages).
Non final office action for U.S. Appl. No. 15/229,011 dated Dec. 29, 2016 (24 pages).
Notice of Allowance for U.S. Appl. No. 15/173,519 dated Aug. 10, 2016 (10 pages).
Notice of Allowance for U.S. Appl. No. 15/173,519 dated Sep. 29, 2016 (10 pages).
Advisory Action Before the Filing of an Appeal Brief for U.S. Appl. No. 13/735,467 dated Mar. 22, 2016 (3 pages).
Yan et al., "IDH1 and IDH2 Mutations in Gliomas," N Engl. J. Med 360;8, 765-773 (2009).
Agios Pharmaceuticals, "New Agios Clinical Data form Ongoing Phase 1 Trial of AG-221 Continue to Show Complete and Durable Remissions in Patients with Difficult to Treat Hematologic Malignancies," [online], [retrieved on Oct. 26, 2016] Retrieved from Internet, URL:http://investor.agios.com/phoenix.zhtml?c=251862&p=irol-newsArticle_Print&ID=1939863.
Enasidenib (AG-221) [online], [retrieved on Oct. 26, 2016] Retrieved from Internet, URL:http://newdrugapprovals.org/2016/04/20/3nasidenib-ag-221/.
Advisory Action for U.S. Appl. No. 13/735,467, dated Jun. 10, 2016 (3 pages).
Notice of Allowance for U.S. Appl. No. 13/735,467, dated Jan. 27, 2017 (9 pages).
Notice of Allowance for U.S. Appl. No. 13/735,467, dated Mar. 31, 2017 (10 pages).
Notice of Allowance for U.S. Appl. No. 15/337,683, dated Jan. 17, 2017 (7 pages).
Notice of Allowance for U.S. Appl. No. 14/904,032, dated Mar. 17, 2017 (5 pages).

(Continued)

*Primary Examiner* — Kristin A Vajda
(74) *Attorney, Agent, or Firm* — Jones Day

(57) ABSTRACT

Provided are compounds useful for treating cancer and methods of treating cancer, for example an advanced solid tumor, such as a glioma, or angioimmunoblastic T-cell lymphoma (AITL).

24 Claims, 23 Drawing Sheets

(56) References Cited

OTHER PUBLICATIONS

Final Office Action for U.S. Appl. No. 14/909,451, dated Feb. 8, 2017 (12 pages).
Notice of Allowance for U.S. Appl. No. 14/909,451, dated Apr. 14, 2017 (5 pages).
Notice of Allowance for U.S. Appl. No. 15/229,011, dated May 4, 2017 (5 pages).
Notice of Allowance for U.S. Appl. No. 14/868,283, dated Feb. 27, 2017 (8 pages).
Office Action for U.S. Appl. No. 15/612,984, dated Jun. 21, 2017 (8 pages).
Notice of Allowance for U.S. Appl. No. 15/612,984, dated Oct. 5, 2017 (8 pages).

\* cited by examiner

THERAPEUTICALLY ACTIVE COMPOUNDS AND THEIR METHODS OF USE

RELATED APPLICATIONS

This application is a continuation of U.S. application Ser. No. 15/612,984, filed Jun. 2, 2017, which is a continuation of U.S. application Ser. No. 14/868,283, filed Sep. 28, 2015, now U.S. Pat. No. 9,694,013, which claims priority to U.S. provisional application Ser. No. 62/056,996, filed Sep. 29, 2014, each of which is incorporated herein by reference in its entirety.

FIELD

Provided herein are methods of treatment of cancers characterized by the presence of a mutant allele of IDH2 comprising administering to a cancer patient an IDH2 inhibitor.

BACKGROUND

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH2 (isocitrate dehydrogenase 2 (NADP+), mitochondrial) is also known as IDH; IDP; IDHM; IDPM; ICD-M; or mNADP-IDH. The protein encoded by this gene is the NADP(+)-dependent isocitrate dehydrogenase found in the mitochondria. It plays a role in intermediary metabolism and energy production. This protein may tightly associate or interact with the pyruvate dehydrogenase complex. Human IDH2 gene encodes a protein of 452 amino acids. The nucleotide and amino acid sequences for IDH2 can be found as GenBank entries NM_002168.2 and NP_002159.2 respectively. The nucleotide and amino acid sequence for human IDH2 are also described in, e.g., Huh et al., Submitted (November-1992) to the EMBL/GenBank/DDBJ databases; and The MGC Project Team, Genome Res. 14:2121-2127 (2004).

Non-mutant, e.g., wild type, IDH2 catalyzes the oxidative decarboxylation of isocitrate to α-ketoglutarate (α-KG) thereby reducing NAD$^+$ (NADP$^+$) to NADH (NADPH), e.g., in the forward reaction:

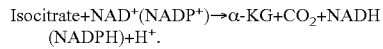

Isocitrate+NAD$^+$(NADP$^+$)→α-KG+CO$_2$+NADH (NADPH)+H$^+$.

It has been discovered that mutations of IDH2 present in certain cancer cells result in a new ability of the enzyme to catalyze the NAPH-dependent reduction of α-ketoglutarate to R(−)-2-hydroxyglutarate (2-HG). 2-HG is not formed by wild-type IDH2. The production of 2-HG is believed to contribute to the formation and progression of cancer (Dang, L et al, Nature 2009, 462:739-44).

The inhibition of mutant IDH2 and its neoactivity is therefore a potential therapeutic treatment for cancer. Accordingly, there is an ongoing need for inhibitors of IDH2 mutants having alpha hydroxyl neoactivity.

PCT Publication No. WO 2013/102431 and US Publication No. US 2013/0190287 hereby incorporated by reference in their entirety, disclose compounds that inhibit IDH2 mutants (e.g., IDH2R140Q and IDH2R172K). These applications additionally disclose methods for the preparation of inhibitors of mutant IDH2, pharmaceutical compositions containing these compounds, and methods for the therapy of diseases, disorders, or conditions (e.g., cancer) associated with over expression and/or amplification of mutant IDH2.

SUMMARY

Disclosed herein are methods of treating subjects with advanced solid tumors, including glioma, melanoma, chondrosarcoma, or cholangiocarcinoma, and angioimmunoblastic T-cell lymphoma (AITL), each characterized by the presence of a mutant allele of IDH2.

DETAILED DESCRIPTION

Figure 1:
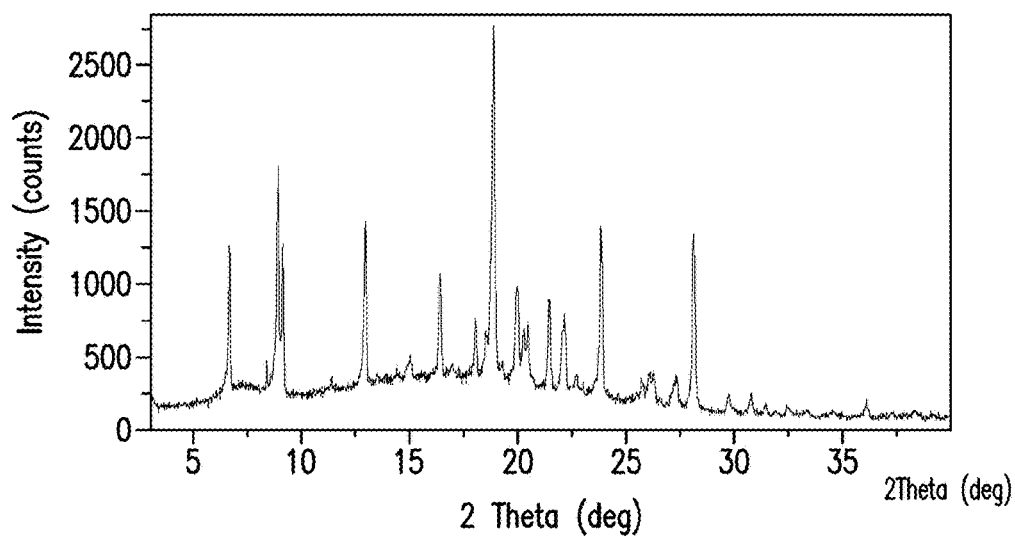
FIG. 1 is an X-ray powder diffractogram (XRPD) of compound 1 Form 1.

The details of construction and the arrangement of components set forth in the following description or illustrated in the drawings are not meant to be limiting. Other embodiments and different ways to practice the invention are expressly included. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Definitions

As used above, and throughout the description of the invention, the following terms, unless otherwise indicated, shall be understood to have the following meanings.

As used herein, the term "elevated levels of 2-HG" means 10%, 20% 30%, 50%, 75%, 100%, 200%, 500% or more 2-HG then is present in a subject that does not carry a mutant IDH allele (e.g., a mutant IDH2 allele). The term "elevated levels of 2-HG" may refer to the amount of 2-HG within a cell, within a tumor, within an organ comprising a tumor, or within a bodily fluid.

The term "bodily fluid" includes one or more of amniotic fluid surrounding a fetus, aqueous humour, blood (e.g., blood plasma), serum, Cerebrospinal fluid, cerumen, chyme, Cowper's fluid, female ejaculate, interstitial fluid, lymph, breast milk, mucus (e.g., nasal drainage or phlegm), pleural fluid, pus, saliva, sebum, semen, serum, sweat, tears, urine, vaginal secretion, or vomit.

As used herein, the terms "inhibit" or "prevent" include both complete and partial inhibition and prevention. An inhibitor may completely or partially inhibit the intended target.

The term an "mutant IDH2 inhibitor" or "inhibitor of IDH2 mutant(s)" means a molecule e.g., a polypeptide, peptide, or small molecule (e.g., a molecule of less than 1,000 daltons), or aptomer, that binds to an IDH2 mutant subunit and inhibits neoactivity, e.g., by inhibiting formation of a dimer, e.g., a homodimer of mutant IDH2 subunits or a heterodimer of a mutant and a wildype subunit. In some embodiments, the neoactivity inhibition is at least about 60%, 70%, 80%, 90%, 95% or 99%.

The term "treat" means decrease, suppress, attenuate, diminish, arrest, or stabilize the development or progression of a disease/disorder (e.g., an advanced solid tumor such as glioma, melanoma, chondrosarcoma, or cholangiocarcinoma, or AITL, each characterized by the presence of a mutant allele of IDH2), lessen the severity of the disease/disorder or improve the symptoms associated with the disease/disorder.

As used herein, an amount of a compound, including a crystalline form thereof, effective to treat a disorder, or a "therapeutically effective amount" or "therapeutically effective dose" refers to an amount of the compound, or a pharmaceutically acceptable salt thereof, including a crystalline form thereof, which is effective, upon single or multiple dose administration to a subject, in treating a cell, or in curing, alleviating, relieving or improving a subject with a disorder beyond that expected in the absence of such treatment.

As used herein, the term "subject" is intended to mean human. Exemplary human subjects include a human patient (referred to as a patient) having a disorder, e.g., a disorder described herein or a normal subject.

As used Herein, the term "free-base equivalent" or "free-base equivalent strength" is the amount of a salt form of a first compound that is required to achieve the equivalent amount of the non-salt, or free-base, of that same compound. Because a salt of a compound can weigh more than the non-salt version of that same compound, more of the salt of the compound can be required to achieve the equivalent amount of that same compound in the non-salt (of free-base) form. Compound 2 is a mesylate salt of compound 1 and consequently compound 2 has a larger molecular weight than compound 1. Accordingly if a specified amount of compound 1 is desired and compound 1 is in the form of a salt such as compound 2, the amount (e.g., number of mg) of compound 2 required to achieve the equivalent amount of compound 1 will be larger than the amount of compound 1. For example 30 mg (free-base equivalent strength) would equal 36 mg of compound 2, 50 mg (free-base equivalent strength) would equal 60 mg of compound 2, 75 mg (free-base equivalent strength) would equal 90 mg, 100 mg (free-base equivalent strength) would equal 120 mg, and 125 mg (free-base equivalent strength) would equal 150 mg.

"Form 1" or "compound 1 Form 1" are used interchangeably, and describe Form 1 of compound 1, as synthesized in Example 3A, in the Examples section below, and as described below, and represented by data shown in FIG. 1.

"Form 2" or "compound 1 Form 2" are used interchangeably, and describe Form 2 of compound 1, as synthesized in Example 4A, in the Examples section below, and as described below, and represented by data shown in FIGS. 2, 3, and 4.

"Form 3" or "compound 2 Form 3" are used interchangeably, and describe Form 3 of compound 2, as synthesized in Example 6A, in the Examples section below, and as described below, and represented by data shown in FIGS. 5, 6, 7, and 8.

"Form 4" or "compound 2 Form 4" are used interchangeably, and describe Form 4 of compound 2, as synthesized in Example 7A, in the Examples section below, and as described below, and represented by data shown in FIGS. 9 and 10.

"Form 5" or "compound 2 Form 5" are used interchangeably, and describe Form 5 of compound 2, as synthesized in Example 8A, in the Examples section below, and as described below, and represented by data shown in FIGS. 11 and 12.

"Form 6" or "compound 2 Form 6" are used interchangeably, and describe Form 6 of compound 2, as synthesized in Example 9A, in the Examples section below, and as described below, and represented by data shown in FIGS. 13 and 14.

"Form 7" or "compound 2 Form 7" are used interchangeably, and describe Form 7 of compound 2, as synthesized in Example 10A, in the Examples section below, and as described below, and represented by data shown in FIGS. 15 and 16.

"Form 8" or "compound 2 Form 8" are used interchangeably, and describe Form 8 of compound 2, as synthesized in Example 11A, in the Examples section below, and as described below, and represented by data shown in FIGS. 17 and 18.

"Form 9" or "compound 2 Form 9" are used interchangeably, and describe Form 9 of compound 2, as synthesized in Example 12A, in the Examples section below, and as described below, and represented by data shown in FIGS. 19 and 20.

"Form 10" or "compound 2 Form 10" are used interchangeably, and describe Form 10 of compound 2, as synthesized in Example 13A, in the Examples section below, and as described below, and represented by data shown in FIGS. 21 and 22.

"Form 11" or "compound 2 Form 11" are used interchangeably, and describe Form 11 of compound 2, as synthesized in Example 14A, in the Examples section below, and as described below, and represented by data shown in FIGS. 23, 24, and 25.

"Form 12" or "compound 2 Form 12" are used interchangeably, and describe Form 12 of compound 2, as synthesized in Example 15A, in the Examples section below, and as described below, and represented by data shown in FIGS. 26 and 27.

"Form 13" or "compound 2 Form 13" are used interchangeably, and describe Form 13 of compound 2, as synthesized in Example 16A, in the Examples section below, and as described below, and represented by data shown in FIGS. 28 and 29.

"Form 14" or "compound 2 Form 14" are used interchangeably, and describe Form 14 of compound 2, as synthesized in Example 17A, in the Examples section below, and as described below, and represented by data shown in FIGS. 30 and 31.

"Form 15" or "compound 2 Form 15" are used interchangeably, and describe Form 15 of compound 2, as synthesized in Example 18A, in the Examples section below, and as described below, and represented by data shown in FIGS. 32 and 33.

"Form 16" or "compound 1 Form 16" are used interchangeably, and describe Form 16 of compound 1, as synthesized in Example 2A, in the Examples section below, and as described below, and represented by data shown in FIGS. 34, 35 and 36.

"Form 17" or "compound 1 Form 16" are used interchangeably, and describe Form 16 of compound 1, as synthesized in Example 20A, in the Examples section below, and as described below, and represented by data shown in FIG. 37.

"Form 18" or "compound 1 Form 16" are used interchangeably, and describe Form 16 of compound 1, as synthesized in Example 21A, in the Examples section below, and as described below, and represented by data shown in FIG. 38.

"Form 19" or "compound 1 Form 16" are used interchangeably, and describe Form 16 of compound 1, as synthesized in Example 22A, in the Examples section below, and as described below, and represented by data shown in FIG. 39.

As used herein, "crystalline" refers to a solid having a highly regular chemical structure. In particular, a crystalline compound 1 or compound 2 may be produced as one or more single crystalline forms of the compound 1 or compound 2. For the purposes of this application, the terms "crystalline form", "single crystalline form" and "polymorph" are synonymous; the terms distinguish between crystals that have different properties (e.g., different XRPD patterns and/or different DSC scan results). The term "polymorph" includes pseudopolymorphs, which are typically different solvates of a material, and thus their properties differ from one another. Thus, each distinct polymorph and pseudopolymorph of the compound 1 or compound 2 is considered to be a distinct single crystalline form herein.

"Substantially crystalline" refers to forms that may be at least a particular weight percent crystalline. Particular weight percentages are 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In some embodiments, substantially crystalline refers to a compound 1 or compound 2 that is at least 70% crystalline. In other embodiments, substantially crystalline refers to a compound 1 or compound 2 that is at least 90% crystalline.

As used herein, the terms "isolated" refers to forms that may be at least a particular weight percent of a particular crystalline form of compound 2 or compound 1. Particular weight percentages are 90%, 91%, 92%, 93%, 94%, 95%, 96%, 97%, 98%, 99%, 99.5%, 99.9%, or any percentage between 90% and 100%.

The term "solvate or solvated" means a physical association of a compound, including a crystalline form thereof, of this invention with one or more solvent molecules. This physical association includes hydrogen bonding. In certain instances the solvate will be capable of isolation, for example when one or more solvent molecules are incorporated in the crystal lattice of the crystalline solid. "Solvate or solvated" encompasses both solution-phase and isolable solvates. Representative solvates include, for example, a hydrate, ethanolates or a methanolate.

The term "hydrate" is a solvate wherein the solvent molecule is H$_2$O that is present in a defined stoichiometric amount, and may, for example, include hemihydrate, monohydrate, dihydrate, or trihydrate.

The term "mixture" is used to refer to the combined elements of the mixture regardless of the phase-state of the combination (e.g., liquid or liquid/crystalline).

The term "seeding" is used to refer to the addition of a crystalline material to initiate recrystallization or crystallization.

The term "antisolvent" is used to refer to a solvent in which compounds, including crystalline forms thereof, are poorly soluble.

As used herein, the term "about" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

Pharmaceutical Compositions and Methods of Treatment

Provided is a method of treating an advanced solid tumor, for example, a glioma, melanoma, chondrosarcoma, or cholangiocarcinoma (e.g., glioma), or treating angioimmunoblastic T-cell lymphoma (AITL), each characterized by the presence of a mutant allele of IDH2, comprising administering to subject in need thereof a therapeutically effective amount of a mutant IDH2 inhibitor.

Also provided is a method of treating an advanced solid tumor, for example, a glioma, melanoma, chondrosarcoma, or cholangiocarcinoma (e.g., glioma), or treating angioimmunoblastic T-cell lymphoma (AITL), each characterized by the presence of a mutant allele of IDH2, each characterized by the presence of a mutant allele of IDH2, comprising administering to a subject in need thereof a therapeutically effective amount of 2-Methyl-1-[(4-[6-(trifluoromethyl)pyridin-2-yl]-6-{[2-(trifluoromethyl)pyridin-4-yl]amino}-1,3,5-triazin-2-yl)amino]propan-2-ol, hereinafter characterized as compound 1, or a pharmaceutically acceptable salt thereof.

Also provided is a method of treating an advanced solid tumor, for example, a glioma, melanoma, chondrosarcoma, or cholangiocarcinoma (e.g., glioma), or treating angioimmunoblastic T-cell lymphoma (AITL), each characterized by the presence of a mutant allele of IDH2, comprising administering to subject in need thereof a therapeutically effective amount of 2-Methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate, hereinafter characterized as compound 2.

Also provided is a method of treating an advanced solid tumor, for example, a glioma, melanoma, chondrosarcoma, or cholangiocarcinoma (e.g., glioma), or treating angioimmunoblastic T-cell lymphoma (AITL), each characterized by the presence of a mutant allele of IDH2, comprising administering to subject in need thereof a pharmaceutical composition comprising a therapeutically effective amount of a mutant IDH2 inhibitor, and one or more pharmaceutically acceptable carrier(s).

Also provided is a method of treating an advanced solid tumor, for example, a glioma, melanoma, chondrosarcoma, or cholangiocarcinoma (e.g., glioma), or treating angioimmunoblastic T-cell lymphoma (AITL), each characterized by the presence of a mutant allele of IDH2, comprising administering to subject in need thereof a pharmaceutical composition comprising a therapeutically effective amount of compound 1, or a pharmaceutically acceptable salt thereof, and one or more pharmaceutically acceptable carrier(s).

Also provided is a method of treating an advanced solid tumor, for example, a glioma, melanoma, chondrosarcoma, or cholangiocarcinoma (e.g., glioma), or treating angioimmunoblastic T-cell lymphoma (AITL), each characterized by the presence of a mutant allele of IDH2, comprising administering to subject in need thereof a pharmaceutical composition comprising a therapeutically effective amount of compound 2, and one or more pharmaceutically acceptable carrier(s).

Also provided is a method of treating an advanced solid tumor, for example, a glioma, melanoma, chondrosarcoma, or cholangiocarcinoma (e.g., glioma), or treating angioimmunoblastic T-cell lymphoma (AITL), each characterized by the presence of a mutant allele of IDH2, comprising administering to subject in need thereof a therapeutically effective amount of compound 1, or a crystalline form thereof; or a therapeutically effective dose of compound 2, or a crystalline form thereof.

Also provided is a method of treating an advanced solid tumor, for example, a glioma, melanoma, chondrosarcoma, or cholangiocarcinoma (e.g., glioma), or treating angioimmunoblastic T-cell lymphoma (AITL), each characterized by the presence of a mutant allele of IDH2, comprising administering to subject in need thereof a pharmaceutical composition comprising a therapeutically effective amount of compound 1, or a crystalline form thereof; or a therapeutically effective dose of compound 2, or a crystalline form thereof; and one or more pharmaceutically acceptable carrier(s).

Also provided is a method of treating an advanced solid tumor, for example, a glioma, melanoma, chondrosarcoma, or cholangiocarcinoma (e.g., glioma), or treating angioimmunoblastic T-cell lymphoma (AITL), each characterized by the presence of a mutant allele of IDH2, comprising administering to a subject in need thereof a therapeutically effective dose of a pharmaceutically acceptable salt of compound 1 (e.g., compound 2), wherein the therapeutically effective dose is from about 30 mg to about 300 mg (free-base equivalent strength), once daily or twice daily, e.g., once daily (e.g., about 30 mg to about 200 mg once daily or twice daily (e.g., once daily); or about 30 mg to about 150 mg once daily or twice daily (e.g., once daily)). In one embodiment, the therapeutically effective dose is a free-base equivalent strength of 30 mg, once daily or twice daily (e.g., once daily). In another embodiment, the therapeutically effective dose is a free-base equivalent strength of 50 mg, once daily or twice daily (e.g., once daily). In another embodiment, the therapeutically effective dose is a free-base equivalent strength of 75 mg, once daily or twice daily (e.g., once daily). In another embodiment, the therapeutically effective dose is a free-base equivalent strength of 100 mg, once daily or twice daily (e.g., once daily). In another embodiment, the therapeutically effective dose is a free-base equivalent strength of 125 mg, once daily or twice daily (e.g., once daily). In another embodiment, the therapeutically effective dose is a free-base equivalent strength of 150 mg, once daily or twice daily (e.g., once daily). In another embodiment, the therapeutically effective dose is a free-base equivalent strength of 175 mg, once daily or twice daily (e.g., once daily). In another embodiment, the therapeutically effective dose is a free-base equivalent strength of 200 mg, once daily or twice daily (e.g., once daily). In another embodiment, the therapeutically effective dose is a free-base equivalent strength of 225 mg, once daily or twice daily (e.g., once daily). In another embodiment, the therapeutically effective dose is a free-base equivalent strength of 250 mg, once daily or twice daily (e.g., once daily). In another embodiment, the therapeutically effective dose is a free-base equivalent strength of 275 mg, once daily or twice daily (e.g., once daily). In another embodiment, the therapeutically effective dose is a free-base equivalent strength of 300 mg, once daily or twice daily (e.g., once daily).

In some embodiments, in the methods of the present invention, a pharmaceutically acceptable salt of compound 1 is administered orally as any combination of 5, 10, 50, or 200 mg free-base equivalent strength tablets, twice daily or once daily (e.g., once daily). In some embodiments, compound 2 is administered orally as any combination of 5, 10, 50, or 200 mg free-base equivalent strength tablets, twice daily or once daily (e.g., once daily). In some embodiments, a crystalline form of compound 2 is administered orally as any combination of 5, 10, 50, or 200 mg free-base equivalent strength tablets, twice daily or once daily (e.g., once daily).

In some embodiments, in the methods of the present invention, a pharmaceutically acceptable salt of compound 1 is administered orally as any combination of 5, 10, 50, 100, 150 or 200 mg free-base equivalent strength tablets, twice daily or once daily (e.g., once daily). In some embodiments, compound 2 is administered orally as any combination of 5, 10, 50, 100, 150 or 200 mg free-base equivalent strength tablets, twice daily or once daily (e.g., once daily). In some embodiments, a crystalline form of compound 2 is administered orally as any combination of 5, 10, 50, 100, 150 or 200 mg free-base equivalent strength tablets, twice daily or once daily (e.g., once daily).

Also provided is a method of treating an advanced solid tumor, for example, a glioma, melanoma, chondrosarcoma, or cholangiocarcinoma (e.g., glioma), or treating angioimmunoblastic T-cell lymphoma (AITL), each characterized by the presence of a mutant allele of IDH2, comprising administering to a subject in need thereof compound 2 at a dose of at least about 30 mg (free-base equivalent strength) (e.g., in an amount from about 30 mg to about 300 mg; about 30 mg to about 200 mg; or about 30 mg to about 150 mg (free-base equivalent strength)) once daily.

In some embodiments, the method of treating an advanced solid tumor, for example, a glioma, melanoma, chondrosarcoma, or cholangiocarcinoma (e.g., glioma), or treating angioimmunoblastic T-cell lymphoma (AITL), each characterized by the presence of a mutant allele of IDH2, comprises administering to subject in need thereof compound 1, or a crystalline form thereof; or compound 2, or a crystalline form thereof, at a dose of at least about 30 mg (free-base equivalent strength) (e.g., in an amount from about 30 mg to about 300 mg; about 30 mg to about 200 mg; or about 30 mg to about 150 mg (free-base equivalent strength)) once daily.

In some embodiments, the second daily administration is provided between about 12 hours and about 36 hours after the first administration, for example, about 24 hours.

In one embodiment, the dose is 30 mg (free-base equivalent strength), once daily. In another embodiment, the dose is 50 mg (free-base equivalent strength), once daily. In another embodiment, the dose is 75 mg (free-base equivalent strength), once daily. In another embodiment, the dose is 100 mg (free-base equivalent strength), once daily. In another embodiment, the dose is 125 mg (free-base equivalent strength), once daily. In another embodiment, the dose is 150 mg (free-base equivalent strength), once daily. In another embodiment, the dose is 175 mg (free-base equivalent strength), once daily. In another embodiment, the dose is 200 mg (free-base equivalent strength), once daily. In another embodiment, the dose is 225 mg (free-base equivalent strength), once daily. In another embodiment, the dose is 250 mg (free-base equivalent strength), once daily.

In some embodiments, the method of treating an advanced solid tumor, for example, a glioma, melanoma, chondrosarcoma, or cholangiocarcinoma (e.g., glioma), or treating angioimmunoblastic T-cell lymphoma (AITL), each characterized by the presence of a mutant allele of IDH2, comprises administering to subject in need thereof compound 1, or a crystalline form thereof; or compound 2, or a crystalline form thereof, at a dose of from about 75 mg to about 150 mg (free-base equivalent strength) once daily.

In one embodiment, the method is a method of treating an advanced solid tumor, for example, a glioma, melanoma, chondrosarcoma, or cholangiocarcinoma (e.g., glioma), or treating angioimmunoblastic T-cell lymphoma (AITL), each characterized by the presence of a mutant allele of IDH2, comprising administering to subject in need thereof compound 1, or a crystalline form thereof; or compound 2, or a crystalline form thereof, in the oral dosage form of a tablet, at a dose of from about 75 mg to about 150 mg (free-base equivalent strength), once daily.

In some embodiments, the second daily administration is provided between about 12 hours and about 36 hours after the first administration, for example, about 24 hours.

In some embodiments, the methods described herein include oral administration of compound 1, or a crystalline form thereof; or compound 2, or a crystalline form thereof to a subject at a dose of about 30 mg, about 50 mg, about 75 mg, about 100 mg, 125 mg, about 150 mg, about 175 mg, about 200 mg, about 225 mg, or about 250 mg (each of which is the free-base equivalent strength) once daily.

In some embodiments, the method of treating an advanced solid tumor, for example, a glioma, melanoma, chondrosarcoma, or cholangiocarcinoma (e.g., glioma), or treating angioimmunoblastic T-cell lymphoma (AITL), each characterized by the presence of a mutant allele of IDH2, comprises administering to subject in need thereof compound 2 at a dose of from about 75 mg to about 300 mg (free-base equivalent strength), once daily (e.g., about 75 mg to about 200 mg (free-base equivalent strength), once daily).

In some embodiments, the method of treating an advanced solid tumor, for example, a glioma, melanoma, chondrosarcoma, or cholangiocarcinoma (e.g., glioma), or treating angioimmunoblastic T-cell lymphoma (AITL), each characterized by the presence of a mutant allele of IDH2, comprises administering to subject in need thereof compound 1, or a crystalline form thereof; or compound 2, or a crystalline form thereof, at a dose of from about 75 mg to about 300 mg (free-base equivalent strength), once daily (e.g., about 75 mg to about 200 mg (free-base equivalent strength), once daily).

In some embodiments, the method of treating an advanced solid tumor, for example, a glioma, melanoma, chondrosarcoma, or cholangiocarcinoma (e.g., glioma), or treating angioimmunoblastic T-cell lymphoma (AITL), or a crystalline form thereof; comprises administering to subject in need thereof compound 2, or a crystalline form thereof at a dose of from about 75 mg to about 300 mg (free-base equivalent strength), once daily (e.g., about 75 mg to about 200 mg (free-base equivalent strength), once daily).

In one embodiment, the dose is 100 mg (free-base equivalent strength), once daily. In one embodiment, the dose is 150 mg (free-base equivalent strength), once daily. In one embodiment, the dose is 175 mg (free-base equivalent strength), once daily. In one embodiment, the dose is 200 mg (free-base equivalent strength), once daily. In one embodiment, the dose is 225 mg (free-base equivalent strength), once daily. In one embodiment, the dose is 250 mg (free-base equivalent strength), once daily. In one embodiment, the dose is 275 mg (free-base equivalent strength), once daily.

In some embodiments, the method of treating an advanced solid tumor, for example, a glioma, melanoma, chondrosarcoma, or cholangiocarcinoma (e.g., glioma), or treating angioimmunoblastic T-cell lymphoma (AITL), each characterized by the presence of a mutant allele of IDH2, comprises administering to subject in need thereof compound 2, or a crystalline form thereof; or compound 2, or a crystalline form thereof at a dose of from about 150 mg to about 300 mg (free-base equivalent strength), once daily (e.g., about 150 mg to about 200 mg (free-base equivalent strength), once daily).

In one embodiment, the method is a method of treating an advanced solid tumor such as glioma characterized by the presence of a mutant allele of IDH2 comprises administering to subject in need thereof compound 1, or a crystalline form thereof; or compound 2, or a crystalline form thereof at a dose of from about 100 mg to about 300 mg (free-base equivalent strength), once daily (e.g., about 150 mg to about 200 mg (free-base equivalent strength), once daily).

In one embodiment, the method is a method of treating an advanced solid tumor such as glioma characterized by the presence of a mutant allele of IDH2 comprises administering to subject in need thereof compound 2, or a crystalline form thereof, in the oral dosage form of a tablet, at a dose of from about 150 mg to about 300 mg (free-base equivalent strength) once daily.

In one embodiment, the method is a method of treating angioimmunoblastic T-cell lymphoma (AITL) characterized by the presence of a mutant allele of IDH2 comprises administering to subject in need thereof compound 1, or a crystalline form thereof; or compound 2, or a crystalline form thereof at a dose of from about 100 mg to about 300 mg (free-base equivalent strength) once daily.

In one embodiment, the method is a method of treating angioimmunoblastic T-cell lymphoma (AITL) characterized by the presence of a mutant allele of IDH2 comprises administering to subject in need thereof compound 1, or a crystalline form thereof; or compound 2, or a crystalline form thereof, in the oral dosage form of a tablet, at a dose of from about 150 mg to about 300 mg (free-base equivalent strength) once daily.

In some embodiments, the method includes oral administration of compound 1, or a crystalline form thereof; or compound 2, or a crystalline form thereof to a subject at a dose of about 75, about 100 mg, about 125 mg, about 150 mg, about 175 mg, about 200 mg, about 225 mg, about 250 mg, about 275 mg, or about 300 mg (each of which is the free-base equivalent strength) once daily.

It will be understood that a therapeutically effective dose of compound 1, or a crystalline form thereof; or a therapeutically effective dose of compound 2, or a crystalline form thereof, may be taken at any time of the day or night. In other embodiments, a therapeutically effective dose of compound 1, or a crystalline form thereof; or a therapeutically effective dose of compound 2, or a crystalline form thereof is taken in the morning or evening. It will be understood that a therapeutically effective dose of compound 1, or a crystalline form thereof; or a therapeutically effective dose of compound 2 or a crystalline form thereof may be taken with or without food. In some embodiments, a therapeutically effective dose of compound 1, or a crystalline form thereof; or a therapeutically effective dose of compound 2, or a crystalline form thereof, is taken with a meal (e.g., administration of single oral dose 30 minutes after the start of a high-fat meal [high-fat Food and Drug Administration standard meal: for example, 2 extra-large eggs cooked in butter, 2 pieces cured, cooked bacon, 2 pieces enriched white bread with butter, 4 ounces hashed brown potatoes, and 8 ounces whole milk (3.3%)]). In some embodiments, subjects are required to fast for at least 4 hours following a therapeutically effective dose of compound 1, or a crystalline form thereof; or a therapeutically effective dose of compound 2, or a crystalline form thereof. Water is allowed ad libitum except 1 hour before until 1 hour after dosing of compound 1, or a crystalline form thereof; or compound 2, or a crystalline form thereof.

In some embodiments, a therapeutically effective dose of compound 1, or a crystalline form thereof; or a therapeutically effective dose of compound 2, or a crystalline form thereof is taken while fasting (e.g., administration of single oral dose following at least a 2 hour fast).

In one embodiment, the invention encompasses an oral dosage form comprising a therapeutically effective dose of compound 1, or a crystalline form thereof; or a therapeutically effective dose of compound 2, or a crystalline form thereof. In another embodiment, the invention encompasses a 5 mg, 10 mg, 25 mg, 50 mg, 100 mg, 150 mg, or 200 mg (each of which is the free-base equivalent strength) oral dosage form, comprising compound 1, or a crystalline form thereof; or compound 2, or a crystalline form thereof. In one embodiment, the oral dosage form further comprises one or more pharmaceutically acceptable carrier(s).

In one embodiment, the invention encompasses compound 1, or a crystalline form thereof; or compound 2, or a crystalline form thereof, for use in a method of treating an advanced solid tumor, for example, a glioma, melanoma, chondrosarcoma, or cholangiocarcinoma (e.g., glioma), or treating angioimmunoblastic T-cell lymphoma (AITL), each characterized by the presence of a mutant allele of IDH2 in a subject in need thereof. In one embodiment, the invention encompasses a pharmaceutical composition comprising a therapeutically effective dose of compound 1, or a crystalline form thereof; or a therapeutically effective dose of compound 2, or a crystalline form thereof, and one or more pharmaceutically acceptable carrier(s) for use in a method of treating an advanced solid tumor, for example, a glioma, melanoma, chondrosarcoma, or cholangiocarcinoma (e.g., glioma), or treating angioimmunoblastic T-cell lymphoma (AITL), each characterized by the presence of a mutant allele of IDH2 in a subject in need thereof.

Also provided is a method of decreasing a pre-treatment or baseline level (e.g., Day −3 pre-treatment in patients, or levels measured in subjects without IDH-2 gene mutated disease) of 2-HG (e.g., as measured by proton magnetic resonance spectroscopy or magnetic resonance images; a method of modifying (e.g., decreasing) a pre-treatment or baseline level (e.g., Day −3 pre-treatment in patients, or levels measured in subjects without IDH-2 gene mutated disease) Ki67 level in a tumor sample; a method of modifying, e.g., decrease histone and DNA methylation profile in a tumor cell; a method of evaluation of a gene expression profile or other prognostic marker that could predict anti-tumor activity or resistance; a method of evaluation of a change in a metabolic profile in an IDH2-mutated tumor cell; and a method of monitoring of plasma cholesterol and 4β-OH cholesterol level, for example, as a cytochrome P450 (CYP) 3A4 induction marker, in a method described herein, for example a method of treating a subject having an advanced solid tumor, for example, a glioma, melanoma, chondrosarcoma, or cholangiocarcinoma (e.g., glioma), or treating angioimmunoblastic T-cell lymphoma (AITL), each characterized by the presence of a mutant allele of IDH2, comprising administering to the subject (a) compound 1, or a crystalline form thereof; or compound 2, or a crystalline form thereof at a dose of at least about 30 mg (free-base equivalent strength), once daily or twice daily, for example, once daily (e.g., in an amount from about 30 mg to about 300 mg equivalent to free-base compound 1 (e.g., about 30 mg to about 200 mg once daily or twice daily; or about 30 mg to about 150 mg once daily or twice daily (e.g., once daily)), or (b) a pharmaceutical composition comprising a compound 1, or a crystalline form thereof; or compound 2, or a crystalline form thereof at a dose of at least about 30 mg (free-base equivalent strength) (e.g., in an amount from about 30 mg to about 300 mg equivalent to free-base compound 1 (e.g., about 30 mg to about 200 mg once daily or twice daily (e.g., once daily); or about 30 mg to about 150 mg once daily or twice daily (e.g., once daily)), and one or more pharmaceutically acceptable carrier(s).

Also provided is a method of evaluating the efficacy of treatment in a subject having an advanced solid tumor, for example, a glioma, melanoma, chondrosarcoma, or cholangiocarcinoma (e.g., glioma), or treating angioimmunoblastic T-cell lymphoma (AITL), each characterized by the presence of a mutant allele of IDH2, the method comprising a method of assessing a response to treatment comprising:

acquiring knowledge of the pre-treatment or baseline level (e.g., measuring the pre-treatment or baseline level) of a tumor sample (e.g., using computed tomography or MRI in a subject with a solid tumor such as a glioma, melanoma, chondrosarcoma, or cholangiocarcinoma (e.g., glioma), or a positron-emmision tomography (PET)/CT scan for a subject having a solid tumor other than glioma, or having AITL;

administering to the subject (a) compound 1, or a crystalline form thereof; or compound 2, or a crystalline form thereof at a dose of at least about 30 mg (free-base equivalent strength) (e.g., in an amount from about 30 mg to about 300 mg equivalent to free-base compound 1 (e.g., about 30 mg to about 200 mg once daily or twice daily (e.g., once daily); or about 30 mg to about 150 mg once daily or twice daily (e.g., once daily)), or (b) a pharmaceutical composition comprising compound 1, or a crystalline form thereof; or compound 2, or a crystalline form thereof at a dose of at least about 30 mg (free-base equivalent strength) (e.g., in an amount from about 30 mg to about 300 mg equivalent to free-base compound 1 (e.g., about 30 mg to about 200 mg once daily or twice daily (e.g., once daily); or about 30 mg to about 150 mg once daily or twice daily (e.g., once daily)), and one or more pharmaceutically acceptable carrier(s);

acquiring knowledge of the post-treatment level (e.g., measuring the post-treatment level) of a tumor sample (e.g., using computed tomography or MRI in a subject with a solid tumor such as a glioma, or a positron-emmision tomography (PET)/CT scan for a subject having a solid tumor other than glioma, or having AITL;

comparing the post-treatment level of bone marrow and/or peripheral blood blast cells in the subject with the pre-treatment or baseline level; and determining whether the treatment is effective (e.g., according to RECIST v. 1.1, by modifies RANO criteria, or by IWG criteria (for example for an AITL subject).

In one embodiment the mutant IDH2 inhibitor is a polypeptide. In an embodiment the polypeptide acts as a dominant negative with respect to the neoactivity of the mutant enzyme. The polypeptide can correspond to full length IDH2 or a fragment thereof. The polypeptide need not be identical with the corresponding residues of wildtype IDH2, but in embodiments has at least 60, 70, 80, 90 or 95% homology with wildtype IDH2.

In one embodiment the mutant IDH2 inhibitor decreases the affinity of an IDH2 neoactive mutant protein for NADH, NADPH or a divalent metal ion, e.g., $Mg^{2+}$ or $Mn^{2+}$, or decreases the levels or availability of NADH, NADPH or divalent metal ion, e.g., $Mg^{2+}$ or $Mn^{2+}$, e.g., by competing for binding to the mutant enzyme. In an embodiment the enzyme is inhibited by replacing $Mg^{2+}$ or $Mn^{2+}$ with $Ca^{2+}$.

In one embodiment the mutant IDH2 inhibitor reduces the level a neoactivity of IDH2, e.g., 2-HG neoactivity.

In one embodiment the mutant IDH2 inhibitor reduces the level of the product of a mutant having a neoactivity of an IDH2 mutant, e.g., it reduces the level of 2-HG, e.g., R-2-HG.

In an embodiment the mutant IDH2 inhibitor interacts directly with, e.g., binds, either the mutant IDH2 protein or interacts directly with, e.g., binds, the mutant IDH2 mRNA.

In an embodiment the mutant IDH2 inhibitor interacts directly with, e.g., it binds to, the mutant IDH2 protein.

In an embodiment the mutant IDH2 inhibitor interacts directly with, e.g., it binds to, the mutant IDH2 mRNA.

In an embodiment the mutant IDH2 inhibitor reduces the amount of neoactive enzyme activity, e.g., by interacting with, e.g., binding to, mutant IDH2 protein.

In an embodiment the mutant IDH2 inhibitor is a small molecule, e.g., compound 2, and interacts with, e.g., binds, the mutant RNA, e.g., mutant IDH2 mRNA.

In some embodiments, the mutant IDH2 inhibitor may also comprise one or more isotopic substitutions. For example, H may be in any isotopic form, including $^1H$, $^2H$ (D or deuterium), and $^3H$ (T or tritium); C may be in any isotopic form, including $^{11}C$, $^{12}C$, $^{13}C$, and $^{14}C$; N may be in any isotopic form, including $^{13}N$, $^{14}N$ and $^{15}N$; O may be in any isotopic form, including $^{15}O$, $^{16}O$ and $^{18}O$; F may be in any isotopic form, including $^{18}F$; and the like. For example, the compound is enriched in a specific isotopic form of H, C, N, O and/or F by at least about 60%, 65%, 70%, 75%, 80%, 85%, 90%, 95%, 96%, 97%, 98%, or 99%. For example, isotopic substitutions to compound 2 or compound 1 may include 2-Methyl-1-[(4-[6-(trifluoromethyl)pyridin-2-yl]-6-{[2-(trifluoromethyl)pyridin-4-yl]amino}-1,3,5-triazin-2-yl-4-$^{14}C$)amino]propan-2-ol; 1-((4-(6-(difluoro(fluoro-$^{18}F$)methyl)pyridin-2-yl)-6-((2-(trifluoromethyl)pyridin-4-yl)amino)-1,3,5-triazin-2-yl)amino)-2-methylpropan-2-ol, 1-((4-((2-(difluoro(fluoro-$^{18}F$)methyl)pyridin-4-yl)amino)-6-(6-(trifluoromethyl)pyridin-2-yl)-1,3,5-triazin-2-yl)amino)-2-methylpropan-2-ol, 2-(((4-(6-(trifluoromethyl)pyridin-2-yl)-6-((2-(trifluoromethyl)pyridin-4-yl)amino)-1,3,5-triazin-2-yl)amino)methyl)propan-1,1,1,3,3,3-d6-2-ol; 2-methyl-1-((4-(6-(trifluoromethyl)pyridin-2-yl)-6-((2-(trifluoromethyl)

pyridin-4-yl)amino)-1,3,5-triazin-2-yl)amino)propan-1,1-d2-2-ol or pharmaceutically acceptable salts thereof (e.g., 2-Methyl-1-[(4-[6-(trifluoromethyl)pyridin-2-yl]-6-{[2-(trifluoromethyl)pyridin-4-yl]amino}-1,3,5-triazin-2-yl-4-$^{14}$C)amino]propan-2-ol methanesulfonate; 1-((4-(6-(difluoro (fluoro-$^{18}$F)methyl)pyridin-2-yl)-6-((2-(trifluoromethyl) pyridin-4-yl)amino)-1,3,5-triazin-2-yl)amino)-2-methylpropan-2-ol methanesulfonate, 1-((4-((2-(difluoro (fluoro-18F)methyl)pyridin-4-yl)amino)-6-(6-(trifluoromethyl)pyridin-2-yl)-1,3,5-triazin-2-yl)amino)-2-methylpropan-2-ol) methanesulfonate, 2-(((4-(6-(trifluoromethyl)pyridin-2-yl)-6-((2-(trifluoromethyl) pyridin-4-yl)amino)-1,3,5-triazin-2-yl)amino)methyl) propan-1,1,1,3,3,3-d6-2-ol methanesulfonate; 2-methyl-1-((4-(6-(trifluoromethyl)pyridin-2-yl)-6-((2-(trifluoromethyl)pyridin-4-yl)amino)-1,3,5-triazin-2-yl) amino)propan-1,1-d2-2-ol methanesulfonate).

These methods of treatment and pharmaceutical compositions are further illustrated by the detailed descriptions and illustrative examples given below.

Compositions and Routes of Administration

The mutant IDH2 inhibitors, e.g., compound 1, or a crystalline form thereof; or compound 2, or a crystalline form thereof utilized in the methods described herein may be formulated together with one or more pharmaceutically acceptable carrier(s) or adjuvant(s) into pharmaceutically acceptable compositions prior to being administered to a subject.

The term "pharmaceutically acceptable carrier or adjuvant" refers to a carrier or adjuvant that may be administered to a subject, together with a compound described herein, and which does not destroy the pharmacological activity thereof and is nontoxic when administered in doses sufficient to deliver a therapeutic amount of the compound.

In some embodiments, pharmaceutically acceptable carriers, adjuvants and vehicles that may be used in the pharmaceutical compositions include, but are not limited to, ion exchangers, alumina, aluminum stearate, lecithin, self-emulsifying drug delivery systems (SEDDS) such as d-a-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

In some embodiments, the pharmaceutical compositions may be administered orally, parenterally, by inhalation spray, topically, rectally, nasally, buccally, vaginally or via an implanted reservoir, preferably by oral administration or administration by injection. The pharmaceutical compositions of one aspect of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

In some embodiments, the pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

In some embodiments, the pharmaceutical compositions may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

In some embodiments, the pharmaceutical compositions may also be administered in the form of suppositories for rectal administration. These compositions can be prepared by mixing compound 1, or a crystalline form thereof; or compound 2, or a crystalline form thereof with a suitable non-irritating excipient which is solid at room temperature but liquid at the rectal temperature and therefore will melt in the rectum to release the active components. Such materials include, but are not limited to, cocoa butter, beeswax and polyethylene glycols.

In some embodiments, topical administration of the pharmaceutical compositions is useful when the desired treatment involves areas or organs readily accessible by topical application. For application topically to the skin, the pharmaceutical composition should be formulated with a suitable ointment containing the active components suspended or dissolved in a carrier. Carriers for topical administration of compound 1, or a crystalline form thereof; or compound 2, or a crystalline form thereof include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of one aspect of this invention may also be topically applied to the lower intestinal tract by rectal suppository formulation or in a suitable enema formulation. Topically-transdermal patches are also included in one aspect of this invention.

In some embodiments, the pharmaceutical compositions may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The mutant IDH2 inhibitors, e.g., compound 1, or a crystalline form thereof; or compound 2, or a crystalline form thereof, utilized in the methods described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions may be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

A subject may be administered a dose of a mutant IDH2 inhibitor, e.g., compound 1, or a crystalline form thereof; or compound 2, or a crystalline form thereof, as described in the Examples. Lower or higher doses than those recited above may be required. Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition, crystalline form or combination of one aspect of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

Some embodiments of the invention are directed toward a tablet comprising at least one pharmaceutically acceptable carrier; and a mutant IDH2 inhibitor.

Some embodiments of the invention are directed toward a tablet comprising at least one pharmaceutically acceptable carrier; and compound 1, or a crystalline form thereof; or compound 2, or a crystalline form thereof. Some embodiments of the invention are directed toward a tablet comprising at least one pharmaceutically acceptable carrier; and compound 2 or a crystalline form thereof.

Some embodiments of the invention are directed toward a tablet comprising at least one pharmaceutically acceptable carrier or diluent; and compound 1, or a crystalline form thereof; or compound 2, or a crystalline form thereof. In other embodiments, the crystalline form of compound 1 or compound 2 is at least 90% by weight of a particular crystalline form; the particular crystalline form being a form described herein. In other embodiments, the crystalline form of compound 1 or compound 2 is at least 95% by weight of a particular crystalline form; the particular crystalline form being a form described herein.

Methods of Use

The inhibitory activities of compound 1 or a crystalline form thereof; or compound 2, or a crystalline form thereof, against IDH2 mutants (e.g., IDH2R140Q and IDH2R172K) can be tested by methods described in Example 12 of PCT Publication No. WO 2013/102431 and US Publication No. US 2013/0190287 hereby incorporated by reference in their entirety, or analogous methods.

Provided is a method for inhibiting a mutant IDH2 activity, comprising contacting a subject in need thereof with a mutant IDH2 inhibitor. In one embodiment, the method for inhibiting a mutant IDH2 activity comprises contacting a subject in need thereof with compound 1 or compound 2 (e.g., compound 2). In one embodiment, the advanced solid tumor, for example, a glioma, melanoma, chondrosarcoma, or cholangiocarcinoma (e.g., glioma), or angioimmunoblastic T-cell lymphoma (AITL) to be treated is characterized by a mutant allele of IDH2 wherein the IDH2 mutation results in a new ability of the enzyme to catalyze the NAPH-dependent reduction of α-ketoglutarate to R(−)-2-hydroxyglutarate in a patient. In one aspect of this embodiment, the mutant IDH2 has an R140X mutation. In another aspect of this embodiment, the R140X mutation is a R140Q mutation. In another aspect of this embodiment, the R140X mutation is a R140W mutation. In another aspect of this embodiment, the R140X mutation is a R140L mutation. In another aspect of this embodiment, the mutant IDH2 has an R172X mutation. In another aspect of this embodiment, the R172X mutation is a R172K mutation. In another aspect of this embodiment, the R172X mutation is a R172G mutation.

In another embodiment, the method for inhibiting a mutant IDH2 activity comprises contacting a subject in need thereof with compound 1, or a crystalline form thereof; or compound 2, or a crystalline form thereof. In one embodiment, the advanced solid tumor, for example, a glioma, melanoma, chondrosarcoma, or cholangiocarcinoma (e.g., glioma), or treating angioimmunoblastic T-cell lymphoma (AITL), or angioimmunoblastic T-cell lymphoma (AITL) to be treated is characterized by a mutant allele of IDH2 wherein the IDH2 mutation results in a new ability of the enzyme to catalyze the NAPH-dependent reduction of α-ketoglutarate to R(−)-2-hydroxyglutarate in a patient. In one aspect of this embodiment, the mutant IDH2 has an R140X mutation. In another aspect of this embodiment, the R140X mutation is a R140Q mutation. In another aspect of this embodiment, the R140X mutation is a R140W mutation. In another aspect of this embodiment, the R140X mutation is a R140L mutation. In another aspect of this embodiment, the mutant IDH2 has an R172X mutation. In another aspect of this embodiment, the R172X mutation is a R172K mutation. In another aspect of this embodiment, the R172X mutation is a R172G mutation. Advanced solid tumors, for example, a glioma, and angioimmunoblastic T-cell lymphoma (AITL), each characterized by the presence of a mutant allele of IDH2, can be analyzed by sequencing cell samples to determine the presence and specific nature of (e.g., the changed amino acid present at) a mutation at amino acid 140 and/or 172 of IDH2.

In one embodiment, the efficacy of treatment of advanced solid tumors, for example, a glioma, melanoma, chondrosarcoma, or cholangiocarcinoma (e.g., glioma), and angioimmunoblastic T-cell lymphoma (AITL), each characterized by the presence of a mutant allele of IDH2, is monitored by measuring the levels of 2HG in the subject. Typically levels of 2HG are measured prior to treatment, wherein an elevated level is indicated for the use of compound 2 to treat advanced solid tumors, for example, a glioma, and angioimmunoblastic T-cell lymphoma (AITL), each characterized by the presence of a mutant allele of IDH2.

In one embodiment, the efficacy of treatment of advanced solid tumors, for example, a glioma, melanoma, chondrosarcoma, or cholangiocarcinoma (e.g., glioma), and angioimmunoblastic T-cell lymphoma (AITL), each characterized by the presence of a mutant allele of IDH2, is monitored by measuring the levels of 2-HG in the subject. Typically levels of 2-HG are measured prior to treatment, wherein an elevated level is indicated for the use of compound 1, or a crystalline form thereof; or compound 2, or a crystalline form thereof, to treat an advanced solid tumor, for example, a glioma, melanoma, chondrosarcoma, or cholangiocarcinoma (e.g., glioma), or angioimmunoblastic T-cell lymphoma (AITL), each characterized by the presence of a mutant allele of IDH2. Once the elevated levels are established, the level of 2-HG is determined during the course of and/or following termination of treatment to establish efficacy. In certain aspects, the level of 2-HG is only determined during the course of and/or following termination of treatment. A reduction of 2-HG levels during the course of treatment and following treatment is indicative of efficacy. Similarly, a determination that 2-HG levels are not elevated during the course of or following treatment is also indicative of efficacy. Typically, the these 2-HG measurements will be utilized together with other well-known determinations of efficacy of cancer treatment, such as reduction in number and size of tumors and/or other cancer-associated lesions, evaluation of bone marrow biopsies and/or aspirates, complete blood counts, examination of peripheral blood films, improvement in the general health of the subject, and alterations in other biomarkers that are associated with cancer treatment efficacy.

Also provided is a method of inhibiting 2-HG as compared to a pre-treatment or baseline level (e.g., Day −3 pre-treatment in patients, or levels measured in subjects without IDH-2 gene mutated disease) of 2-HG (e.g., by at least 50%) in a subject having an advanced solid tumor, for example, a glioma, melanoma, chondrosarcoma, or cholangiocarcinoma (e.g., glioma), or angioimmunoblastic T-cell lymphoma (AITL), each characterized by the presence of a mutant allele of IDH2, comprising:

acquiring knowledge of the pre-treatment or baseline level (e.g., measuring the pre-treatment or baseline level) of 2-HG in the subject;

administering to the subject (a) compound 1, or a crystalline form thereof; or compound 2, or a crystalline form thereof at a dose of at least about 30 mg (free-base equivalent strength) (e.g., in an amount from about 30 mg to about 300 mg equivalent to free-base compound 1), or (b) a pharmaceutical composition comprising compound 1, or a crystalline form thereof, or compound 2, or a crystalline form thereof at a dose of at least about 30 mg (free-base equivalent strength) (e.g., in an amount from about 30 mg to about 300 mg equivalent to free-base compound 1), and one or more pharmaceutically acceptable carrier(s);

acquiring knowledge of the post-treatment level (e.g., measuring the post-treatment level) of 2-HG in the subject;

comparing the post-treatment level of 2-HG in the subject with the pre-treatment or baseline level; and determining that the level of 2-HG is inhibited (e.g., by at least 50%).

In some embodiments, the method comprises inhibiting 2-HG in patients having or determined to have an IDH2 R140Q mutation by at least 50% (e.g., 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100%) as compared to a pre-treatment or baseline level (e.g., Day −3 pretreatment in patients, or levels measured in subjects without IDH-2 gene mutated disease). In some embodiments, the method comprises inhibiting 2-HG in patients having or determined to have an IDH2 R172K mutation by up to 60% (e.g., decreasing the level of 2-HG by up to 50%, 51%, 52%, 53%, 54%, 55%, 56%, 57%, 58%, 59%, or 60%) as compared to a pre-treatment or baseline level (e.g., Day −3 pre-treatment in patients, or levels measured in subjects without IDH-2 gene mutated disease). In some embodiments, measuring the 2-HG level in the subject may be achieved by spectroscopic analysis, e.g., magnetic resonance-based analysis, e.g., MRI and/or MRS measurement, sample analysis of bodily fluid, such as blood, plasma, urine, bone marrow, or spinal cord fluid analysis, or by analysis of surgical material, e.g., by mass-spectroscopy (e.g. LC-MS, GC-MS).

2-HG can be detected in a sample by the methods of PCT Publication No. WO 2013/102431 and US Publication No. US 2013/0190287 hereby incorporated by reference in their entirety, or by analogous methods.

In one embodiment 2-HG is directly evaluated.

In another embodiment a derivative of 2-HG formed in process of performing the analytic method is evaluated. By way of example such a derivative can be a derivative formed in MS analysis. Derivatives can include a salt adduct, e.g., a Na adduct, a hydration variant, or a hydration variant which is also a salt adduct, e.g., a Na adduct, e.g., as formed in MS analysis.

In another embodiment a metabolic derivative of 2-HG is evaluated. Examples include species that build up or are elevated, or reduced, as a result of the presence of 2-HG, such as glutarate or glutamate that will be correlated to 2-HG, e.g., R-2-HG.

Exemplary 2-HG derivatives include dehydrated derivatives such as the compounds provided below or a salt adduct thereof:

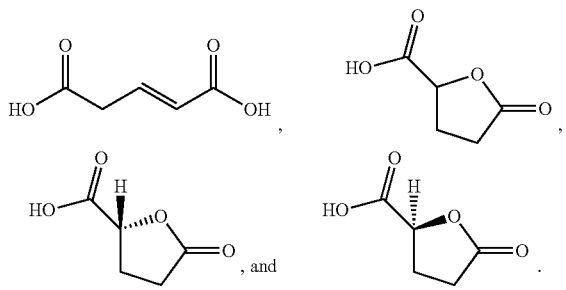
, and

In one embodiment, the an advanced solid tumor, for example, a glioma, melanoma, chondrosarcoma, or cholangiocarcinoma (e.g., glioma), or angioimmunoblastic T-cell lymphoma (AITL), each characterized by the presence of a mutant allele of IDH2, is a tumor wherein at least 30, 40, 50, 60, 70, 80 or 90% of the tumor cells carry an IDH2 mutation, and in particular an IDH2 R140Q, R140W, or R140L and/or R172K or R172G mutation, at the time of diagnosis or treatment.

In some embodiments, the subject has or is determined to have an IDH2 gene-mutated disease (e.g., R140Q mutation or R172K mutation) at the time of diagnosis or treatment. In some embodiments, the subject also has or is determined to have a mutation selected from FLT3-ITD (Fms-related tyrosine kinase 3 (FLT3) internal tandem duplication (ITD)), CEPBA (CCAAT/enhancer binding protein alpha), NPM1 (nucleophosmin (neucleolar phosphoprotein B23)), and DNMT3A (DNA (cytosine-5-)methyltransferase 3 alpha, ASXL1: additional sex combs like 1) at the time of diagnosis or treatment.

In some embodiments, the subject has normal cytogenetics prior to treatment. In some other embodiments, the subject has abnormal or unfavorable cytogenetics, for example, one or more of: Monosomy 7 (or partial deletion of the long arm of chromosome 7 (7q-)), Trisomy 8, Trisomy 11, translocation t(17; 18), or translocation t(1; 13) prior to treatment.

In an embodiment, the method comprises treating melanoma, glioma, chondrosarcoma, or cholangiocarcinoma, for example, advanced glioma, melanoma, chondrosarcoma, or cholangiocarcinoma.

The methods described herein are useful in treating cancer in nervous system, e.g., brain tumor, e.g., glioma, e.g., glioblastoma multiforme (GBM).

Gliomas, a type of brain tumors, can be classified as grade I to grade IV on the basis of histopathological and clinical criteria established by the World Health Organization (WHO). WHO grade I gliomas are often considered benign. Gliomas of WHO grade II or III are invasive, progress to higher-grade lesions. WHO grade IV tumors (glioblastomas) are the most invasive form. Exemplary brain tumors include, e.g., astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma); oligodendroglial tumor (e.g., oligodendroglioma, and anaplastic oligodendroglioma); oligoastrocytic tumor (e.g., oligoastrocytoma, and anaplastic oligoastrocytoma); ependymoma (e.g., myxopapillary ependymoma, and anaplastic ependymoma); medulloblastoma; primitive neuroectodermal tumor, schwannoma, meningioma, meatypical meningioma, anaplastic meningioma; and pituitary adenoma. Exemplary cancers are described in Acta Neuropathol (2008) 116:597-602 and N Engl J Med. 2009 Feb. 19; 360(8):765-73, the contents of which are each incorporated herein by reference.

In embodiments the advanced solid tumor is glioma. In an embodiment, the glioma has recurred or progressed following a prior treatment such as standard therapy. In an embodiment, the advanced solid tumor such as glioma has not responded to standard therapy. In one embodiment, compound 1, or a crystalline form thereof; or compound 2, or a crystalline form thereof, is administered as a second line, third line, or fourth line treatment for the advanced solid tumor such as glioma. In one embodiment, compound 1, or a crystalline form thereof; or compound 2, or a crystalline form thereof, is administered after a first relapse. In one embodiment, compound 2 is administered after primary induction failure. In one embodiment, compound 2 is administered after re-induction failure. In one embodiment, after relapse and subsequent re-induction failure, compound 1, or a crystalline form thereof; or compound 2, or a crystalline form thereof, is administered.

In an embodiment, the method includes a method of treating angioimmunoblastic T-cell lymphoma (AITL). Angioimmunoblastic T-cell lymphoma (AITL) is a rare, aggressive (fast-growing) T-cell lymphoma that accounts for one percent to two percent of all NHL cases in the United States. Elderly patients are more likely to have AITL, and it occurs more often in men than women. Symptoms of AITL include high fever, night sweats, skin rash, and autoimmune disorders such as autoimmune hemolytic anemia (AIHA) and immune thrombocytopenia (ITP). As a result of these autoimmune disorders, the body's immune system does not recognize, and consequently destroys, its own cells and tissues, such as red blood cells (in the case of AIHA) or platelets (in the case of ITP). The majority of patients with AITL are diagnosed with advanced-stage disease, either stage III or stage IV disease. In stage III, affected lymph nodes are found both above and below the diaphragm. In stage IV, one or more organs beyond the lymph nodes are affected, such as the bone, bone marrow, skin, or liver. Less-extensive disease, stage I or II, is rare. Patients with stage I have localized disease that has not spread beyond the tumor, and with stage II, if the cancer has spread, it has affected only a nearby lymph node.

In some embodiments, the AITL is relapsed and/or primary refractory. In other embodiments, the AITL is untreated. In one embodiment, compound 1, or a crystalline form thereof; or compound 2, or a crystalline form thereof, is administered as a first line treatment for AITL. In one embodiment, compound 1, or a crystalline form thereof, or compound 2, or a crystalline form thereof, is administered as a second line, third line, or fourth line treatment for AITL. In one embodiment, compound 2 is administered as a first line treatment for AITL. In one embodiment, compound 2 is administered as a second line, third line, or fourth line treatment for AITL. In one embodiment, compound 1, or a crystalline form thereof; or compound 2, or a crystalline form thereof, is administered after a first relapse. In one embodiment, compound 2 is administered after primary induction failure. In one embodiment, compound 1, or a crystalline form thereof; or compound 2, or a crystalline form thereof is administered after re-induction failure. In one embodiment, administration of compound 1, or a crystalline form thereof; or compound 2, or a crystalline form thereof can occur prior to, during, or after transplant. In one embodiment, compound 1, or a crystalline form thereof; or compound 2, or a crystalline form thereof is administered after a relapse that is post-transplant.

Treatment methods described herein can additionally comprise various evaluation steps prior to and/or following treatment with a mutant IDH2 inhibitor, e.g., compound 1, or a crystalline form thereof; or compound 2, or a crystalline form thereof.

In one embodiment, prior to and/or after treatment with a mutant IDH2 inhibitor, e.g., compound 1, or a crystalline form thereof; or compound 2, or a crystalline form thereof, the method further comprises the step of evaluating the growth, size, weight, invasiveness, stage and/or other phenotype of the advanced solid tumor, such as glioma, melanoma, chondrosarcoma, or cholangiocarcinoma (e.g., glioma), or AITL.

In one embodiment, prior to and/or after treatment with a mutant IDH2 inhibitor, e.g., compound 1, or a crystalline form thereof; or compound 2, or a crystalline form thereof, the method further comprises the step of evaluating the IDH2 genotype of the cancer. This may be achieved by ordinary methods in the art, such as DNA sequencing, immuno analysis, and/or evaluation of the presence, distribution or level of 2-HG.

In one embodiment, prior to and/or after treatment with a mutant IDH2 inhibitor, e.g., compound 1, or a crystalline form thereof; or compound 2, or a crystalline form thereof, the method further comprises the step of determining the 2-HG level in the subject. This may be achieved by spectroscopic analysis, e.g., magnetic resonance-based analysis, e.g., MRI and/or MRS measurement, sample analysis of bodily fluid, such as blood, plasma, urine, bone marrow, or spinal cord fluid analysis, or by analysis of surgical material, e.g., by mass-spectroscopy (e.g. LC-MS, GC-MS).

Crystalline Forms

Provided are crystalline forms of compound 1 and compound 2.

In one embodiment, compound 1 is a single crystalline form, or any one of the single crystalline forms described herein. Also provided are pharmaceutical compositions comprising at least one pharmaceutically acceptable carrier or diluent; and compound 1, wherein compound 1 is a single crystalline form, or any one of the crystalline forms being described herein. Also provided are uses of compound 1, wherein compound 1 is a single crystalline form, or any one of the single crystalline forms described herein, to prepare a pharmaceutical composition.

In one embodiment, compound 2 is a single crystalline form, or any one of the single crystalline forms described herein. Also provided are pharmaceutical compositions comprising at least one pharmaceutically acceptable carrier or diluent; and compound 2, wherein compound 2 is a single crystalline form, or any one of the crystalline forms being described herein. Also provided are uses of compound 2, wherein compound 2 is a single crystalline form, or any one of the single crystalline forms described herein, to prepare a pharmaceutical composition.

Also provided are methods of treating an advanced solid tumor, for example, a glioma, melanoma, chondrosarcoma, or cholangiocarcinoma (e.g., glioma), or treating angioimmunoblastic T-cell lymphoma (AITL), each characterized by the presence of a mutant allele of IDH2, comprising administering to subject in need thereof (a) a single crystalline form of compound 1 or compound 2, or (b) a pharmaceutical composition comprising (a) and a pharmaceutically acceptable carrier. In one embodiment, the single crystalline form in (a) is any percentage between 90% and 100% pure.

Also provided are methods of treating an advanced solid tumor, for example, a glioma, melanoma, chondrosarcoma, or cholangiocarcinoma (e.g., glioma), or treating angioimmunoblastic T-cell lymphoma (AITL), each characterized by the presence of a mutant allele of IDH2, comprising administering to subject in need thereof (a) a single crystalline form of compound 1 or compound 2, or (b) a pharmaceutical composition comprising (a) and a pharmaceutically acceptable carrier. In one embodiment, the single crystalline form in (a) is any percentage between 90% and 100% pure.

Provided herein is an assortment of characterizing information to describe the crystalline forms of compound 1 and compound 2. It should be understood, however, that not all such information is required for one skilled in the art to determine that such particular form is present in a given composition, but that the determination of a particular form can be achieved using any portion of the characterizing information that one skilled in the art would recognize as sufficient for establishing the presence of a particular form, e.g., even a single distinguishing peak can be sufficient for one skilled in the art to appreciate that such particular form is present.

Crystalline forms of compound 2 have physical properties that are suitable for large scale pharmaceutical formulation manufacture. Many of the crystalline forms of compound 2 described herein exhibit high crystallinity, high melting point, and limited occluded or solvated solvent. Crystalline forms of compound 2 have improved bioavailability as compared to amorphous forms of compound 2. In particular, Form 3 is non-hygroscopic, and exhibits stability advantages (e.g., thermodynamic, chemical, or physical stability) at a relative humidity of up to 40% at room temperature for at least 3 months.

In one embodiment, at least a particular percentage by weight of compound 1 is crystalline. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. When a particular percentage by weight of compound 1 is crystalline, the remainder of compound 1 is the amorphous form of compound 1. Non-limiting examples of crystalline compound 1 include a single crystalline form of compound 1 or a mixture of different single crystalline forms. In some embodiments, compound 1 is at least 90% by weight crystalline. In some other embodiments, compound 1 is at least 95% by weight crystalline.

In another embodiment, a particular percentage by weight of the crystalline compound 1 is a specific single crystalline form or a combination of single crystalline forms. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In another embodiment, compound 1 is at least 90% by weight of a single crystalline form. In another embodiment, compound 1 is at least 95% by weight of a single crystalline form.

In one embodiment, at least a particular percentage by weight of compound 2 is crystalline. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. When a particular percentage by weight of compound 2 is crystalline, the remainder of compound 2 is the amorphous form of compound 2. Non-limiting examples of crystalline compound 2 include a single crystalline form of compound 2 or a mixture of different single crystalline forms. In some embodiments, compound 2 is at least 90% by weight crystalline. In some other embodiments, compound 2 is at least 95% by weight crystalline.

In another embodiment, a particular percentage by weight of the crystalline compound 2 is a specific single crystalline form or a combination of single crystalline forms. Particular weight percentages may be 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5%, 99.9%, or any percentage between 10% and 100%. In another embodiment, compound 2 is at least 90% by weight of a single crystalline form. In another embodiment, compound 2 is at least 95% by weight of a single crystalline form.

In the following description of compound 1, embodiments of the invention may be described with reference to a particular crystalline form of compound 1, as characterized by one or more properties as discussed herein. The descriptions characterizing the crystalline forms may also be used to describe the mixture of different crystalline forms that may be present in a crystalline compound 1. However, the particular crystalline forms of compound 1 may also be characterized by one or more of the characteristics of the crystalline form as described herein, with or without regard to referencing a particular crystalline form.

In the following description of compound 2, embodiments of the invention may be described with reference to a particular crystalline form of compound 2, as characterized by one or more properties as discussed herein. The descriptions characterizing the crystalline forms may also be used to describe the mixture of different crystalline forms that may be present in a crystalline compound 2. However, the particular crystalline forms of compound 2 may also be characterized by one or more of the characteristics of the crystalline form as described herein, with or without regard to referencing a particular crystalline form.

The crystalline forms are further illustrated by the detailed descriptions and illustrative examples given below. The XRPD peaks described in Tables 1A to 19A may vary by ±0.2° depending upon the instrument used to obtain the data. The intensity of the XRPD peaks described in Tables 1A to 19A may vary by 10%.

Form 1

In one embodiment, a single crystalline form, Form 1, of the compound 1 is characterized by the X-ray powder diffraction (XRPD) pattern shown in FIG. 1, and data shown in Table 1, obtained using CuKa radiation. In a particular embodiment, the polymorph can be characterized by one or more of the peaks taken from FIG. 1, as shown in Table 1A. For example, the polymorph can be characterized by one or two or three or four or five or six or seven or eight or nine of the peaks shown in Table 1A.

TABLE 1A

| Angle 2-Theta° | Intensity % |
|---|---|
| 6.7 | 42.2 |
| 8.9 | 61.8 |
| 9.1 | 41.9 |
| 13.0 | 46.7 |
| 16.4 | 33.2 |
| 18.9 | 100.0 |
| 21.4 | 27.3 |
| 23.8 | 49.2 |
| 28.1 | 47.5 |

In another embodiment, Form 1 can be characterized by the peaks identified at 2θ angles of 8.9, 13.0, 18.9, 23.8, and 28.10. In another embodiment, Form 1 can be characterized by the peaks identified at 2θ angles of 8.9, 18.9, and 24.8°.

Form 2

Figure 2:
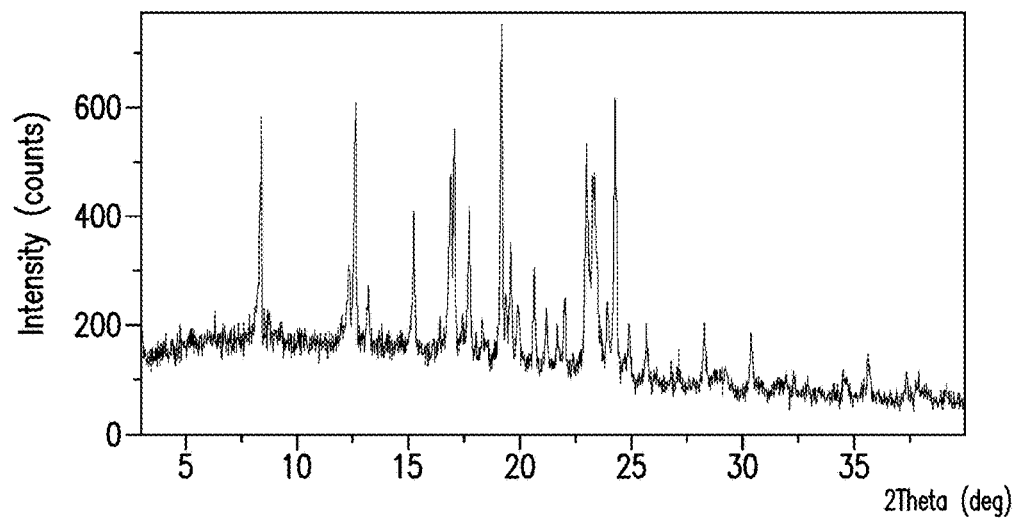
FIG. 2 is an X-ray powder diffractogram (XRPD) of compound 1 Form 2.

In one embodiment, a single crystalline form, Form 2, of the compound 1 is characterized by the X-ray powder diffraction (XRPD) pattern shown in FIG. 2, and data shown in Table 2A, obtained using CuKa radiation. In a particular embodiment, the polymorph can be characterized by one or more of the peaks taken from FIG. 2, as shown in Table 2A. For example, the polymorph can be characterized by one or two or three or four or five or six or seven or eight or nine of the peaks shown in Table 2A.

TABLE 2A

| Angle 2-Theta° | Intensity % |
|---|---|
| 8.4 | 65.2 |
| 12.7 | 75.5 |
| 16.9 | 57.9 |
| 17.1 | 69.4 |
| 17.7 | 48.6 |
| 19.2 | 100.0 |
| 23.0 | 69.7 |
| 23.3 | 61.1 |
| 24.2 | 87.3 |

In another embodiment, Form 2 can be characterized by the peaks identified at 2θ angles of 12.7, 17.1, 19.2, 23.0, and 24.2°. In another embodiment, Form 2 can be characterized by the peaks identified at 2θangles of 12.7, 19.2, and 24.2°.

Figure 3:
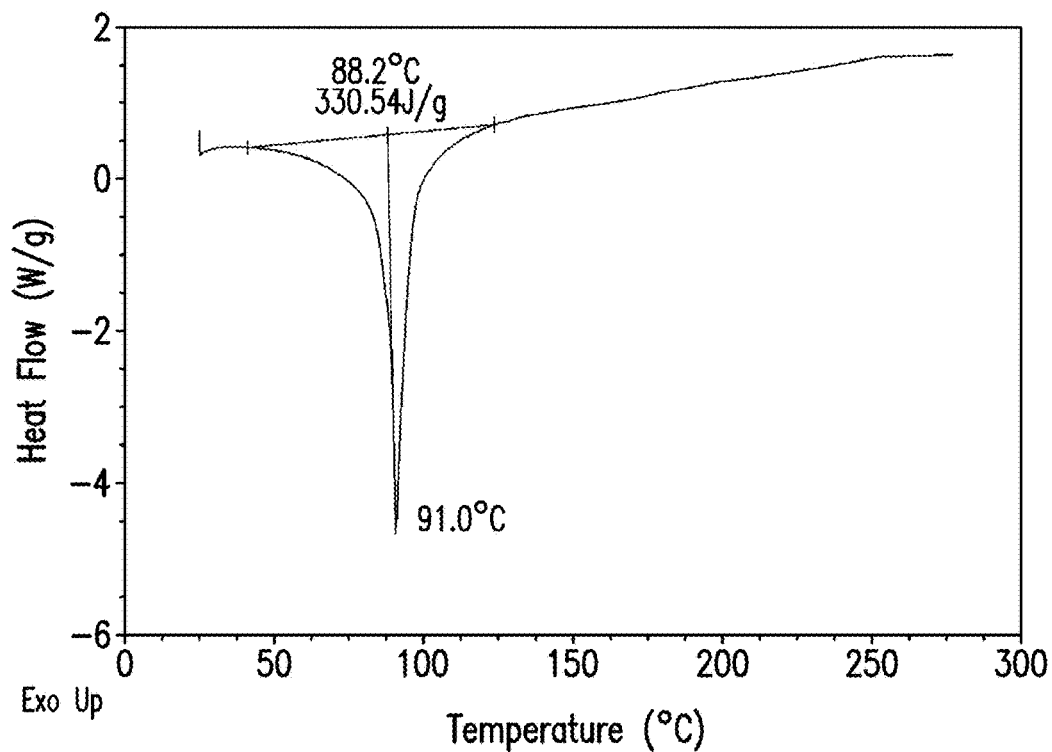
FIG. 3 is a differential scanning calorimetry (DSC) profile of compound 1 Form 2.

In another embodiment, Form 2 can be characterized by the differential scanning calorimetry profile (DSC) shown in FIG. 3. The DSC graph plots the heat flow as a function of temperature from a sample, the temperature rate change being about 10° C./min. The profile is characterized by a strong endothermic transition with an onset temperature of about 88.2° C. with a melt at about 91.0° C.

Figure 4:
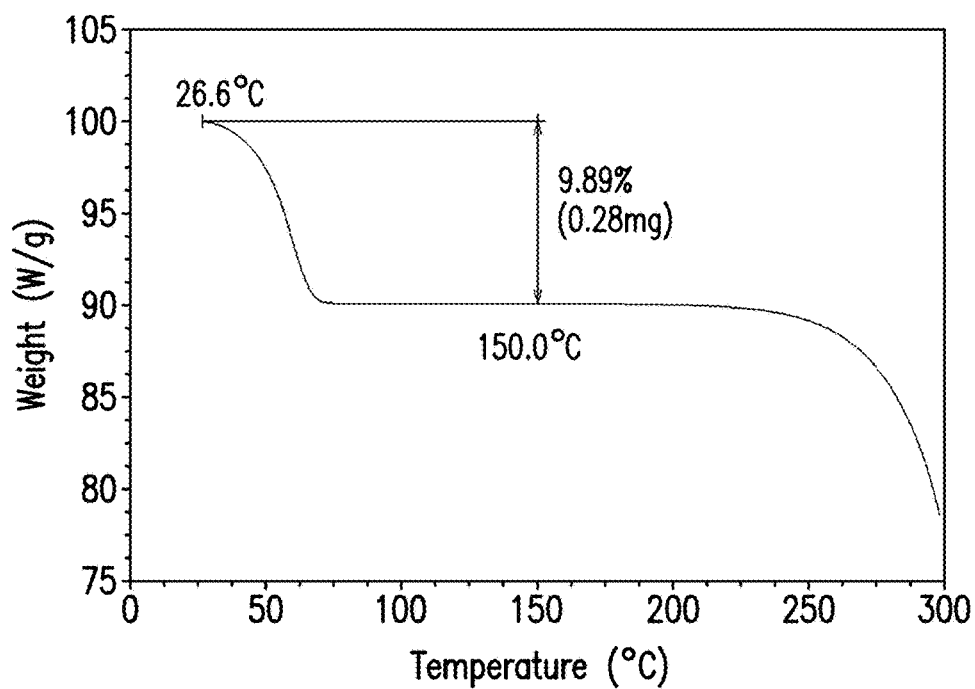
FIG. 4 is a thermal gravimetric analysis (TGA) profile of compound 1 Form 2.

In another embodiment, Form 2 can be characterized by thermal gravimetric analysis (TGA) shown in FIG. 4. The TGA profile graphs the percent loss of weight of the sample as a function of temperature, the temperature rate change being about 10° C./min. The weight loss represents a loss of about 9.9% of the weight of the sample as the temperature is changed from about 26.6° C. to 150.0° C.

Form 3

Figure 5:
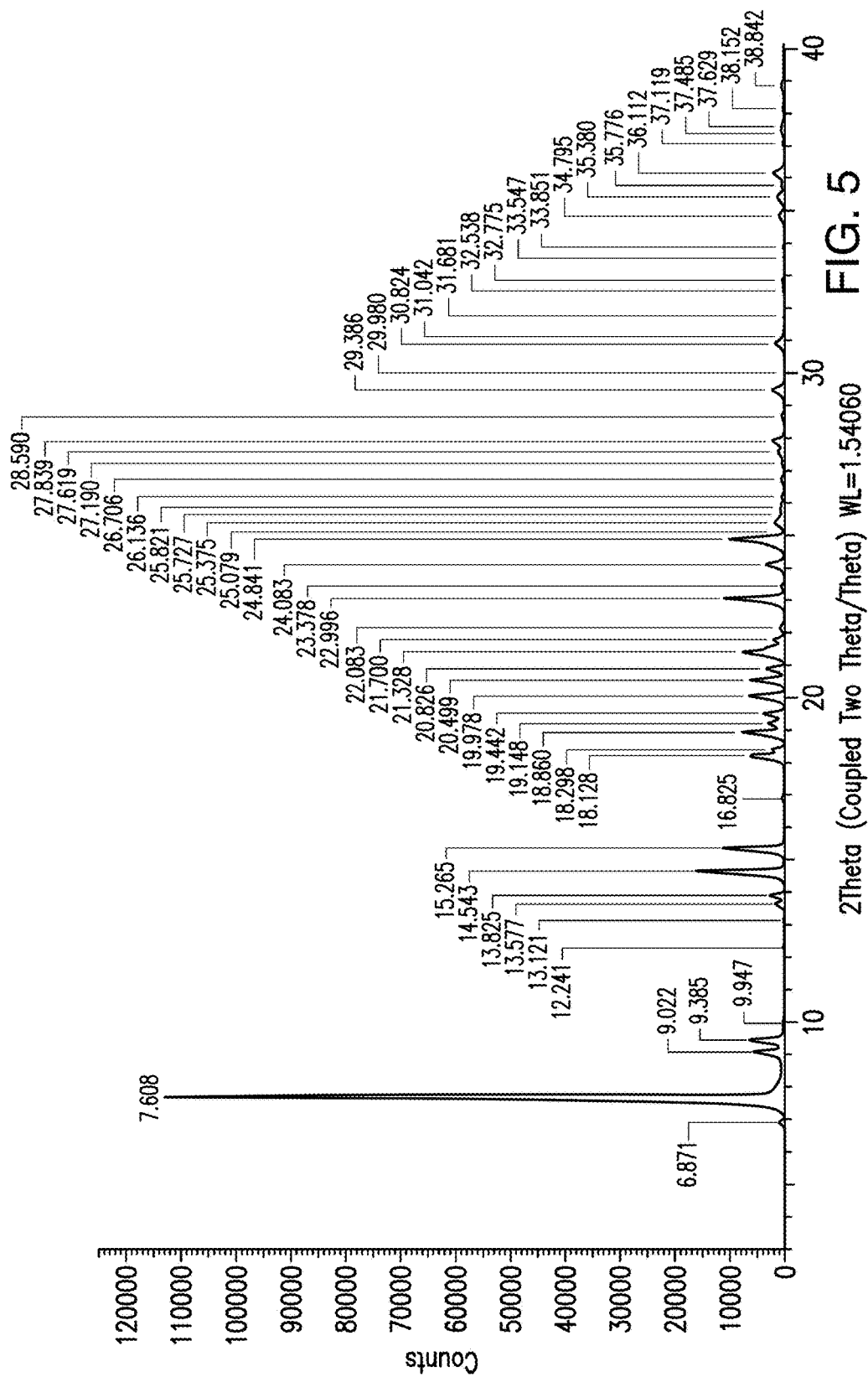
FIG. 5 is an X-ray powder diffractogram (XRPD) of compound 2 Form 3.

In one embodiment, a single crystalline form, Form 3, of the compound 2 is characterized by the X-ray powder diffraction (XRPD) pattern shown in FIG. 5, and data shown in Table 3A, obtained using CuKa radiation. In a particular embodiment, the polymorph can be characterized by one or more of the peaks taken from FIG. 5, as shown in Table 3A. For example, the polymorph can be characterized by one or two or three or four or five or six or seven or eight or nine or ten of the peaks shown in Table 3A.

TABLE 3A

| Angle 2-Theta° | Intensity % |
|---|---|
| 7.5 | 100.0 |
| 9.0 | 16.5 |
| 9.3 | 27.2 |
| 14.5 | 48.5 |
| 15.2 | 17.2 |
| 18.0 | 17.0 |
| 18.8 | 32.6 |

TABLE 3A-continued

| Angle 2-Theta° | Intensity % |
| --- | --- |
| 19.9 | 18.7 |
| 21.3 | 19.3 |
| 24.8 | 33.8 |

In another embodiment, Form 3 can be characterized by the peaks identified at 2θangles of 7.5, 9.3, 14.5, 18.8, 21.3, and 24.8°. In a further embodiment, Form 3 can be characterized by the peaks are identified at 2θangles of 7.5, 14.5, 18.8, and 24.8°. In another, embodiment, Form 3 can be characterized by the peaks identified at 2θangles of 7.5, 14.5, and 24.8°.

Figure 6:
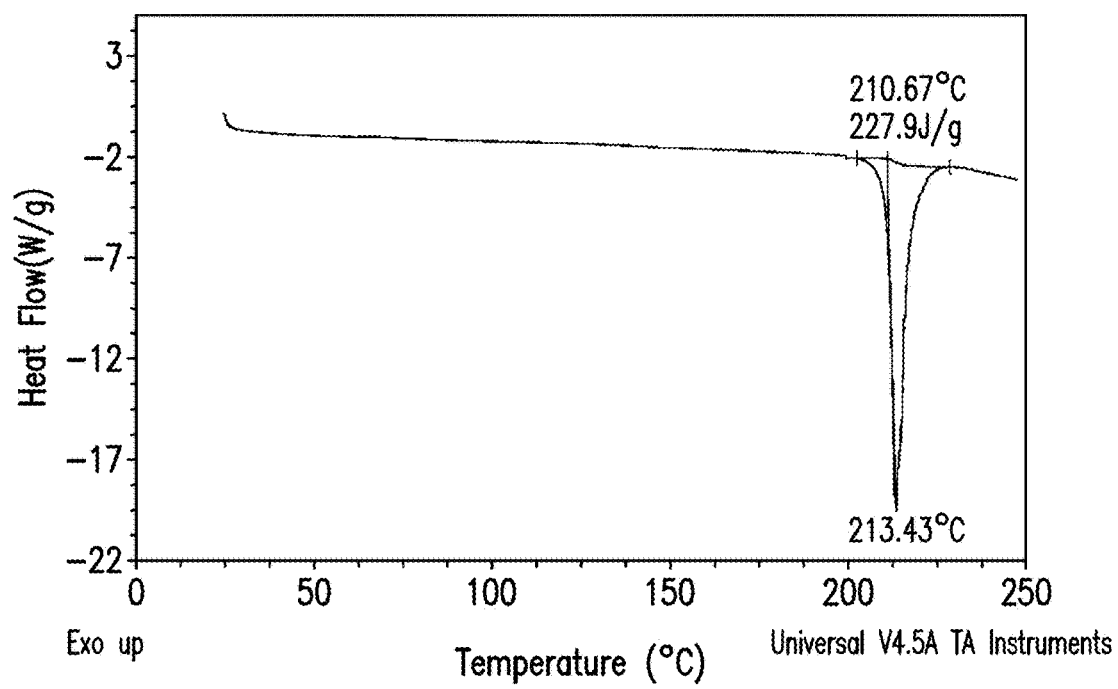
FIG. 6 is a differential scanning calorimetry (DSC) profile of compound 2 Form 3.

In another embodiment, Form 3 can be characterized by the differential scanning calorimetry profile (DSC) shown in FIG. 6. The DSC graph plots the heat flow as a function of temperature from a sample, the temperature rate change being about 10° C./min. The profile is characterized by a strong endothermic transition with an onset temperature of about 210.7° C. with a melt at about 213.4° C.

Figure 7:
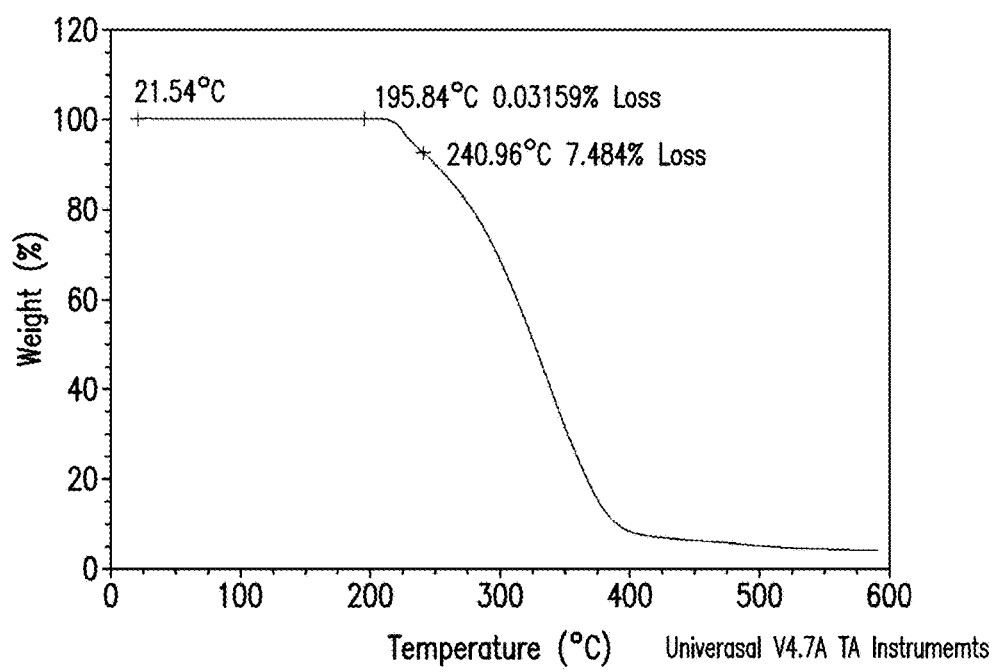
FIG. 7 is a thermal gravimetric analysis (TGA) profile of compound 2 Form 3.
Figure 8:
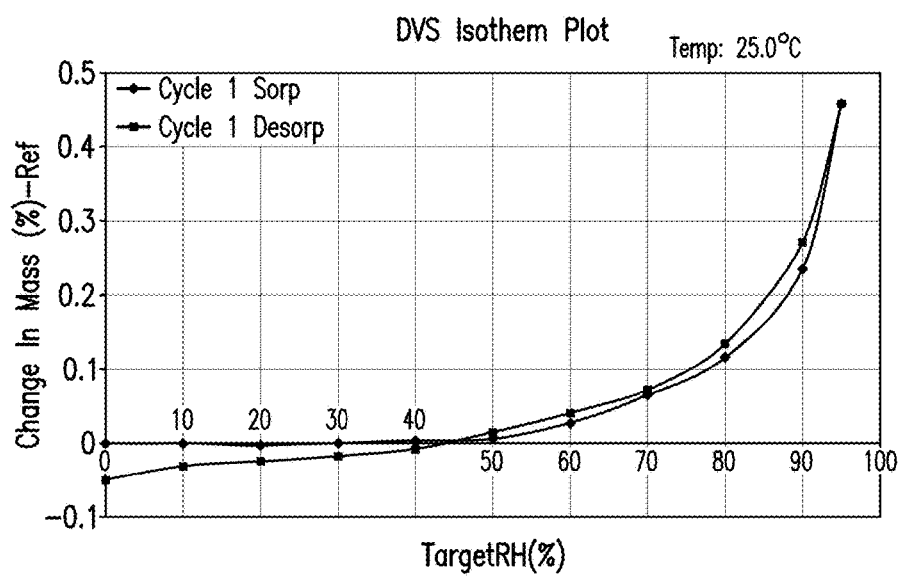
FIG. 8 is a dynamic vapor sorption (DVS) profile of compound 2 Form 3.

In another embodiment, Form 3 can be characterized by thermal gravimetric analysis (TGA) shown in FIG. 7. The TGA profile graphs the percent loss of weight of the sample as a function of temperature, the temperature rate change being about 10° C./min. The weight loss represents a loss of about 0.03% of the weight of the sample as the temperature is changed from about 21° C. to 196° C. and about 7.5% of the weight of the sample as the temperature is changed from about 196° C. to 241° C.

In another embodiment, Form 3 is characterized by an X-ray powder diffraction pattern substantially similar to FIG. 5. In another embodiment, Form 3 is characterized by a differential scanning calorimetry (DSC) profile substantially similar to FIG. 6. In another embodiment, Form 3 is characterized by a thermal gravimetric analysis (TGA) profile substantially similar to FIG. 7. In further embodiments, a single crystalline form of Form 3 is characterized by one or more of the features listed in this paragraph. In another embodiment, Form 3 is characterized by a DVS profile substantially similar to FIG. 8.

Form 4

Figure 9:
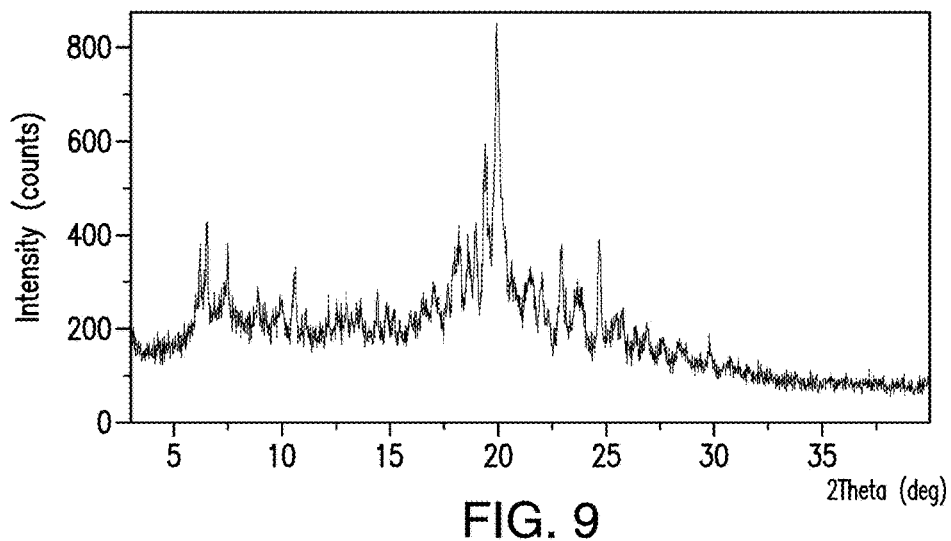
FIG. 9 is an X-ray powder diffractogram (XRPD) of compound 2 Form 4.

In one embodiment, a single crystalline form, Form 4, of the compound 2 is characterized by the X-ray powder diffraction (XRPD) pattern shown in FIG. 9, and data shown in Table 4A, obtained using CuKa radiation. In a particular embodiment, the polymorph can be characterized by one or more of the peaks taken from FIG. 9, as shown in Table 4A. For example, the polymorph can be characterized by one or two or three or four or five or six or seven or eight or nine of the peaks shown in Table 4A.

TABLE 4A

| Angle 2-Theta° | Intensity % |
| --- | --- |
| 6.2 | 28.9 |
| 6.5 | 38.0 |
| 7.5 | 29.5 |
| 18.6 | 25.0 |
| 19.0 | 34.8 |
| 19.4 | 58.8 |
| 19.9 | 100.0 |
| 22.9 | 31.0 |
| 24.7 | 36.9 |

In another embodiment, Form 4 can be characterized by the peaks identified at 2θangles of 6.5, 19.0, 19.4, 19.9, and 24.7°. In a further embodiment, Form 4 can be characterized by the peaks are identified at 2θangles of 6.5, 19.4, and 19.9°.

Figure 10:
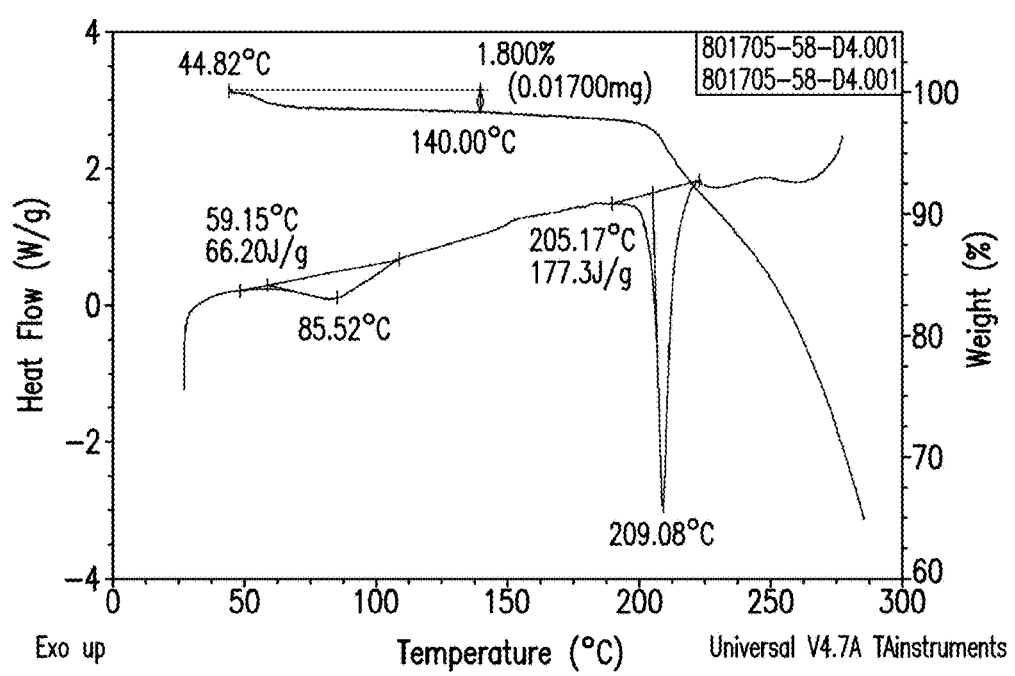
FIG. 10 is a differential scanning calorimetry (DSC) and thermal gravimetric analysis (TGA) profile of compound 2 Form 4.

In another embodiment, Form 4 can be characterized by the differential scanning calorimetry profile (DSC) shown in FIG. 10. The DSC graph plots the heat flow as a function of temperature from a sample, the temperature rate change being about 10° C./min. The profile is characterized by a weak endothermic transition with an onset temperature of about 59.2° C. with a melt at about 85.5° C. and a strong endothermic transition with an onset temperature of about 205.2° C. with a melt at about 209.1° C.

In another embodiment, Form 4 can be characterized by thermal gravimetric analysis (TGA) shown in FIG. 10. The TGA profile graphs the percent loss of weight of the sample as a function of temperature, the temperature rate change being about 10° C./min. The weight loss represents a loss of about 1.8% of the weight of the sample as the temperature is changed from about 44.8° C. to 140.0° C.

Form 5

Figure 11:
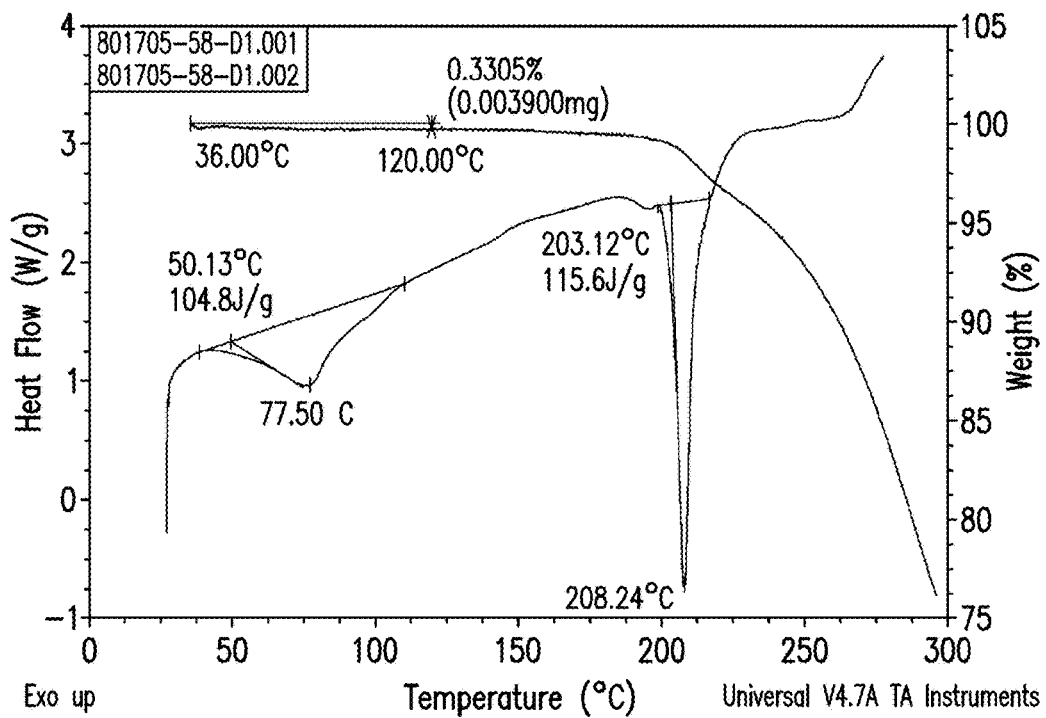
FIG. 11 is an X-ray powder diffractogram (XRPD) of compound 2 Form 5.

In one embodiment, a single crystalline form, Form 5, of the compound 2 is characterized by the X-ray powder diffraction (XRPD) pattern shown in FIG. 11, and data shown in Table 5, obtained using CuKa radiation. In a particular embodiment, the polymorph can be characterized by one or more of the peaks taken from FIG. 11, as shown in Table 5A. For example, the polymorph can be characterized by one or two or three or four or five or six or seven or eight or nine of the peaks shown in Table 5A.

TABLE 5A

| Angle 2-Theta° | Intensity % |
| --- | --- |
| 7.1 | 100.0 |
| 14.5 | 40.0 |
| 17.1 | 29.8 |
| 19.2 | 6.1 |
| 21.8 | 47.8 |
| 22.7 | 7.7 |
| 23.4 | 6.5 |
| 28.5 | 2.1 |
| 29.4 | 17.6 |

In one embodiment, Form 5 can be characterized by the peaks identified at 2θangles of 7.1, 14.5, 17.1, and 21.8°. In a further embodiment, Form 5 can be characterized by the peaks are identified at 2θangles of 7.1 and 21.8°.

Figure 12:
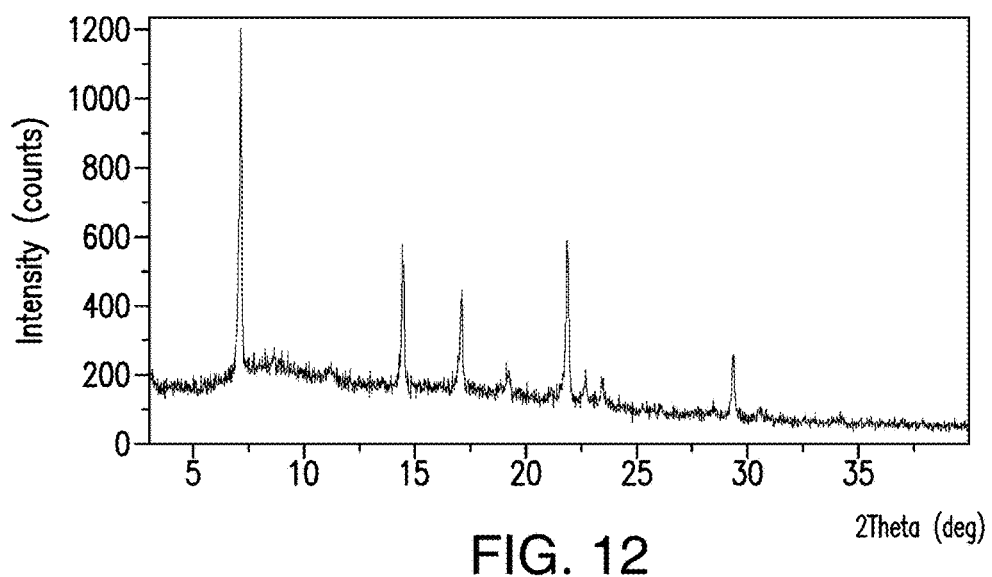
FIG. 12 is a differential scanning calorimetry (DSC) and thermal gravimetric analysis (TGA) profile of compound 2 Form 5.

In another embodiment, Form 5 can be characterized by the differential scanning calorimetry profile (DSC) shown in FIG. 12. The DSC graph plots the heat flow as a function of temperature from a sample, the temperature rate change being about 10° C./min. The profile is characterized by a weak endothermic transition with an onset temperature of about 50.1° C. with a melt at about 77.5° C. and a strong endothermic transition with an onset temperature of about 203.1° C. with a melt at about 208.2° C.

In another embodiment, Form 5 can be characterized by thermal gravimetric analysis (TGA) shown in FIG. 12. The TGA profile graphs the percent loss of weight of the sample as a function of temperature, the temperature rate change being about 10° C./min. The weight loss represents a loss of about 0.3% of the weight of the sample as the temperature is changed from about 36.0° C. to 120.0° C.

Form 6

Figure 13:
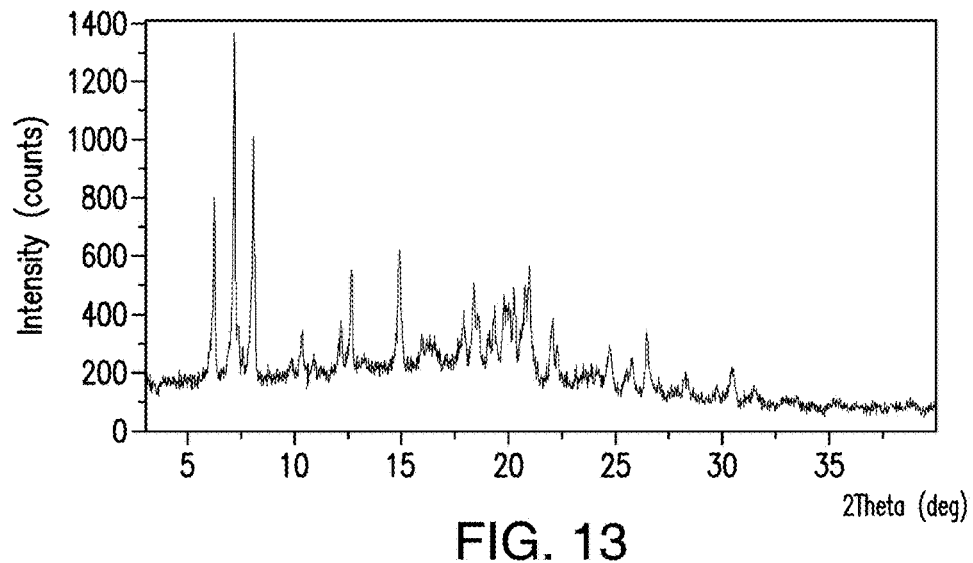
FIG. 13 is an X-ray powder diffractogram (XRPD) of compound 2 Form 6.

In one embodiment, a single crystalline form, Form 6, of the compound 2 is characterized by the X-ray powder diffraction (XRPD) pattern shown in FIG. 13, and data shown in Table 6A, obtained using CuKa radiation. In a particular embodiment, the polymorph can be characterized by one or more of the peaks taken from FIG. 13, as shown in Table 6A. For example, the polymorph can be characterized by one or two or three or four or five or six or seven or eight or nine of the peaks shown in Table 6A.

TABLE 6A

| Angle 2-Theta° | Intensity % |
| --- | --- |
| 6.3 | 53.7 |
| 7.2 | 100.0 |
| 8.1 | 71.5 |
| 12.2 | 19.2 |
| 12.7 | 34.0 |
| 14.9 | 37.2 |
| 17.9 | 21.4 |
| 18.4 | 31.0 |
| 26.4 | 20.2 |

In another embodiment, Form 6 can be characterized by the peaks identified at 2θangles of 6.3, 7.2, 8.1, 12.7, and 14.9°. In a further embodiment, Form 6 can be characterized by the peaks are identified at 2θangles of 6.3, 7.2, and 8.1°.

Figure 14:
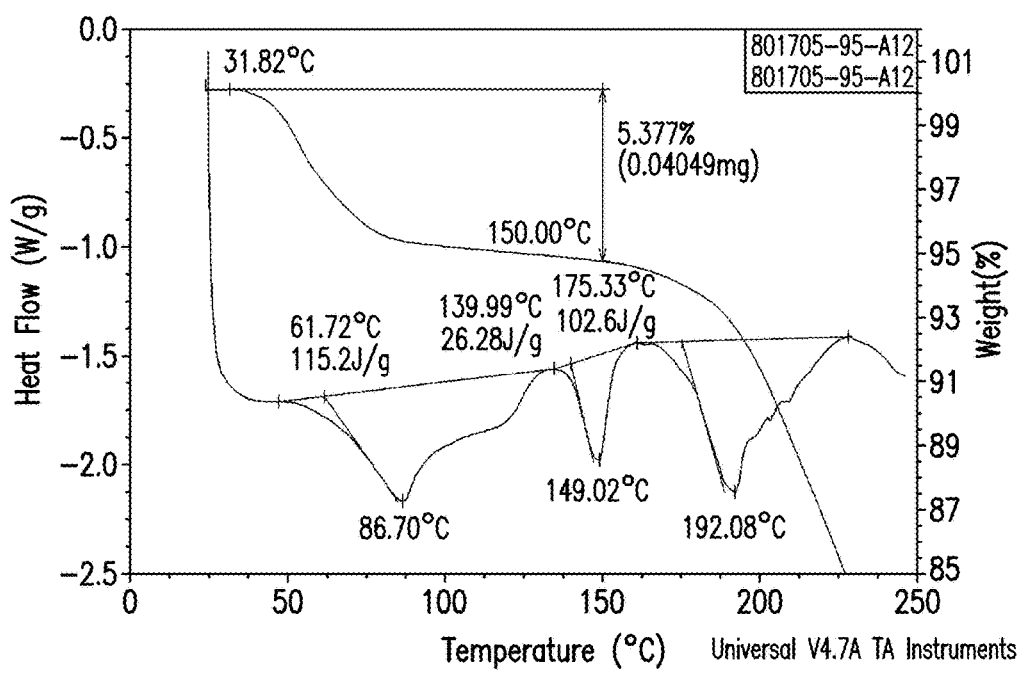
FIG. 14 is a differential scanning calorimetry (DSC) and thermal gravimetric analysis (TGA) profile of compound 2 Form 6.

In another embodiment, Form 6 can be characterized by the differential scanning calorimetry profile (DSC) shown in FIG. 14. The DSC graph plots the heat flow as a function of temperature from a sample, the temperature rate change being about 10° C./min. The profile is characterized by three weak endothermic transitions: with an onset temperature of about 61.7° C. with a melt at about 86.75° C., an onset temperature of about 140.0° C. with a melt at about 149.0° C., and an onset temperature of about 175.3° C. with a melt at about 192.1° C.

In another embodiment, Form 6 can be characterized by thermal gravimetric analysis (TGA) shown in FIG. 14. The TGA profile graphs the percent loss of weight of the sample as a function of temperature, the temperature rate change being about 10° C./min. The weight loss represents a loss of about 5.4% of the weight of the sample as the temperature is changed from about 31.8° C. to 150.0° C.

Form 7

Figure 15:
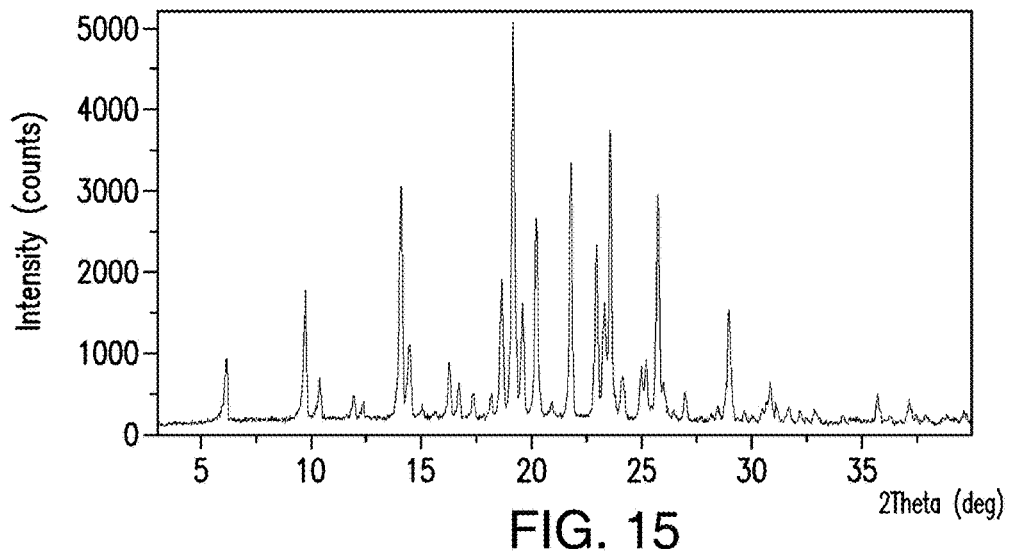
FIG. 15 is an X-ray powder diffractogram (XRPD) of compound 2 Form 7.

In one embodiment, a single crystalline form, Form 7, of the compound 2 is characterized by the X-ray powder diffraction (XRPD) pattern shown in FIG. 15, and data shown in Table 7A, obtained using CuKa radiation. In a particular embodiment, the polymorph can be characterized by one or more of the peaks taken from FIG. 15, as shown in Table 7A. For example, the polymorph can be characterized by one or two or three or four or five or six or seven or eight or nine of the peaks shown in Table 7A.

TABLE 7A

| Angle 2-Theta° | Intensity % |
| --- | --- |
| 9.7 | 32.5 |
| 14.1 | 59.0 |
| 18.6 | 35.7 |
| 19.1 | 100.0 |
| 20.2 | 50.6 |
| 21.8 | 65.9 |
| 23.5 | 72.4 |
| 25.7 | 57.7 |
| 28.9 | 27.7 |

In another embodiment, Form 7 can be characterized by the peaks identified at 2θangles of 14.1, 19.1, 21.8, 23.5, and 25.7°. In a further embodiment, Form 7 can be characterized by the peaks are identified at 2θangles of 19.1, 21.8, and 23.5°.

Figure 16:
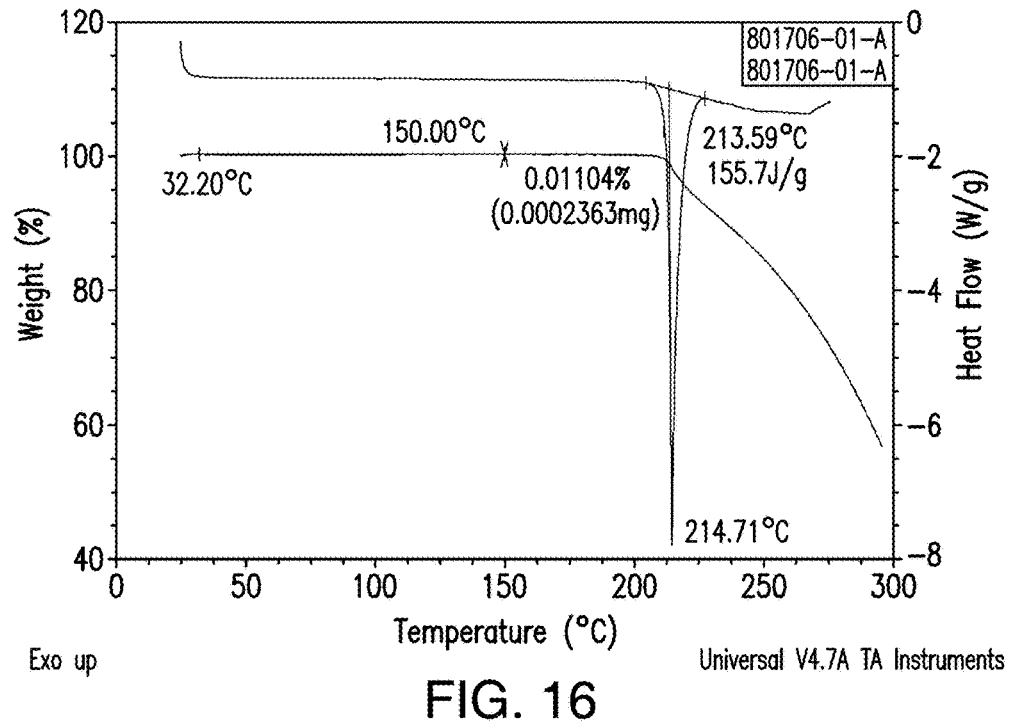
FIG. 16 is a differential scanning calorimetry (DSC) and thermal gravimetric analysis (TGA) profile of compound 2 Form 7.

In another embodiment, Form 7 can be characterized by the differential scanning calorimetry profile (DSC) shown in FIG. 16. The DSC graph plots the heat flow as a function of temperature from a sample, the temperature rate change being about 10° C./min. The profile is characterized by a strong endothermic transition with an onset temperature of about 213.6° C. with a melt at about 214.7° C.

In another embodiment, Form 7 can be characterized by thermal gravimetric analysis (TGA) shown in FIG. 16. The TGA profile graphs the percent loss of weight of the sample as a function of temperature, the temperature rate change being about 10° C./min. The weight loss represents a loss of about 0.01% of the weight of the sample as the temperature is changed from about 32.2° C. to 150.0° C.

Form 8

Figure 17:
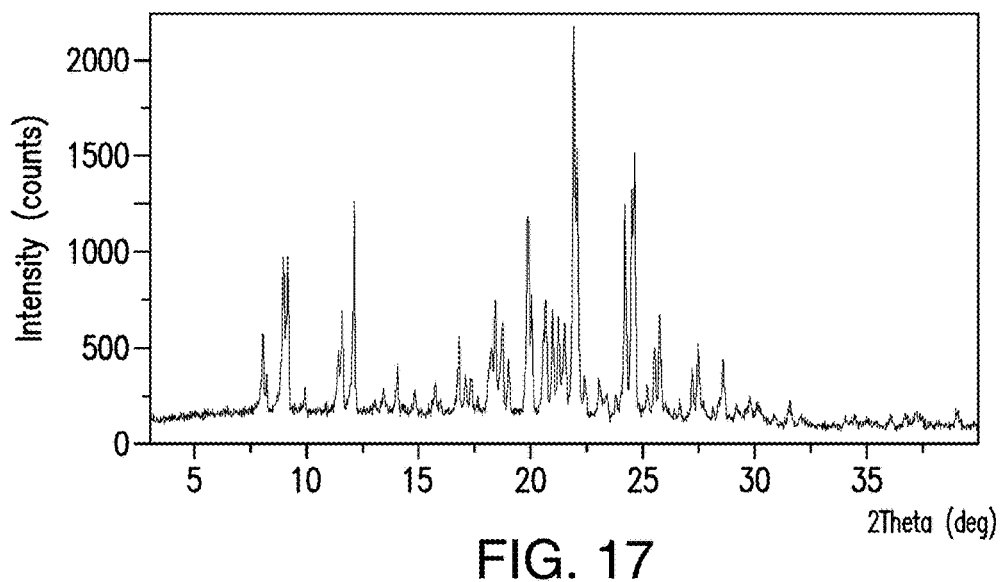
FIG. 17 is a X-ray powder diffractogram (XRPD) of compound 2 Form 8.

In one embodiment, a single crystalline form, Form 8, of the compound 2 is characterized by the X-ray powder diffraction (XRPD) pattern shown in FIG. 17, and data shown in Table 8A, obtained using CuKa radiation. In a particular embodiment, the polymorph can be characterized by one or more of the peaks taken from FIG. 17, as shown in Table 8A. For example, the polymorph can be characterized by one or two or three or four or five or six or seven or eight or nine of the peaks shown in Table 8A.

TABLE 8A

| Angle 2-Theta° | Intensity % |
| --- | --- |
| 9.0 | 38.7 |
| 9.2 | 39.6 |
| 14.1 | 12.0 |
| 16.8 | 21.9 |
| 19.9 | 53.4 |
| 21.9 | 100.0 |
| 22.1 | 65.9 |
| 24.2 | 56.6 |
| 24.6 | 66.7 |

In another embodiment, Form 8 can be characterized by the peaks identified at 2θangles of 9.0, 9.2, 21.9, 22.1, 24.2, and 24.6°. In a further embodiment, Form 8 can be characterized by the peaks are identified at 2θangles of 21.9, 22.1, 24.2, and 24.6°.

Figure 18:
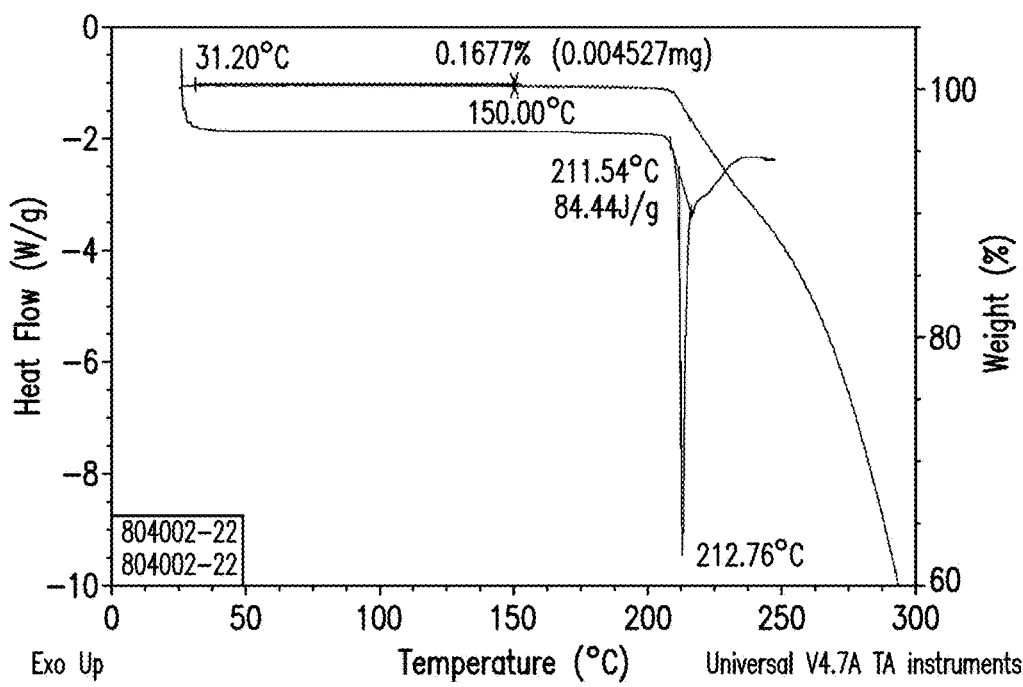
FIG. 18 is a differential scanning calorimetry (DSC) and thermal gravimetric analysis (TGA) profile of compound 2 Form 8.

In another embodiment, Form 8 can be characterized by the differential scanning calorimetry profile (DSC) shown in FIG. 18. The DSC graph plots the heat flow as a function of temperature from a sample, the temperature rate change being about 10° C./min. The profile is characterized by a strong endothermic transition with an onset temperature of about 211.5° C. with a melt at about 212.8° C.

In another embodiment, Form 8 can be characterized by thermal gravimetric analysis (TGA) shown in FIG. 18. The TGA profile graphs the percent loss of weight of the sample as a function of temperature, the temperature rate change being about 10° C./min. The weight loss represents a loss of about 0.2% of the weight of the sample as the temperature is changed from about 31.2° C. to 150.0° C.

Form 9

Figure 19:
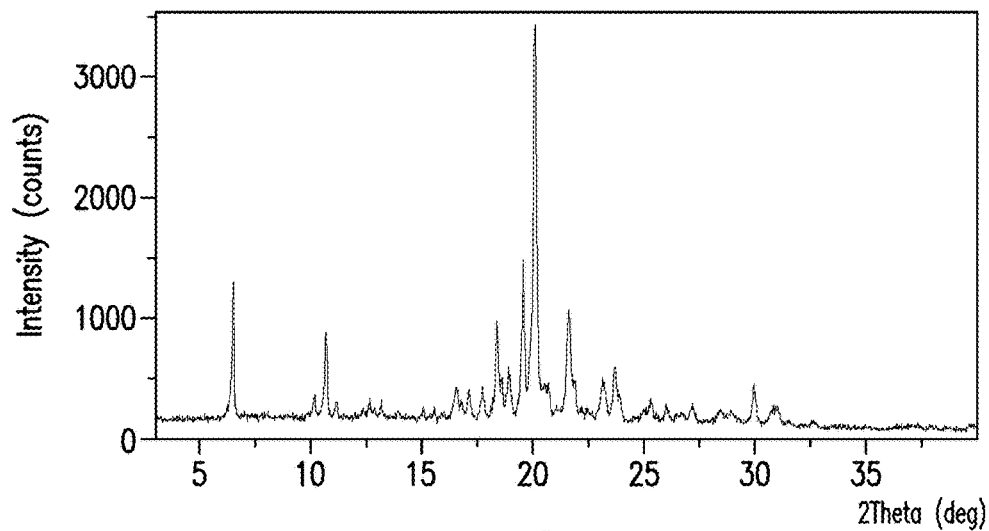
FIG. 19 is an X-ray powder diffractogram (XRPD) of compound 2 Form 9.

In one embodiment, a single crystalline form, Form 9, of the compound 2 is characterized by the X-ray powder diffraction (XRPD) pattern shown in FIG. 19, and data shown in Table 9A, obtained using CuKa radiation. In a particular embodiment, the polymorph can be characterized by one or more of the peaks taken from FIG. 19, as shown in Table 9A. For example, the polymorph can be characterized by one or two or three or four or five or six or seven or eight or nine of the peaks shown in Table 9A.

TABLE 9A

| Angle 2-Theta° | Intensity % |
|---|---|
| 6.5 | 33.8 |
| 10.7 | 21.8 |
| 17.7 | 8.6 |
| 18.4 | 23.7 |
| 19.0 | 13.6 |
| 19.6 | 40.1 |
| 20.1 | 100.0 |
| 21.6 | 26.9 |
| 29.9 | 9.9 |

In another embodiment, Form 9 can be characterized by the peaks identified at 2θangles of 6.5, 19.6, 20.1, and 21.6°. In a further embodiment, Form 9 can be characterized by the peaks are identified at 2θangles of 19.6 and 20.1°.

Figure 20:
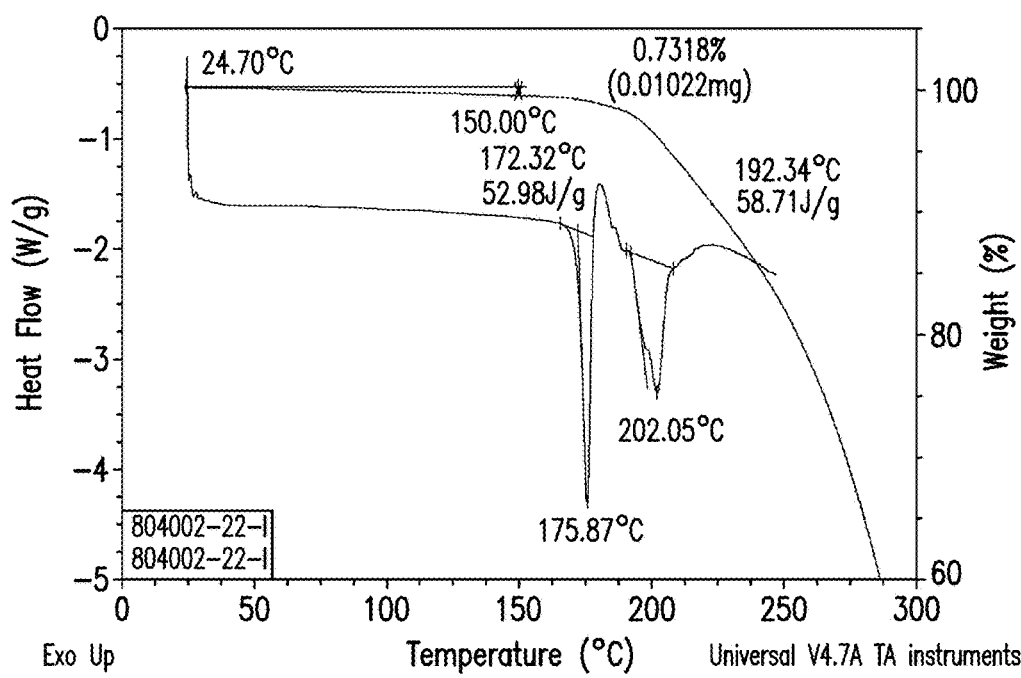
FIG. 20 is a differential scanning calorimetry (DSC) and thermal gravimetric analysis (TGA) profile of compound 2 Form 9.

In another embodiment, Form 9 can be characterized by the differential scanning calorimetry profile (DSC) shown in FIG. 20. The DSC graph plots the heat flow as a function of temperature from a sample, the temperature rate change being about 10° C./min. The profile is characterized by a strong endothermic transition with an onset temperature of about 172.3° C. with a melt at about 175.95° C. and an endothermic transition with an onset temperature of about 192.3° C. with a melt at about 202.1° C.

In another embodiment, Form 9 can be characterized by thermal gravimetric analysis (TGA) shown in FIG. 20. The TGA profile graphs the percent loss of weight of the sample as a function of temperature, the temperature rate change being about 10° C./min. The weight loss represents a loss of about 0.7% of the weight of the sample as the temperature is changed from about 24.7° C. to 150.0° C.

Form 10

Figure 21:
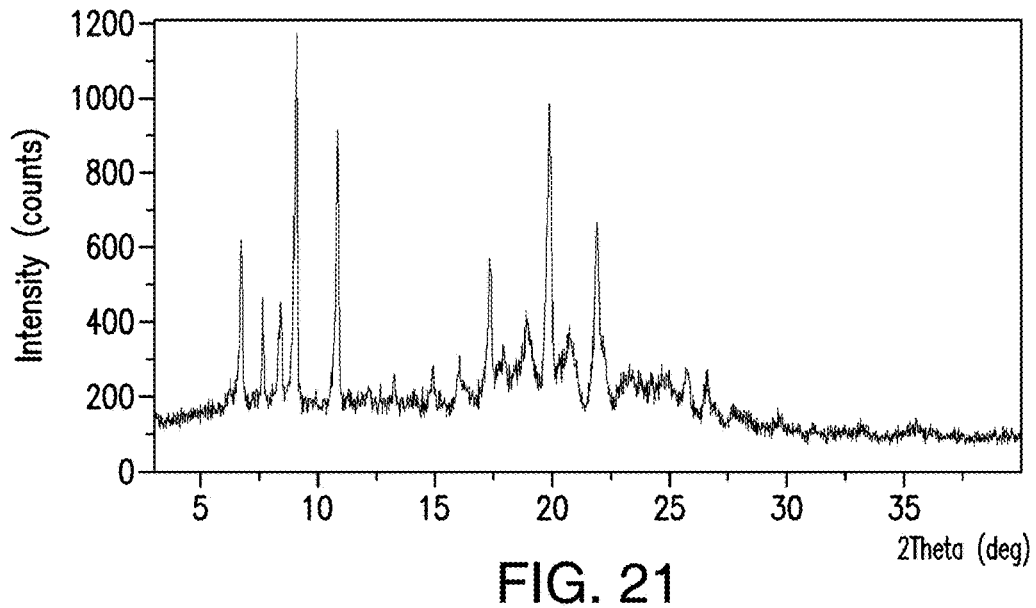
FIG. 21 is an X-ray powder diffractogram (XRPD) of compound 2 Form 10.

In one embodiment, a single crystalline form, Form 10, of the compound 2 is characterized by the X-ray powder diffraction (XRPD) pattern shown in FIG. 21, and data shown in Table 10A, obtained using CuKa radiation. In a particular embodiment, the polymorph can be characterized by one or more of the peaks taken from FIG. 21, as shown in Table 10A. For example, the polymorph can be characterized by one or two or three or four or five or six or seven or eight or nine of the peaks shown in Table 10A.

TABLE 10A

| Angle 2-Theta° | Intensity % |
|---|---|
| 6.7 | 46.8 |
| 7.7 | 31.0 |
| 9.1 | 100.0 |
| 10.8 | 76.9 |
| 13.3 | 11.6 |
| 16.0 | 15.6 |
| 19.9 | 84.6 |
| 21.9 | 52.3 |
| 25.8 | 15.2 |

In another embodiment, Form 10 can be characterized by the peaks identified at 2θangles of 6.7, 9.1, 10.8, 19.9, and 21.9°. In a further embodiment, Form 10 can be characterized by the peaks are identified at 2θangles of 9.1, 10.8, and 19.9°.

Figure 22:
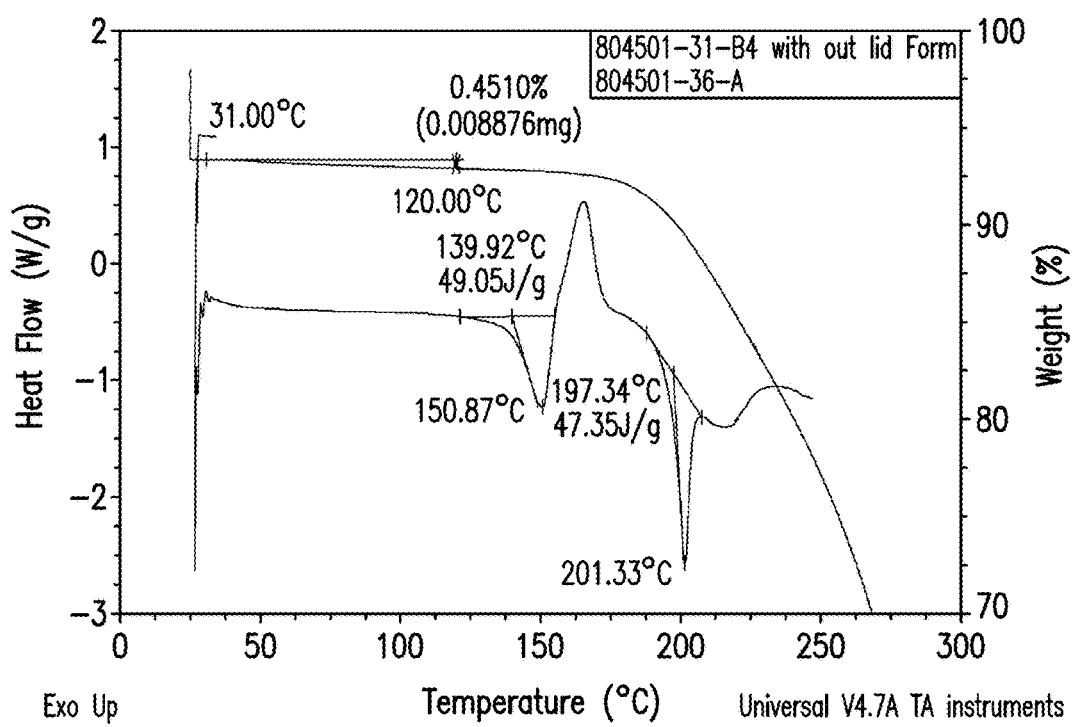
FIG. 22 is a differential scanning calorimetry (DSC) and thermal gravimetric analysis (TGA) profile of compound 2 Form 10.

In another embodiment, Form 10 can be characterized by the differential scanning calorimetry profile (DSC) shown in FIG. 22. The DSC graph plots the heat flow as a function of temperature from a sample, the temperature rate change being about 10° C./min. The profile is characterized by an endothermic transition with an onset temperature of about 139.9° C. with a melt at about 150.9° C. and an endothermic transition with an onset temperature of about 197.3° C. with a melt at about 201.3° C.

In another embodiment, Form 10 can be characterized by thermal gravimetric analysis (TGA) shown in FIG. 22. The TGA profile graphs the percent loss of weight of the sample as a function of temperature, the temperature rate change being about 10° C./min. The weight loss represents a loss of about 0.5% of the weight of the sample as the temperature is changed from about 31.0° C. to 120.0° C.

Form 11

Figure 23:
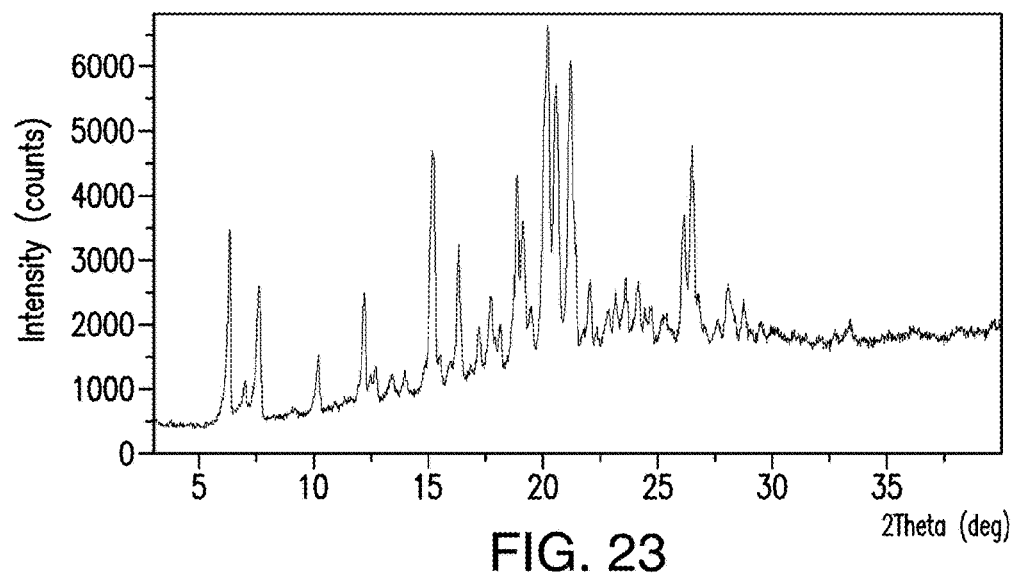
FIG. 23 is an X-ray powder diffractogram (XRPD) of compound 2 Form 11.

In one embodiment, a single crystalline form, Form 11, of the compound 2 is characterized by the X-ray powder diffraction (XRPD) pattern shown in FIG. 23, and data shown in Table 11A, obtained using CuKa radiation. In a particular embodiment, the polymorph can be characterized by one or more of the peaks taken from FIG. 23, as shown in Table 11A. For example, the polymorph can be characterized by one or two or three or four or five or six or seven or eight or nine or ten or eleven of the peaks shown in Table 11A.

TABLE 11A

| Angle 2-Theta° | Intensity % |
|---|---|
| 6.3 | 53.1 |
| 7.7 | 32.8 |
| 16.3 | 40.2 |
| 17.2 | 16.8 |
| 20.0 | 74.6 |
| 20.2 | 100.0 |
| 20.5 | 79.2 |
| 21.2 | 89.4 |
| 23.2 | 21.4 |
| 26.5 | 56.0 |
| 28.1 | 17.2 |

In another embodiment, Form 11 can be characterized by the peaks identified at 2θangles of 6.3, 20.0, 20.2, 20.5, 21.2, and 26.5°. In a further embodiment, Form 11 can be characterized by the peaks are identified at 2θangles of 20.0, 20.2, 20.5, and 21.2°.

Figure 24:
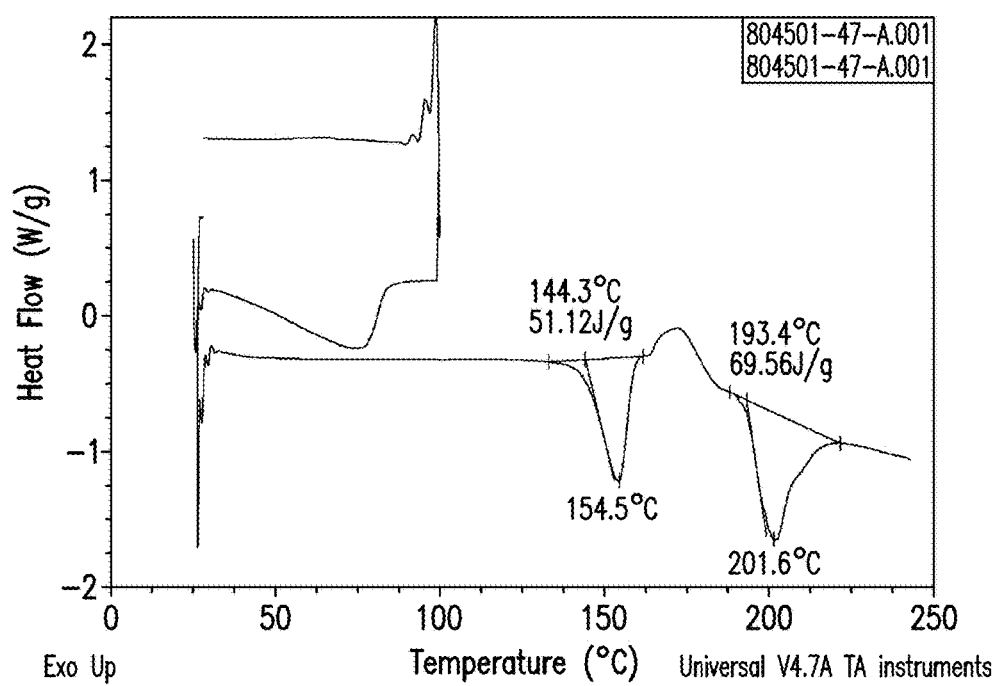
FIG. 24 is a differential scanning calorimetry (DSC) profile of compound 2 Form 11.

In another embodiment, Form 11 can be characterized by the differential scanning calorimetry profile (DSC) shown in FIG. 24. The DSC graph plots the heat flow as a function of temperature from a sample, the temperature rate change being about 10° C./min. The profile is characterized by an endothermic transition with an onset temperature of about 144.3° C. with a melt at about 154.5° C. and an endothermic transition with an onset temperature of about 193.4° C. with a melt at about 201.6° C.

Figure 25:
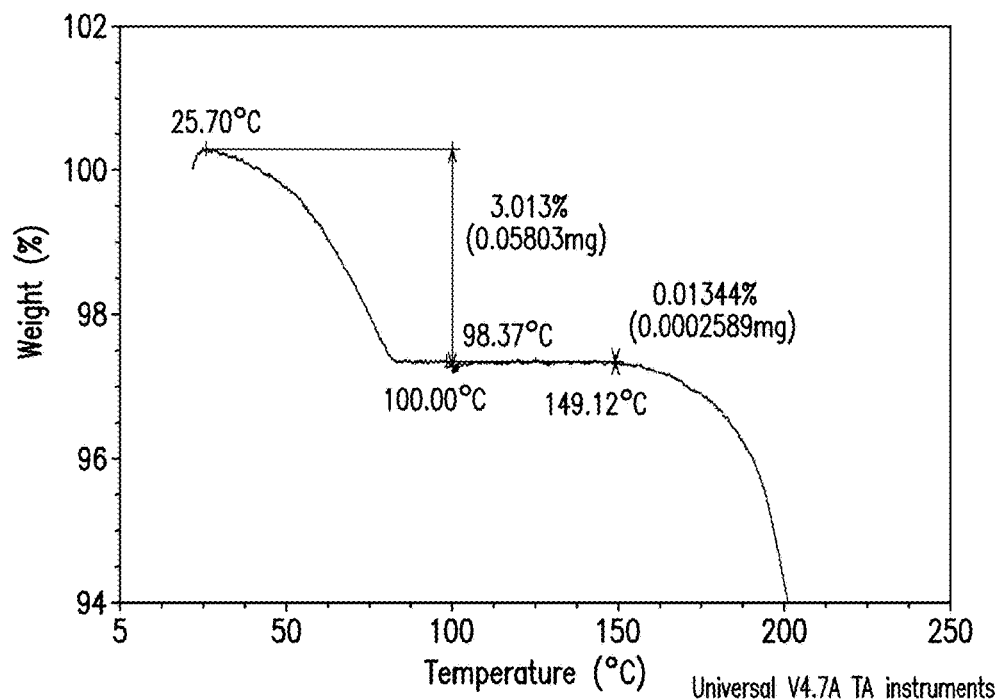
FIG. 25 is a thermal gravimetric analysis (TGA) profile of compound 2 Form 11.

In another embodiment, Form 11 can be characterized by thermal gravimetric analysis (TGA) shown in FIG. 25. The TGA profile graphs the percent loss of weight of the sample as a function of temperature, the temperature rate change being about 10° C./min. The weight loss represents a loss of about 3.0% of the weight of the sample as the temperature is changed from about 25.7° C. to 98.4° C.

Form 12

Figure 26:
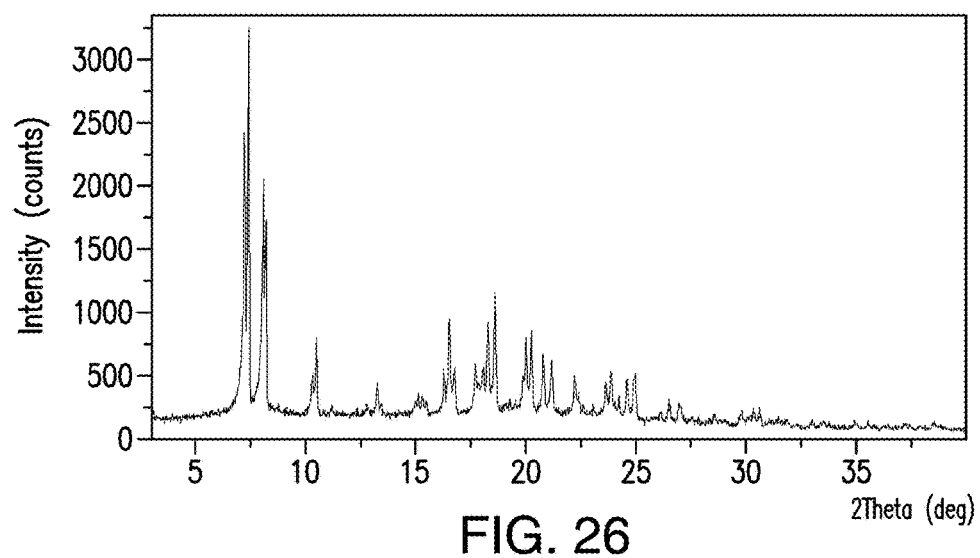
FIG. 26 is an X-ray powder diffractogram (XRPD) of compound 2 Form 12.

In one embodiment, a single crystalline form, Form 12, of the compound 2 is characterized by the X-ray powder diffraction (XRPD) pattern shown in FIG. 26, and data shown in Table 12A, obtained using CuKa radiation. In a particular embodiment, the polymorph can be characterized by one or more of the peaks taken from FIG. 26, as shown in Table 12A. For example, the polymorph can be characterized by one or two or three or four or five or six or seven or eight or nine of the peaks shown in Table 12A.

TABLE 12A

| Angle 2-Theta° | Intensity % |
| --- | --- |
| 7.2 | 75.7 |
| 7.4 | 100.0 |
| 8.0 | 61.3 |
| 8.2 | 52.4 |
| 13.2 | 9.4 |
| 16.5 | 27.2 |
| 18.6 | 32.7 |
| 20.2 | 23.6 |
| 20.8 | 18.7 |

In another embodiment, Form 12 can be characterized by the peaks identified at 2θangles of 7.2, 7.4, 8.0, 8.2, 16.5, and 18.6°. In a further embodiment, Form 12 can be characterized by the peaks are identified at 2θangles of 7.2, 7.4, 8.0, and 8.2°.

Figure 27:
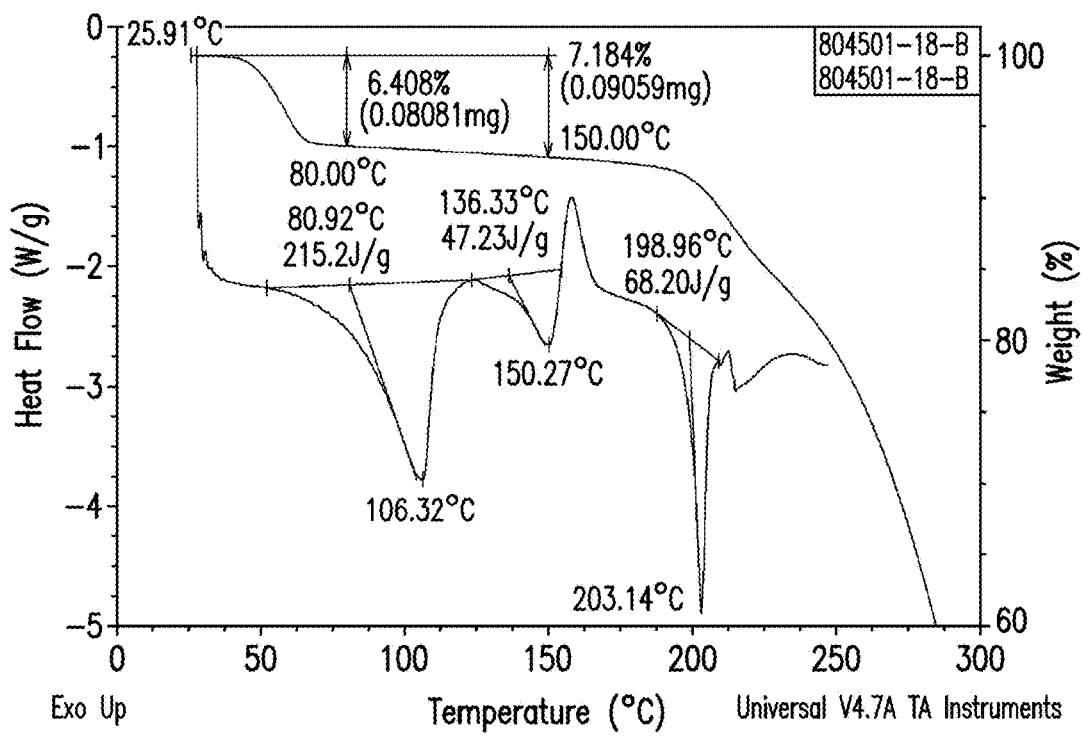
FIG. 27 is a differential scanning calorimetry (DSC) and thermal gravimetric analysis (TGA) profile of compound 2 Form 12.

In another embodiment, Form 12 can be characterized by the differential scanning calorimetry profile (DSC) shown in FIG. 27. The DSC graph plots the heat flow as a function of temperature from a sample, the temperature rate change being about 10° C./min. The profile is characterized by an endothermic transition with an onset temperature of about 80.9° C. with a melt at about 106.3° C., an endothermic transition with an onset temperature of about 136.32° C. with a melt at about 150.3° C., and a strong endothermic transition with an onset temperature of about 199.0° C. with a melt at about 203.1° C.

In another embodiment, Form 12 can be characterized by thermal gravimetric analysis (TGA) shown in FIG. 27. The TGA profile graphs the percent loss of weight of the sample as a function of temperature, the temperature rate change being about 10° C./min. The weight loss represents a loss of about 6.4% of the weight of the sample as the temperature is changed from about 25.9° C. to 80.0° C., and a loss of about 7.2% of the weight of the sample as the temperature is changed from about 25.9° C. to 150.0° C.

Form 13

Figure 28:
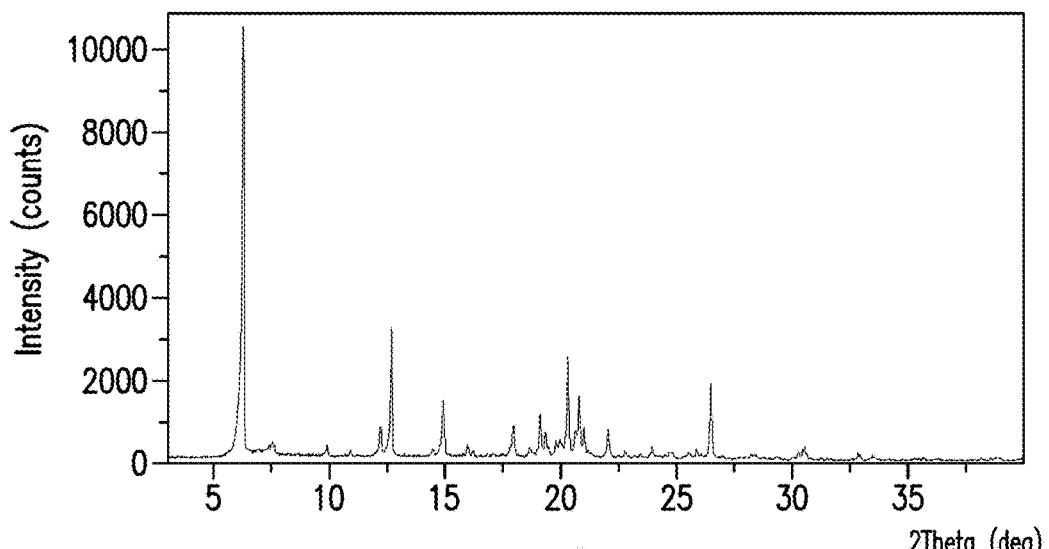
FIG. 28 is a X-ray powder diffractogram (XRPD) of compound 2 Form 13.

In one embodiment, a single crystalline form, Form 13, of the compound 2 is characterized by the X-ray powder diffraction (XRPD) pattern shown in FIG. 28, and data shown in Table 13A, obtained using CuKa radiation. In a particular embodiment, the polymorph can be characterized by one or more of the peaks taken from FIG. 28, as shown in Table 13A. For example, the polymorph can be characterized by one or two or three or four or five or six or seven or eight or nine of the peaks shown in Table 13A.

TABLE 13A

| Angle 2-Theta° | Intensity % |
| --- | --- |
| 6.3 | 100.0 |
| 12.7 | 30.1 |
| 14.9 | 14.1 |
| 18.0 | 8.4 |
| 19.1 | 10.8 |
| 20.3 | 24.3 |
| 20.8 | 15.2 |
| 22.0 | 7.2 |
| 26.5 | 18.2 |

In another embodiment, Form 13 can be characterized by the peaks identified at 2θangles of 6.3, 12.7, 20.3, 20.8, and 26.5°. In a further embodiment, Form 13 can be characterized by the peaks are identified at 2θangles of 6.3, 12.7, and 20.3°.

Figure 29:
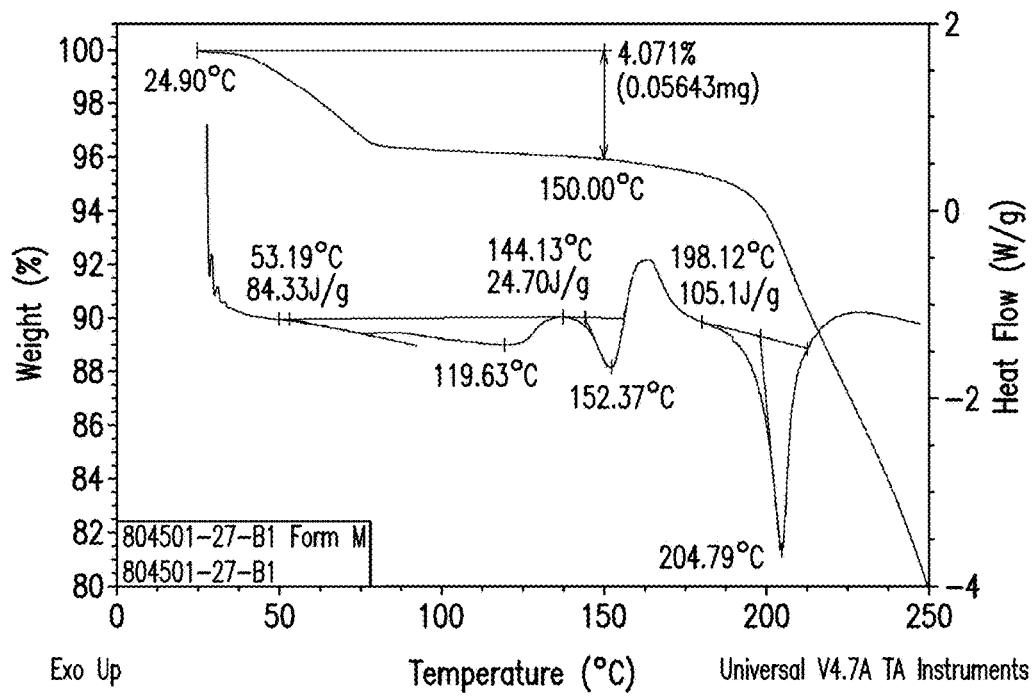
FIG. 29 is a differential scanning calorimetry (DSC) and thermal gravimetric analysis (TGA) profile of compound 2 Form 13.

In another embodiment, Form 13 can be characterized by the differential scanning calorimetry profile (DSC) shown in FIG. 29. The DSC graph plots the heat flow as a function of temperature from a sample, the temperature rate change being about 10° C./min. The profile is characterized by a weak endothermic transition with an onset temperature of about 144.1° C. with a melt at about 152.4° C., and a strong endothermic transition with an onset temperature of about 198.1° C. with a melt at about 204.8° C.

In another embodiment, Form 13 can be characterized by thermal gravimetric analysis (TGA) shown in FIG. 29. The TGA profile graphs the percent loss of weight of the sample as a function of temperature, the temperature rate change being about 10° C./min. The weight loss represents a loss of about 4.1% of the weight of the sample as the temperature is changed from about 24.9° C. to 150.0° C.

Form 14

Figure 30:
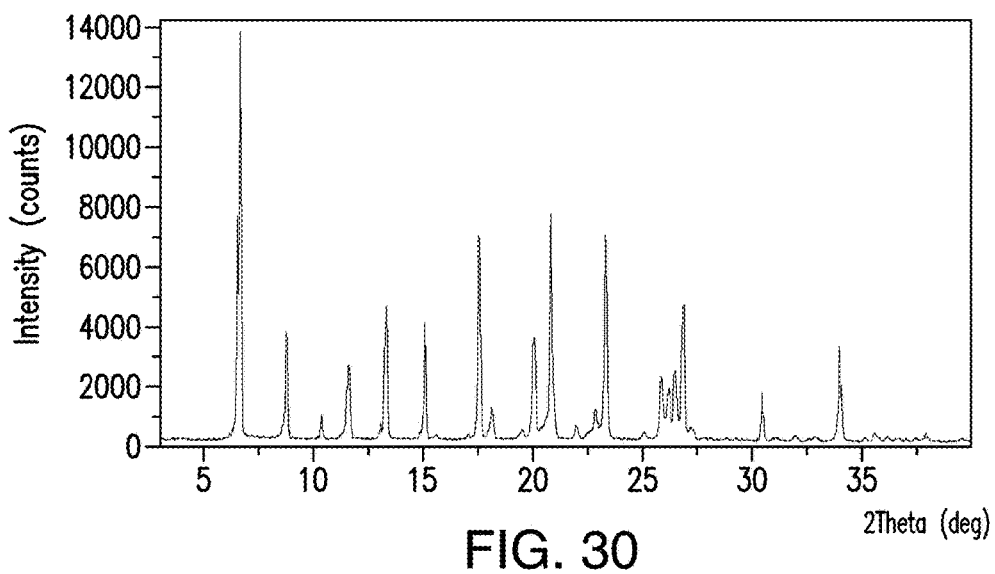
FIG. 30 is an X-ray powder diffractogram (XRPD) of compound 2 Form 14.

In one embodiment, a single crystalline form, Form 14, of the compound 2 is characterized by the X-ray powder diffraction (XRPD) pattern shown in FIG. 30, and data shown in Table 14A, obtained using CuKa radiation. In a particular embodiment, the polymorph can be characterized by one or more of the peaks taken from FIG. 30, as shown in Table 14A. For example, the polymorph can be characterized by one or two or three or four or five or six or seven or eight or nine of the peaks shown in Table 14A.

TABLE 14A

| Angle 2-Theta° | Intensity % |
| --- | --- |
| 6.6 | 100.0 |
| 8.7 | 26.9 |
| 10.3 | 6.7 |
| 13.3 | 30.8 |
| 15.1 | 26.5 |
| 17.5 | 49.6 |
| 20.8 | 54.8 |
| 23.3 | 49.1 |
| 26.8 | 33.4 |

In another embodiment, Form 14 can be characterized by the peaks identified at 2θangles of 6.6, 17.5, 20.8 and 23.3°. In a further embodiment, Form 14 can be characterized by the peaks are identified at 2θangles of 6.6 and 20.8°.

Figure 31:
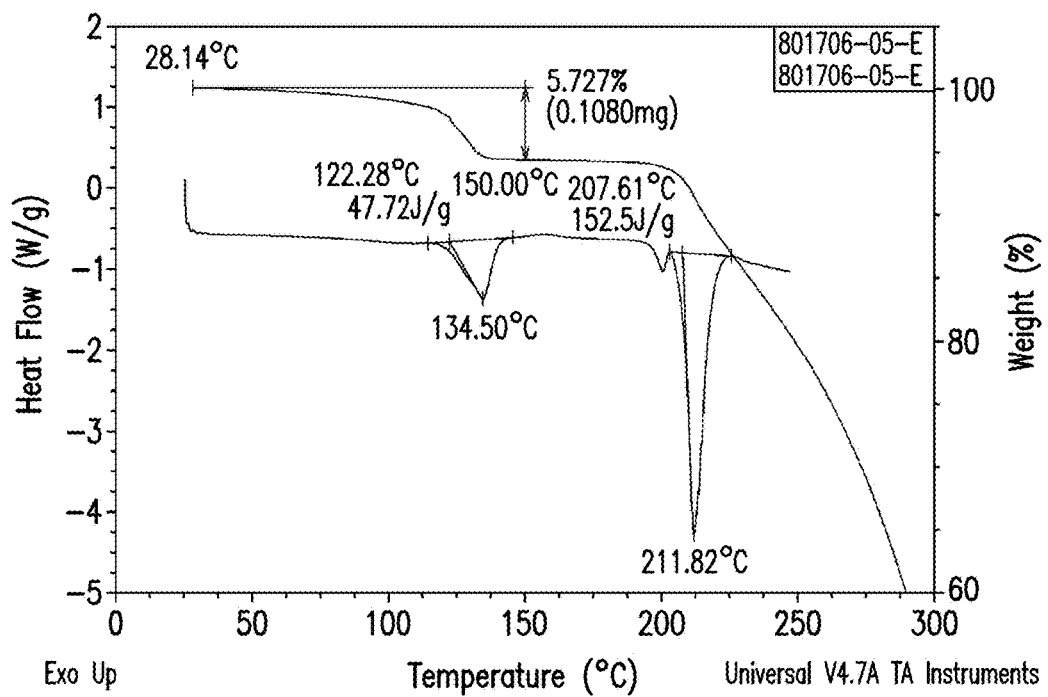
FIG. 31 is a differential scanning calorimetry (DSC) and thermal gravimetric analysis (TGA) profile of compound 2 Form 14.

In another embodiment, Form 14 can be characterized by the differential scanning calorimetry profile (DSC) shown in FIG. 31. The DSC graph plots the heat flow as a function of temperature from a sample, the temperature rate change being about 10° C./min. The profile is characterized by a weak endothermic transition with an onset temperature of about 122.3° C. with a melt at about 134.5° C., and a strong endothermic transition with an onset temperature of about 207.6° C. with a melt at about 211.8° C.

In another embodiment, Form 14 can be characterized by thermal gravimetric analysis (TGA) shown in FIG. 31. The TGA profile graphs the percent loss of weight of the sample as a function of temperature, the temperature rate change being about 10° C./min. The weight loss represents a loss of about 5.71% of the weight of the sample as the temperature is changed from about 28.1° C. to 150.0° C.

Form 15

Figure 32:
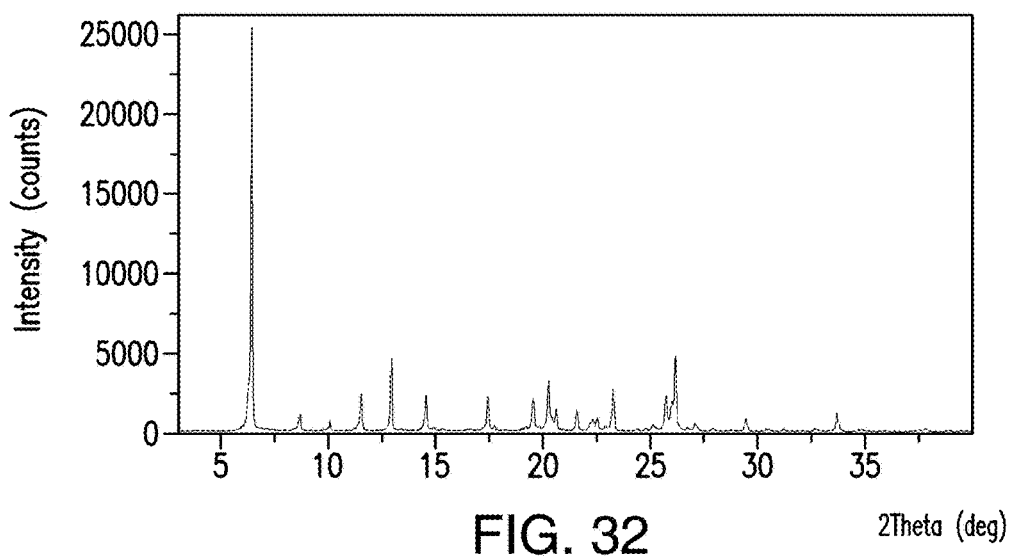
FIG. 32 is an X-ray powder diffractogram (XRPD) of compound 2 Form 15.

In one embodiment, a single crystalline form, Form 15, of the compound 2 is characterized by the X-ray powder diffraction (XRPD) pattern shown in FIG. 32, and data shown in Table 15A, obtained using CuKa radiation. In a particular embodiment, the polymorph can be characterized by one or more of the peaks taken from FIG. 32, as shown in Table 15A. For example, the polymorph can be characterized by one or two or three or four or five or six or seven or eight or nine of the peaks shown in Table 15A.

TABLE 15A

| Angle 2-Theta° | Intensity % |
| --- | --- |
| 6.4 | 100.0 |
| 11.5 | 9.2 |
| 12.9 | 18.0 |
| 19.5 | 8.0 |
| 20.2 | 12.4 |
| 21.6 | 5.0 |
| 23.2 | 10.2 |
| 26.1 | 19.0 |
| 29.4 | 3.2 |

In another embodiment, Form 15 can be characterized by the peaks identified at 2θangles of 6.4, 12.9, 20.2, and 26.10. In a further embodiment, Form 15 can be characterized by the peaks are identified at 2θangles of 6.4, 12.9, and 26.10°.

Figure 33:
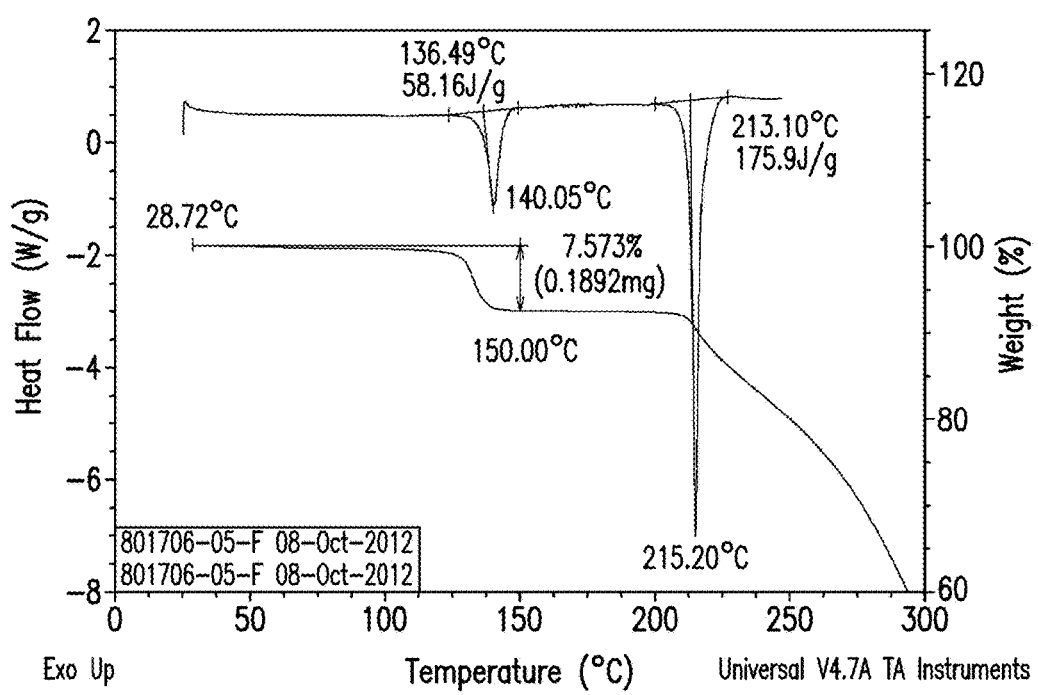
FIG. 33 is a differential scanning calorimetry (DSC) and thermal gravimetric analysis (TGA) profile of compound 2 Form 15.

In another embodiment, Form 15 can be characterized by the differential scanning calorimetry profile (DSC) shown in FIG. 33. The DSC graph plots the heat flow as a function of temperature from a sample, the temperature rate change being about 10° C./min. The profile is characterized by a weak endothermic transition with an onset temperature of about 136.5° C. with a melt at about 140.1° C., and a strong endothermic transition with an onset temperature of about 213.1° C. with a melt at about 215.2° C.

In another embodiment, Form 15 can be characterized by thermal gravimetric analysis (TGA) shown in FIG. 33. The TGA profile graphs the percent loss of weight of the sample as a function of temperature, the temperature rate change being about 10° C./min. The weight loss represents a loss of about 7.6% of the weight of the sample as the temperature is changed from about 28.7° C. to 150.0° C.

Form 16

Figure 34:
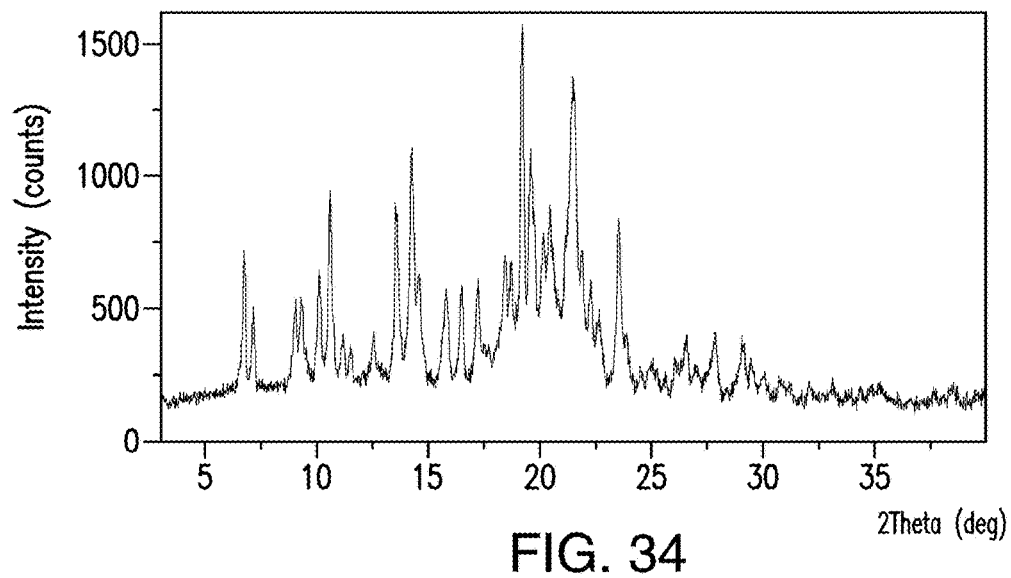
FIG. 34 is an X-ray powder diffractogram (XRPD) of compound 1 Form 16.

In one embodiment, a single crystalline form, Form 16, of the compound 1 is characterized by the X-ray powder diffraction (XRPD) pattern shown in FIG. 34, and data shown in Table 16A, obtained using CuKa radiation. In a particular embodiment, the polymorph can be characterized by one or more of the peaks taken from FIG. 34, as shown in Table 16A. For example, the polymorph can be characterized by one or two or three or four or five or six or seven or eight or nine of the peaks shown in Table 16A.

TABLE 16A

| Angle 2-Theta° | Intensity % |
| --- | --- |
| 6.8 | 35.5 |
| 10.1 | 30.7 |
| 10.6 | 53.1 |
| 13.6 | 46.0 |
| 14.2 | 63.8 |
| 17.2 | 26.4 |
| 18.4 | 34.0 |
| 19.2 | 100.0 |
| 23.5 | 3.8 |

In another embodiment, Form 16 can be characterized by the peaks identified at 2θangles of 6.8, 10.6, 13.6, 14.2, and 19.2°. In another embodiment, Form 16 can be characterized by the peaks identified at 2θangles of 10.6, 14.2, and 19.2°.

Figure 35:
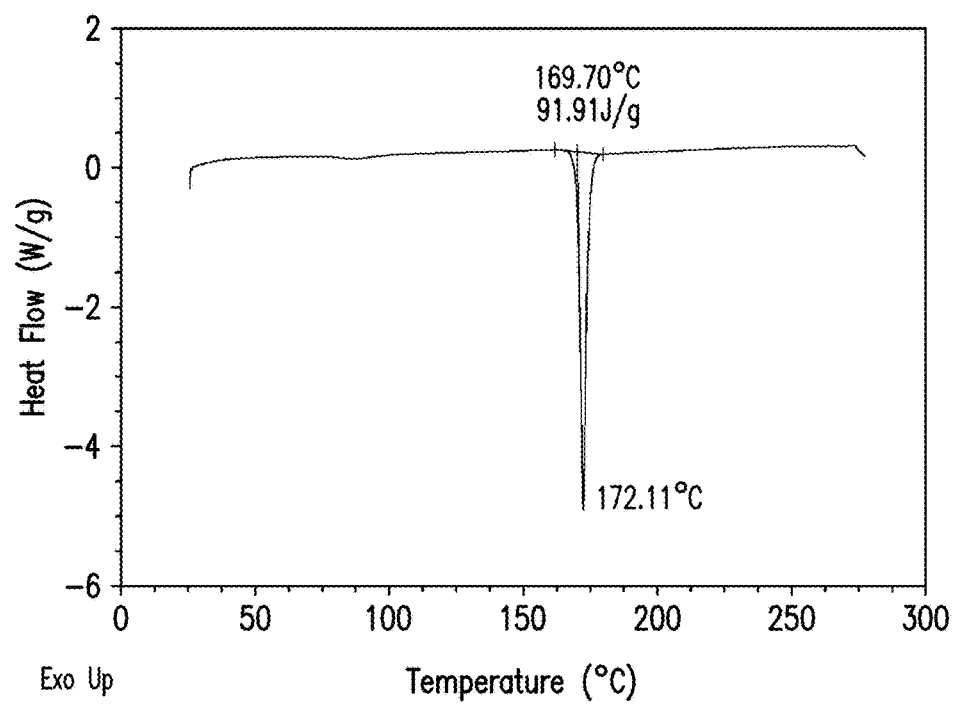
FIG. 35 is a differential scanning calorimetry (DSC) profile of compound 1 Form 16.

In another embodiment, Form 16 can be characterized by the differential scanning calorimetry profile (DSC) shown in FIG. 35. The DSC graph plots the heat flow as a function of temperature from a sample, the temperature rate change being about 10° C./min. The profile is characterized by a strong endothermic transition with an onset temperature of about 169.7° C. with a melt at about 172.1° C.

Figure 36:
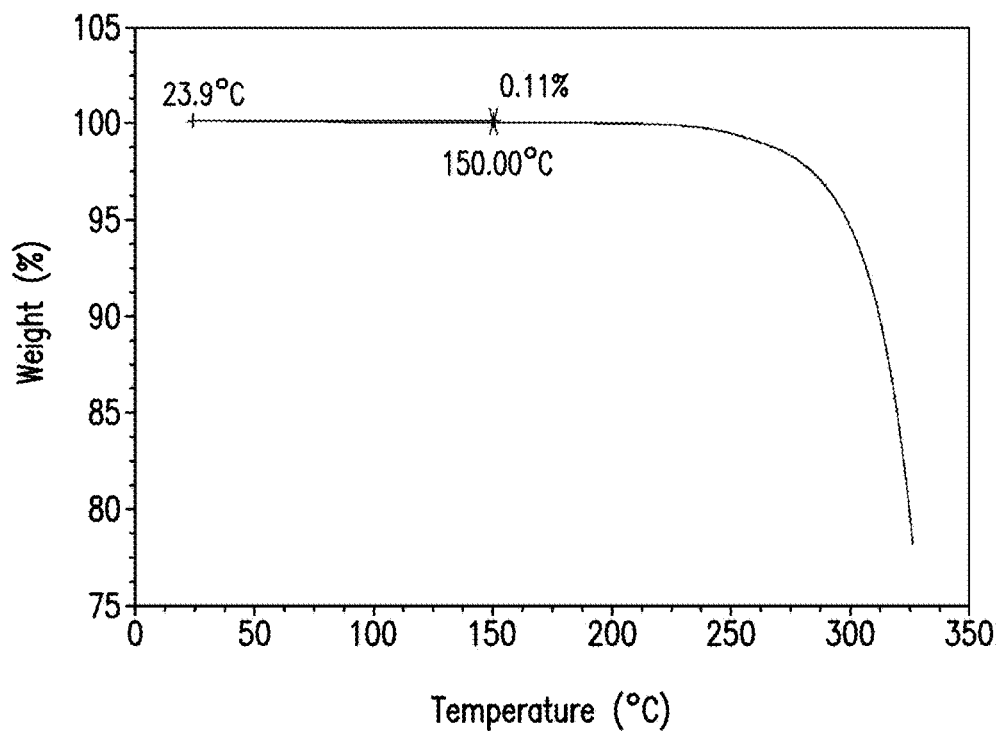
FIG. 36 is a thermal gravimetric analysis (TGA) profile of compound 1 Form 16.

In another embodiment, Form 16 can be characterized by thermal gravimetric analysis (TGA) shown in FIG. 36. The TGA profile graphs the percent loss of weight of the sample as a function of temperature, the temperature rate change being about 10° C./min. The weight loss represents a loss of about 0.1% of the weight of the sample as the temperature is changed from about 23.9° C. to 150.0° C.

Form 17

Figure 37:
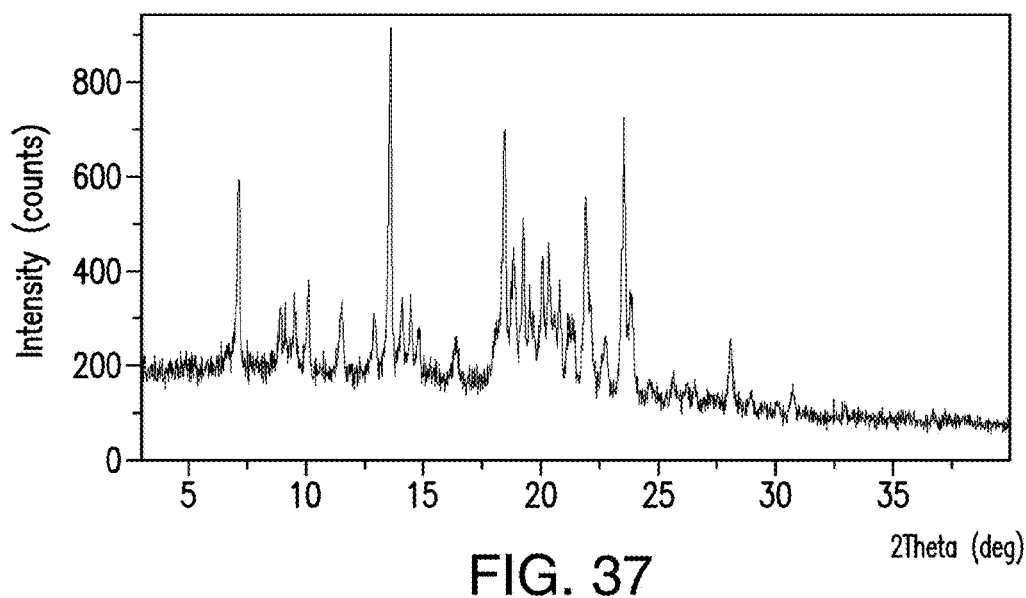
FIG. 37 is an X-ray powder diffractogram (XRPD) of compound 1 Form 17.

In one embodiment, a single crystalline form, Form 17, of the compound 1 is characterized by the X-ray powder diffraction (XRPD) pattern shown in FIG. 37, and data shown in Table 17A, obtained using CuKa radiation. In a particular embodiment, the polymorph can be characterized by one or more of the peaks taken from FIG. 37, as shown in Table 17A. For example, the polymorph can be characterized by one or two or three or four or five or six or seven or eight or nine of the peaks shown in Table 17A.

TABLE 17A

| Angle 2-Theta° | Intensity % |
| --- | --- |
| 7.2 | 53.3 |
| 10.1 | 26.7 |
| 11.5 | 20.5 |
| 13.6 | 100.0 |
| 18.5 | 72.0 |
| 19.3 | 46.9 |
| 20.3 | 39.4 |
| 21.9 | 55.4 |
| 23.5 | 77.5 |

In another embodiment, Form 17 can be characterized by the peaks identified at 2θangles of 7.2, 13.6, 18.5, 19.3, 21.9, and 23.5°. In another embodiment, Form 17 can be characterized by the peaks identified at 2θangles of 13.6, 18.5, and 23.5°.

Form 18

Figure 38:
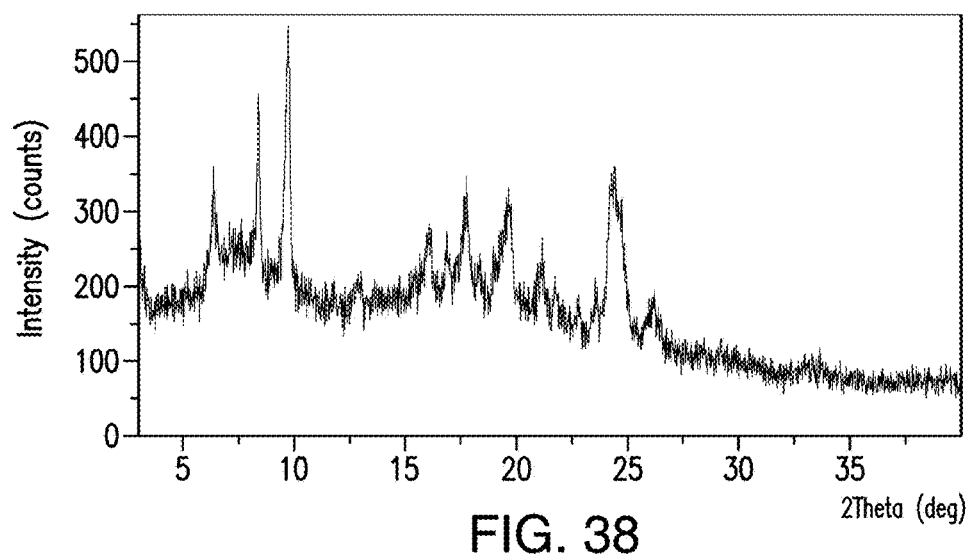
FIG. 38 is an X-ray powder diffractogram (XRPD) of compound 1 Form 18.

In one embodiment, a single crystalline form, Form 18, of the compound 1 is characterized by the X-ray powder diffraction (XRPD) pattern shown in FIG. 38, and data shown in Table 18A, obtained using CuKa radiation. In a particular embodiment, the polymorph can be characterized by one or more of the peaks taken from FIG. 38, as shown in Table 18A. For example, the polymorph can be characterized by one or two or three or four or five or six or seven or eight or nine of the peaks shown in Table 18A.

TABLE 18A

| Angle 2-Theta° | Intensity % |
| --- | --- |
| 6.4 | 45.4 |
| 8.4 | 84.0 |
| 9.8 | 100.0 |
| 16.1 | 26.0 |
| 16.9 | 22.7 |
| 17.8 | 43.6 |
| 19.7 | 40.4 |
| 21.1 | 20.5 |
| 26.1 | 15.9 |

In another embodiment, Form 18 can be characterized by the peaks identified at 2θangles of 6.4, 8.4, 9.8, 17.8, and 19.7°. In another embodiment, Form 18 can be characterized by the peaks identified at 2θangles of 8.4 and 9.8°.

Form 19

Figure 39:
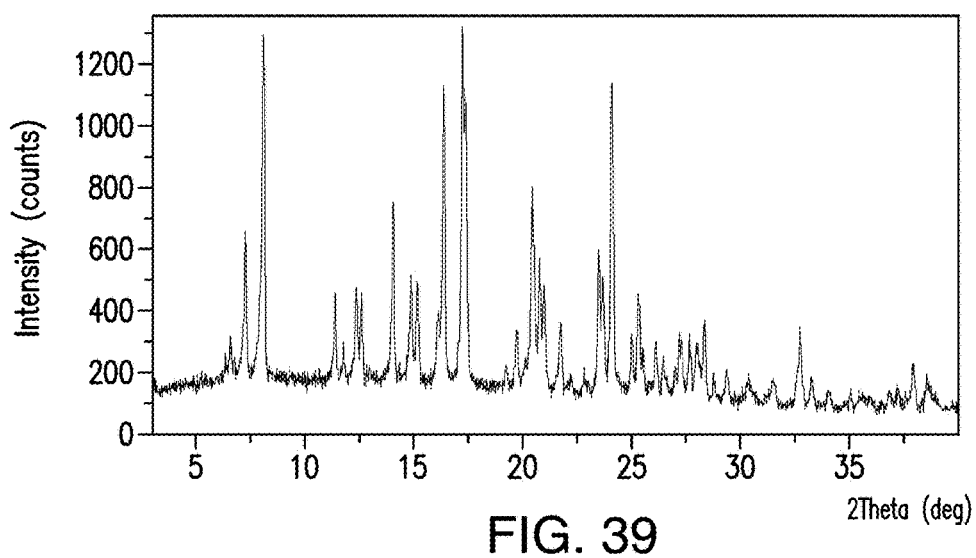
FIG. 39 is an X-ray powder diffractogram (XRPD) of compound 1 Form 19.

In one embodiment, a single crystalline form, Form 19, of the compound 1 is characterized by the X-ray powder diffraction (XRPD) pattern shown in FIG. 39, and data shown in Table 19A, obtained using CuKa radiation. In a particular embodiment, the polymorph can be characterized by one or more of the peaks taken from FIG. 39, as shown in Table 19A. For example, the polymorph can be characterized by one or two or three or four or five or six or seven or eight of the peaks shown in Table 19A.

TABLE 19A

| Angle 2-Theta° | Intensity % |
|---|---|
| 8.1 | 97.9 |
| 11.4 | 24.9 |
| 14.1 | 51.5 |
| 15.2 | 28.4 |
| 16.4 | 85.0 |
| 17.3 | 100.0 |
| 20.5 | 54.7 |
| 24.1 | 88.7 |

In another embodiment, Form 19 can be characterized by the peaks identified at 2θangles of 8.1, 14.1, 16.4, 17.3, 20.5, and 24.1°. In another embodiment, Form 19 can be characterized by the peaks identified at 2θangles of 8.1, 16.4, 17.3, and 24.10.

Other embodiments are directed to a single crystalline form of compound 1 or compound 2 characterized by a combination of the aforementioned characteristics of any of the single crystalline forms discussed herein. The characterization may be by any combination of one or more of the XRPD, TGA, DSC, and DVS described for a particular polymorph. For example, the single crystalline form of compound 1 or compound 2 may be characterized by any combination of the XRPD results regarding the position of the major peaks in a XRPD scan; and/or any combination of one or more of parameters derived from data obtained from a XRPD scan. The single crystalline form of compound 1 or compound 2 may also be characterized by TGA determinations of the weight loss associated with a sample over a designated temperature range; and/or the temperature at which a particular weight loss transition begins. DSC determinations of the temperature associated with the maximum heat flow during a heat flow transition and/or the temperature at which a sample begins to undergo a heat flow transition may also characterize the crystalline form. Weight change in a sample and/or change in sorption/desorption of water per molecule of compound 1 or compound 2 as determined by water sorption/desorption measurements over a range of relative humidity (e.g., 0% to 90%) may also characterize a single crystalline form of compound 1 or compound 2.

The combinations of characterizations that are discussed above may be used to describe any of the polymorphs of compound 1 or compound 1 discussed herein, or any combination of these polymorphs.

EXAMPLES

Abbreviations ca approximately
$CHCl_3$—chloroform
DCM—dichloromethane
DMF—dimethylformamide
$Et_2O$—diethyl ether
EtOH—ethyl alcohol
EtOAc—ethyl acetate
MeOH—methyl alcohol
MeCN—acetonitrile
PE—petroleum ether
THF—tetrahydrofuran
AcOH—acetic acid
HCl—hydrochloric acid
$H_2SO_4$—sulfuric acid
$NH_4Cl$—ammonium chloride
KOH—potassium hydroxide
NaOH—sodium hydroxide
$Na_2CO_3$—sodium carbonate
TFA—trifluoroacetic acid
$NaHCO_3$—sodium bicarbonate
DMSO dimethylsulfoxide
DSC differential scanning calorimetry
DVS dynamic vapor sorption
GC gas chromatography
h hours
HPLC high performance liquid chromatography
min minutes
m/z mass to charge
MS mass spectrum
NMR nuclear magnetic resonance
RT room temperature
TGA thermal gravimetric analysis
XRPD X-Ray Powder Diffraction/X-Ray Powder Diffractogram/X-Ray Powder Diffractometer General Methods In the following examples, reagents may be purchased from commercial sources (including Alfa, Acros, Sigma Aldrich, TCI and Shanghai Chemical Reagent Company), and used without further purification. Nuclear magnetic resonance (NMR) spectra may be obtained on a Brucker AMX-400 NMR (Brucker, Switzerland). Chemical shifts are reported in parts per million (ppm, 6) downfield from tetramethylsilane. Mass spectra may be run with electrospray ionization (ESI) from a Waters LCT TOF Mass Spectrometer (Waters, USA).

For exemplary compounds, including crystalline forms thereof, disclosed in this section, the specification of a stereoisomer (e.g., an (R) or (S) stereoisomer) indicates a preparation of that compound such that the compound is enriched at the specified stereocenter by at least about 90%, 95%, 96%, 97%, 98%, or 99%.

The chemical name of each of the exemplary compound described below is generated by ChemDraw software.

X-Ray Powder Diffraction (XRPD) Parameters:

XRPD analysis was performed using a PANalytical Empyrean X-ray powder diffractometer (XRPD) with a 12-auto sample stage. The XRPD parameters used are listed in Table 20.

TABLE 20

| | Parameters for Reflection Mode |
|---|---|
| X-Ray wavelength | Cu, kα, Kα1 (Å): 1.540598, Kα2 (Å): 1.544426 Kα2/Kα1 intensity ratio: 0.50 |
| X-Ray tube setting | 45 kV, 40 mA |
| Divergence slit | Automatic |
| Scan mode | Continuous |
| Scan range (°2TH) | 3°-40° |
| Step size (°2TH) | 0.0170 |
| Scan speed (°/min) | About 10 |

For Form 3, XRPD analysis was performed using a LYNXEYE XE Detector (Bruker). The XRPD parameters used are listed in Table 21.

TABLE 21

| | Parameters for Reflection Mode |
|---|---|
| X-Ray wavelength | Cu, kα, |
| | Kα1 (Å): 1.54060, Kα2 (Å): 1.54439 |
| | Kα2/Kα1 intensity ratio: 0.50 |
| Scan range (°2TH) | 3°-40° |
| Step size (°2TH) | 0.012 |

Differential Scanning Calorimetry (DSC) Parameters:

DSC analysis was performed using a TA Q100, or Q200/Q2000 DSC from TA Instruments. The temperature was ramped from room temperature to the desired temperature at a heating rate of 10° C./min using $N_2$ as the purge gas, with pan crimped.

Thermogravimetric Analysis (TGA) Parameters:

TGA analysis was performed using a TA Q500/Q5000 TGA from TA Instruments. The temperature was ramped from room temperature to the desired temperature at a heating rate of 10° C./min or 20° C./min using $N_2$ as the purge gas.

Dynamic Vapor Sorption (DVS) Parameters:

DVS was measured via a SMS (Surface Measurement Systems) DVS Intrinsic. The relative humidity at 25° C. were calibrated against deliquescence point of LiCl, $Mg(NO_3)_2$ and KCl. The DVS Parameters used are listed in Table 22.

TABLE 22

| | DVS |
|---|---|
| Temperature | 25° C. |
| Sample size | 10-20 mg |
| Gas and flow rate | $N_2$, 200 mL/min |
| dm/dt | 0.002%/min |
| Min. dm/dt stability duration | 10 min |
| Max. equilibrium time | 180 min |
| RH range | 60% RH-95% RH-0% RH-95% RH |
| RH step size | 10% (0% RH-90% RH, 90% RH--0% RH) |
| | 5% (90% RH-95% RH-90% RH) |

Example 1: Synthesis of Compound 1

Example 1, Step 1: preparation of 6-trifluoromethyl-pyridine-2-carboxylic acid

Diethyl ether (4.32 L) and hexanes (5.40 L) are added to the reaction vessel under $N_2$ atmosphere, and cooled to −75° C. to −65° C. Dropwise addition of n-Butyl lithium (3.78 L in 1.6 M hexane) under $N_2$ atmosphere at below −65° C. is followed by dropwise addition of dimethyl amino ethanol (327.45 g, 3.67 mol) and after 10 min. dropwise addition of 2-trifluoromethyl pyridine (360 g, 2.45 mol). The reaction is stirred under $N_2$ while maintaining the temperature below −65° C. for about 2.0-2.5 hrs. The reaction mixture is poured over crushed dry ice under $N_2$, then brought to a temperature of 0 to 5° C. while stirring (approx. 1.0 to 1.5 h) followed by the addition of water (1.8 L). The reaction mixture is stirred for 5-10 mins and allowed to warm to 5-10° C. 6N HCl (900 mL) is added dropwise until the mixture reached pH 1.0 to 2.0, then the mixture is stirred for 10-20 min. at 5-10° C. The reaction mixture is diluted with ethyl acetate at 25-35° C., then washed with brine solution. The reaction is concentrated and rinsed with n-heptane and then dried to yield 6-trifluoromethyl-pyridine-2-carboxylic acid.

Example 1, Step 2: preparation of 6-trifluoromethyl-pyridine-2-carboxylic acid methyl ester Methanol is added to the reaction vessel under nitrogen atmosphere. 6-trifluoromethyl-pyridine-2-carboxylic acid (150 g, 0.785 mol) is added and dissolved at ambient temperature. Acetyl chloride (67.78 g, 0.863 mol) is added dropwise at a temperature below 45° C. The reaction mixture is maintained at 65-70° C. for about 2-2.5 h, and then concentrated at 35-45° C. under vacuum and cooled to 25-35° C. The mixture is diluted with ethyl acetate and rinsed with saturated $NaHCO_3$ solution then rinsed with brine solution. The mixture is concentrated at temp 35-45° C. under vacuum and cooled to 25-35° C., then rinsed with n-heptane and concentrated at temp 35-45° C. under vacuum, then degassed to obtain brown solid, which is rinsed with n-heptane and stirred for 10-15 minute at 25-35° C. The suspension is cooled to −40 to −30° C. while stirring, and filtered and dried to provide 6-trifluoromethyl-pyridine-2-carboxylic acid methyl ester.

Example 1, Step 3: preparation of 6-(6-Trifluoromethyl-pyridin-2-yl)-1H-1,3,5-triazine-2,4-dione 1 L absolute ethanol is charged to the reaction vessel under $N_2$ atmosphere and Sodium Metal (11.2 g, 0.488 mol) is added in portions under $N_2$ atmosphere at below 50° C. The reaction is stirred for 5-10 minutes, then heated to 50-55° C. Dried Biuret (12.5 g, 0.122 mol) is added to the reaction vessel under $N_2$ atmosphere at 50-55° C. temperature, and stirred 10-15 minutes. While maintaining 50-55° C. 6-trifluoromethyl-pyridine-2-carboxylic acid methyl ester (50.0 g, 0.244 mol) is added. The reaction mixture is heated to reflux (75-80° C.) and maintained for 1.5-2 hours. Then cooled to 35-40° C., and concentrated at 45-50° C. under vacuum. Water is added and the mixture is concentrated under vacuum then cooled to 35-40° C. more water is added and the mixture cooled to 0-5° C. pH is adjusted to 7-8 by slow addition of 6N HCl, and solid precipitated out and is centrifuged and rinsed with water and centrifuged again. The off white to light brown solid of 6-(6-Trifluoromethyl-pyridin-2-yl)-1H-1,3,5-triazine-2,4-dione is dried under vacuum for 8 to 10 hrs at 50° C. to 60° C. under 600 mm/Hg pressure to provide 6-(6-Trifluoromethyl-pyridin-2-yl)-1H-1,3,5-triazine-2,4-dione.

Example 1, Step 4: preparation of 2,4-Dichloro-6-(6-trifluoromethyl-pyridin-2-yl)-1,3,5-triazine $POCl_3$ (175.0 mL) is charged into the reaction vessel at 20-35° C., and 6-(6-Trifluoromethyl-pyridin-2-yl)-1H-1,3,5-triazine-2,4-dione (35.0 g, 0.1355 mol) is added in portions at below 50° C. The reaction mixture is de-gassed 5-20 minutes by purging with $N_2$ gas. Phosphorous pentachloride (112.86 g, 0.542 mol) is added while stirring at below 50° C. and the resulting slurry is heated to reflux (105-110° C.) and maintained for 3-4 h. The reaction mixture is cooled to 50-55° C., and concentrated at below 55° C. then cooled to 20-30° C. The reaction mixture is rinsed with ethyl acetate and the ethyl acetate layer is slowly added to cold water (temperature ~5° C.) while stirring and maintaining the temperature below 10° C. The mixture is stirred 3-5 minutes at a temperature of between 10 to 20° C. and the ethyl acetate layer is collected. The reaction mixture is rinsed with sodium bicarbonate solution and dried over anhydrous sodium sulphate. The material is dried 2-3 h under vacuum at below 45° C. to provide 2,4-Dichloro-6-(6-trifluoromethyl-pyridin-2-yl)-1,3,5-triazine.

Example 1, Step 5: preparation of 4-chloro-6-(6-(trifluoromethyl)pyridin-2-yl)-N-(2-(trifluoromethyl)-pyridin-4-yl)-1,3,5-triazin-2-amine A mixture of THF (135 mL) and 2,4-Dichloro-6-(6-trifluoromethyl-pyridin-2-yl)-1,3,5-triazine (27.0 g, 0.0915 mol) are added to the reaction vessel at 20-35° C., then 4-amino-2-(trifluoromethyl)pyridine (16.31 g, 0.1006 mol) and sodium bicarbonate (11.52 g, 0.1372 mol) are added. The resulting slurry is heated to reflux (75-80° C.) for 20-24 h. The reaction is cooled to 30-40° C. and THF evaporated at below 45° C. under reduced pressure. The reaction mixture is cooled to 20-35° C. and rinsed with ethyl acetate and water, and the ethyl acetate layer collected and rinsed with 0.5 N HCl and brine solution. The organic layer is concentrated under vacuum at below 45° C. then rinsed with dichloromethane and hexanes, filtered and washed with hexanes and dried for 5-6 h at 45-50° C. under vacuum to provide 4-chloro-6-(6-(trifluoromethyl)pyridin-2-yl)-N-(2-(trifluoro-methyl)-pyridin-4-yl)-1,3,5-triazin-2-amine.

Example 1, Step 6: preparation of 2-methyl-1-(4-(6-(trifluoromethyl)pyridin-2-yl)-6-(2-(trifluoromethyl)-pyridin-4-ylamino)-1,3,5-triazin-2-ylamino)propan-2-ol THF (290 mL), 4-chloro-6-(6-(trifluoromethyl)pyridin-2-yl)-N-(2-(trifluoro-methyl)-pyridin-4-yl)-1,3,5-triazin-2-amine (29.0 g, 0.06893 mol), sodium bicarbonate (8.68 g, 0.1033 mol), and 1,1-dimethylaminoethanol (7.37 g, 0.08271 mol) are added to the reaction vessel at 20-35° C. The resulting slurry is heated to reflux (75-80° C.) for 16-20 h. The reaction is cooled to 30-40° C. and THF evaporated at below 45° C. under reduced pressure. The reaction mixture is cooled to 20-35° C. and rinsed with ethyl acetate and water, and the ethyl acetate layer collected. The organic layer is concentrated under vacuum at below 45° C. then rinsed with dichloromethane and hexanes, filtered and washed with hexanes and dried for 8-10 h at 45-50° C. under vacuum to provide 2-methyl-1-(4-(6-(trifluoromethyl)pyridin-2-yl)-6-(2-(trifluoromethyl)-pyridin-4-ylamino)-1,3,5-triazin-2-ylamino)propan-2-ol.

Example 2: Synthesis of Compound 2

Acetone (435.0 mL) and compound 1 (87.0 g, 0.184 mol) are added to the reaction vessel at 20-35° C. In a separate vessel, methanesulfonic acid is added over 10 minutes to cold (0-4° C.) acetone (191.4 mL) while stirring to prepare a methane sulfonic acid solution. While passing through a micron filter, the freshly prepared methanesulfonic acid solution is added dropwise to the reaction mixture. The resulting slurry is filtered using nutsche filter and washed with acetone. The filtered material is dried for 30-40 minutes using vacuum to provide compound 2.

Example 2A: Synthesis of Compound 1 Form 16

Example 2A, Step 1: preparation of 6-trifluoromethyl-pyridine-2-carboxylic acid

Diethyl ether (4.32 L) and hexanes (5.40 L) are added to the reaction vessel under $N_2$ atmosphere, and cooled to −75° C. to −65° C. Dropwise addition of n-Butyl lithium (3.78 L in 1.6 M hexane) under $N_2$ atmosphere at below −65° C. is followed by dropwise addition of dimethyl amino ethanol (327.45 g, 3.67 mol) and after 10 min. dropwise addition of 2-trifluoromethyl pyridine (360 g, 2.45 mol). The reaction is stirred under $N_2$ while maintaining the temperature below −65° C. for about 2.0-2.5 hrs. The reaction mixture is poured over crushed dry ice under $N_2$, then brought to a temperature of 0 to 5° C. while stirring (approx. 1.0 to 1.5 h) followed by the addition of water (1.8 L). The reaction mixture is stirred for 5-10 mins and allowed to warm to 5-10° C. 6N HCl (900 mL) is added dropwise until the mixture reached pH 1.0 to 2.0, then the mixture is stirred for 10-20 min. at 5-10° C. The reaction mixture is diluted with ethyl acetate at 25-35° C., then washed with brine solution. The reaction is concentrated and rinsed with n-heptane and then dried to yield 6-trifluoromethyl-pyridine-2-carboxylic acid.

Example 2A, Step 2: preparation of 6-trifluoromethyl-pyridine-2-carboxylic acid methyl ester Methanol is added to the reaction vessel under nitrogen atmosphere. 6-trifluoromethyl-pyridine-2-carboxylic acid (150 g, 0.785 mol) is added and dissolved at ambient temperature. Acetyl chloride (67.78 g, 0.863 mol) is added dropwise at a temperature below 45° C. The reaction mixture is maintained at 65-70° C. for about 2-2.5 h, and then concentrated at 35-45° C. under vacuum and cooled to 25-35° C. The mixture is diluted with ethyl acetate and rinsed with saturated $NaHCO_3$ solution then rinsed with brine solution. The mixture is concentrated at temp 35-45° C. under vacuum and cooled to 25-35° C., then rinsed with n-heptane and concentrated at temp 35-45° C. under vacuum, then degassed to obtain brown solid, which is rinsed with n-heptane and stirred for 10-15 minute at 25-35° C. The suspension is cooled to −40 to −30° C. while stirring, and filtered and dried to provide 6-trifluoromethyl-pyridine-2-carboxylic acid methyl ester.

Example 2A, Step 3: preparation of 6-(6-Trifluoromethyl-pyridin-2-yl)-1H-1,3,5-triazine-2,4-dione 1 L absolute ethanol is charged to the reaction vessel under $N_2$ atmosphere and Sodium Metal (11.2 g, 0.488 mol) is added in portions under $N_2$ atmosphere at below 50° C. The reaction is stirred for 5-10 minutes, then heated to 50-55° C. Dried Biuret (12.5 g, 0.122 mol) is added to the reaction vessel under $N_2$ atmosphere at 50-55° C. temperature, and stirred 10-15 minutes. While maintaining 50-55° C. 6-trifluoromethyl-pyridine-2-carboxylic acid methyl ester (50.0 g, 0.244 mol) is added. The reaction mixture is heated to reflux (75-80° C.) and maintained for 1.5-2 hours. Then cooled to 35-40° C., and concentrated at 45-50° C. under vacuum. Water is added and the mixture is concentrated under vacuum then cooled to 35-40° C. more water is added and the mixture cooled to 0-5° C. pH is adjusted to 7-8 by slow addition of 6N HCl, and solid precipitated out and is centrifuged and rinsed with water and centrifuged again. The off white to light brown solid of 6-(6-Trifluoromethyl-pyridin-2-yl)-1H-1,3,5-triazine-2,4-dione is dried under vacuum for 8 to 10 hrs at 50° C. to 60° C. under 600 mm/Hg pressure to provide 6-(6-Trifluoromethyl-pyridin-2-yl)-1H-1,3,5-triazine-2,4-dione.

Example 2A, Step 4: preparation of 2, 4-Dichloro-6-(6-trifluoromethyl-pyridin-2-yl)-1, 3, 5-triazine $POCl_3$ (175.0 mL) is charged into the reaction vessel at 20-35° C., and 6-(6-Trifluoromethyl-pyridin-2-yl)-1H-1,3, 5-triazine-2,4-dione (35.0 g, 0.1355 mol) is added in portions at below 50° C. The reaction mixture is de-gassed 5-20 minutes by purging with $N_2$ gas. Phosphorous pentachloride (112.86 g, 0.542 mol) is added while stirring at below 50° C. and the resulting slurry is heated to reflux (105-110° C.) and maintained for 3-4 h. The reaction mixture is cooled to 50-55° C., and concentrated at below 55° C. then cooled to 20-30° C. The reaction mixture is rinsed with ethyl acetate and the ethyl acetate layer is slowly added to cold water (temperature ~5° C.) while stirring and maintaining the temperature below 10° C. The mixture is stirred 3-5 minutes at a temperature of between 10 to 20° C. and the ethyl acetate layer is collected. The reaction mixture is rinsed with sodium bicarbonate solution and dried over anhydrous sodium sulphate. The material is dried 2-3 h under vacuum at below 45° C. to provide 2, 4-Dichloro-6-(6-trifluoromethyl-pyridin-2-yl)-1, 3, 5-triazine.

Example 2A, Step 5: preparation of 4-chloro-6-(6-(trifluoromethyl)pyridin-2-yl)-N-(2-(trifluoromethyl)-pyridin-4-yl)-1,3,5-triazin-2-amine A mixture of THF (135 mL) and 2, 4-Dichloro-6-(6-trifluoromethyl-pyridin-2-yl)-1, 3, 5-triazine (27.0 g, 0.0915 mol) are added to the reaction vessel at 20-35° C., then 4-amino-2-(trifluoromethyl)pyridine (16.31 g, 0.1006 mol) and sodium bicarbonate (11.52 g, 0.1372 mol) are added. The resulting slurry is heated to reflux (75-80° C.) for 20-24 h. The reaction is cooled to 30-40° C. and THF evaporated at below 45° C. under reduced pressure. The reaction mixture is cooled to 20-35° C. and rinsed with ethyl acetate and water, and the ethyl acetate layer collected and rinsed with 0.5 N HCl and brine solution. The organic layer is concentrated under vacuum at below 45° C. then rinsed with dichloromethane and hexanes, filtered and washed with hexanes and dried for 5-6 h at 45-50° C. under vacuum to provide 4-chloro-6-(6-(trifluoromethyl)pyridin-2-yl)-N-(2-(trifluoro-methyl)-pyridin-4-yl)-1,3,5-triazin-2-amine.

Example 2A, Step 6: preparation of 2-methyl-1-(4-(6-(trifluoromethyl)pyridin-2-yl)-6-(2-(trifluoromethyl)-pyridin-4-ylamino)-1,3,5-triazin-2-ylamino)propan-2-ol compound 1

THF (290 mL), 4-chloro-6-(6-(trifluoromethyl)pyridin-2-yl)-N-(2-(trifluoro-methyl)-pyridin-4-yl)-1,3,5-triazin-2-amine (29.0 g, 0.06893 mol), sodium bicarbonate (8.68 g, 0.1033 mol), and 1,1-dimethylaminoethanol (7.37 g, 0.08271 mol) are added to the reaction vessel at 20-35° C. The resulting slurry is heated to reflux (75-80° C.) for 16-20 h. The reaction is cooled to 30-40° C. and THF evaporated at below 45° C. under reduced pressure. The reaction mixture is cooled to 20-35° C. and rinsed with ethyl acetate and water, and the ethyl acetate layer collected. The organic layer is concentrated under vacuum at below 45° C. then rinsed with dichloromethane and hexanes, filtered and washed with hexanes and dried for 8-10 h at 45-50° C. under vacuum to provide 2-methyl-1-(4-(6-(trifluoromethyl)pyridin-2-yl)-6-(2-(trifluoromethyl)-pyridin-4-ylamino)-1,3,5-triazin-2-ylamino)propan-2-ol.

Example 3A: Synthesis of Compound 1 Form 1

Method A:
Slurry conversion is conducted by suspending ca 10 mg of Form 3 in 0.5-1.0 mL of water. After the suspension is stirred at 50° C. for 48 h, the remaining solids are centrifuged to provide Form 1.

Method B:
9.61 mg of Form 3 is dissolved in 0.2 mL of ethanol. The solution is placed at ambient condition and ethanol is evaporated to get Form 1.

Method C:
6.93 mg of Form 3 is dissolved in 0.2 mL of isopropyl acetate. The solution is placed at ambient temperature and isopropyl acetate is evaporated to get Form 1.

Example 4A: Synthesis of Compound 1 Form 2

Method A:
Slurry conversion is conducted by suspending ca 10 mg of Form 3 in 0.5-1.0 mL of water. After the suspension is stirred at RT for 48 h, the remaining solids are centrifuged to provide Form 2.

Method B:
6.07 mg of Form 3 is suspended in 1.0 mL of water. The suspension is stirred at room temperature for about 24 hours. The solid is isolated to obtain Form 2.

Example 6A: Synthesis of Compound 2 Form 3

While stirring, acetone (961.1 ml) is added to reaction vessel. The reaction is agitated and cooled to 15° C. then methanesulfonic acid (28.3 g) is added and the reaction is aged for at least 10 minutes. Crystallization to Form 3 is accomplished via the following salt formation: 1) acetone (500 ml, 4.17 vol) is charged to the crystallizer, then the mixture is agitated (550 rpm) for 10 min., 2) compound 1 (120.0 g, 253.5 mmol) is charged into crystallizer via solid charger over 45 min., 3) the solid charger is rinsed with acetone (100 ml, 0.83 vol), 4) the reaction is stirred (550 rpm) and heated to 35° C. to obtain a clear solution (in 10 min), 5) a first portion (2%) of MSA/acetone solution (0.3 mol/L, 18.1 ml, 3.8 ml/min) is added over 5 min via a piston pump, then the pump pipeline is washed with acetone (5 ml, 0.04 vol), 6) the mixture is aged at 35° C. for 10 to 15 min, while ensuring the solution remains clear, 7) compound 2 seed (2.4 g as generated in Example 5, 2 wt %) is added, to the clear solution, 8) a second portion (49%) of MSA/acetone solution (0.3 mom/L, 444 ml, 3.7 ml/min) is added over 2 hrs, 9) the mixture is aged at 35° C. for 30 min, 10) a third portion (49%) of MSA/acetone solution (0.3 mom/L, 444 ml, 7.4 ml/min) is added over 1 hr, 11) the mixture is aged at 35° C. for 2 hr, 12) the mixture is cooled to 20° C. for 1 hr, 13) the mixture is filtered and the cake washed with acetone (240 ml twice), 17) and dried under vacuum at 30° C.; to provide Form 3 crystals.

Example 7A: Synthesis of Compound 2 Form 4

Reactive crystallization is conducted by mixing compound 1 (0.1 mol/L) and methanesulfonic acid (0.1 mol/L) in MeCN to provide Form 4.

Example 8A: Synthesis of Compound 2 Form 5

Reactive crystallization is conducted by mixing compound 1 (0.1 mol/L) and methanesulfonic acid (0.1 mol/L) in isopropyl alcohol to provide Form 5.

Example 9A: Synthesis of Compound 2 Form 6

Slow evaporation is performed by dissolving ca 10 mg of Form 3 in 0.4-3.0 mL of solvent in a 3-mL glass vial. The vials are covered with foil with about 6 to 8 holes and the visually clear solutions are subjected to slow evaporation at RT to induce precipitation. Then the solids are isolated. Form 6 is provided when the solvent or solvent mixture is MeOH, EtOH, IPA, THF, MeOH/Toluene=3:1, MeOH/CAN=3:1, MeOH/IPAc=3:1, MeOH/H$_2$O=3:1, EtOH/Acetone=5:1, EtOH/DCM=5:1, MeOH/Dioxane=3:1, MeOH/MTBE=3:1, EtOH/Acetone=1:1, and THF/H$_2$O=3:1.

Example 10A: Synthesis of Compound 2 Form 7

Reactive crystallization is conducted by quickly adding methanesulfonic acid (0.1 mol/L) to compound 1 (0.1 mol/L) in acetone or MeCN to provide Form 7.

Example 11A: Synthesis of Compound 2 Form 8

Method A
Methanesulfonic acid (0.1 mol/L) is quickly added to compound 1 (0.1 mol/L) in acetone to provide Form 8.
Method B
Form 12 is heated to 155° C. in TGA and cooled to RT to provide Form 8.

Example 12A: Synthesis of Compound 2 Form 9 compound 1 (0.1 mol/L) and methanesulfonic acid (0.1 mol/L) is mixed in acetone, and Form 9 immediately precipitates out of solution.

Example 13A: Synthesis of Compound 2 Form 10

Form 10 is produced by either heating Form 12 to 80° C. at 10° C./min or keeping Form 12 under N$_2$ sweeping condition for 1 h in TGA.

Example 14A: Synthesis of Compound 2 Form 11

Form 11 is obtained by heating Form 6 to 80° C. or heating Form 13 to 100° C. in the XRPD.

Example 15A: Synthesis of Compound 2 Form 12

Method A
Slow cooling is conducted by dissolving ca 10 mg of Form 3 in 0.3-1.0 mL solvent or solvent mixture at 60° C. Suspensions are filtered at 60° C. and the filtrate is collected. The saturated solution is cooled from 60° C. to 5° C. in an incubator at a rate of 0.05° C./min. If no precipitation is observed, the solution is subjected to evaporation at RT to induce precipitation. The solids are isolated to provide Form 12 when the solvent or solvent mixture is MeOH/H$_2$O=3:1, n-PrOH/H$_2$O=3:1, or THF/MTBE=3:1.
Method B
Solution vapor diffusion is conducted in solvents at RT by dissolving ca 10 mg of Form 3 in MeOH to obtain a clear solution in a 3-mL vial. The vial is sealed into a 20-mL vial filled with ca 3 mL water, and kept at RT for 5 to 7 days, allowing sufficient time to precipitate. The solids are separated to provide Form 12.

Example 16A: Synthesis of Compound 2 Form 13

Method A:
Form 13 is obtained by heating Form 6 to 80° C. and cooling to RT.

Method B:
Slurry conversion is conducted starting from mixtures of Form 6 and Form 12 at water activity of 0.31 at RT.

Example 17A: Synthesis of Compound 2 Form 14

Solution vapor diffusion is conducted in solvents at RT by dissolving ca 10 mg of Form 3 in MeOH to obtain a clear solution in a 3-mL vial. The vial is sealed into a 20-mL vial filled with ca 3 mL heptane, and kept at RT for 5 to 7 days, allowing sufficient time to precipitate. The solids are separated to provide Form 14.

Example 18A: Synthesis of Compound 2 Form 15

Solution vapor diffusion is conducted in solvents at RT by dissolving ca 10 mg of Form 3 in EtOH to obtain a clear solution in a 3-mL vial. The vial is sealed into a 20-mL vial filled with ca 3 mL IPAc or MTBE, and kept at RT for 5 to 7 days, allowing sufficient time to precipitate. The solids are separated to provide Form 15.

Example 20A: Synthesis of Compound 1 Form 17

Method A:
10.26 mg of Form 16 is suspended in 0.4 mL heptane. The suspension is stirred at RT for about 24 hours. The solid is isolated to obtain Form 17.
Method B:
10.10 mg of Form 16 is suspended in 0.2 mL methyl tert-butyl ether. The suspension is stirred at RT for about 24 hours. The solid is isolated to obtain Form 17.

Example 21A: Synthesis of Compound 1 Form 18

8.17 mg of Form 16 is dissolved in 0.2 mL MeOH. The solution is kept at ambient RT and MeOH is evaporated to provide Form 18.

Example 22A: Synthesis of Compound 1 Form 19

905.61 mg of Form 16 is suspended in 5.0 mL of water. The suspension is stirred at RT for about 4 hours, and the solid is isolated to provide Form 19.

In Examples 3, 4, and 5 below, compound 2 may be amorphous, or a mixture of crystalline forms, or a single crystalline form.

Example 3

The clinical study is a Phase 1/2, Multicenter, Open-Label, Dose-Escalation Study of compound 2 in Subjects with Advanced Solid Tumors, including Glioma, and with Angioimmunoblastic T-cell Lymphoma that harbors an IDH2 Mutation. In this Example, the dose strengths of compound 2 are intended to reflect the free-base equivalent strengths (e.g., when the dose strength of compound 2 is listed as 30 mg, this dose reflects 30 mg of free-base compound 1, which is equivalent to 36 mg of compound 2).

The primary objectives include 1) assessment of the safety and tolerability of treatment with compound 2 administered continuously as a single agent dosed orally on Days 1 to 28 of a 28-day cycle in subjects with advanced solid tumors, including glioma, and in subjects with angioimmunoblastic T-cell lymphoma (AITL); and determination of maximum tolerated dose (MTD) and/or the recommended Phase 2 dose of compound 2 in subjects with advanced solid tumors, including glioma, and in subjects with AITL. Secondary study objectives include 1) description of the dose-limiting toxicities (DLTs) of compound 2 in subjects with advanced malignancies; characterization of the pharmacokinetics (PK) of compound 2 and its metabolite in subjects with advanced malignancies; evaluation of the PK/pharmacodynamic (PD) relationship of compound 2 and 2-hydroxygluturate (2-HG) in blood samples; and characterization of the clinical activity associated with compound 2 in subjects with advanced malignancies.

Exploratory study objectives include 1) evaluation of changes in Ki67 levels in tumor samples; characterization of the PD effects of compound 2 in subjects with advanced malignancies by the assessment of changes in the patterns of cellular differentiation of isocitrate dehydrogenase-2 (IDH2)-mutated tumor cells, and the changes in histone and deoxyribonucleic acid (DNA) methylation profiles in IDH2-mutated tumor cells; characterization of the PD effects of compound 2 in subjects with glioma by the assessment of changes in 2-HG concentration as detected by proton magnetic resonance spectroscopy (1H-MRS) on magnetic resonance images (MRI); evaluation of gene mutation status, global gene expression profiles, and other potential prognostic markers (cytogenetics) in IDH2-mutated tumor cells to explore predictors of anti-tumor activity and/or resistance; evaluation of changes in the metabolic profiles in IDH2-mutated tumor cells; and monitoring of plasma cholesterol and 4β-OH-cholesterol levels as a potential cytochrome P450 (CYP) 3A4 induction marker.

The study is a Phase 1/2, multicenter, open-label, dose-escalation, safety, PK/PD, and clinical activity evaluation of orally administered compound 2 in subjects with advanced solid tumors, including glioma, and in subjects with AITL, that harbor an IDH2 mutation. Subjects with a histologically or cytologically confirmed solid tumor with measurable disease by Response Evaluation Criteria in Solid Tumors (RECIST) v1.1 (Eisenhauer, et al. 2009) for subjects without glioma, or by modified Response Assessment in Neuro-oncology (RANO) criteria (Wen, et al. 2010) for subjects with glioma are eligible, as are subjects with histologically or cytologically confirmed AITL with measurable disease by the revised International Working Group (IWG) response criteria for malignant lymphoma (Cheson, et al. 2007).

Figure 40:
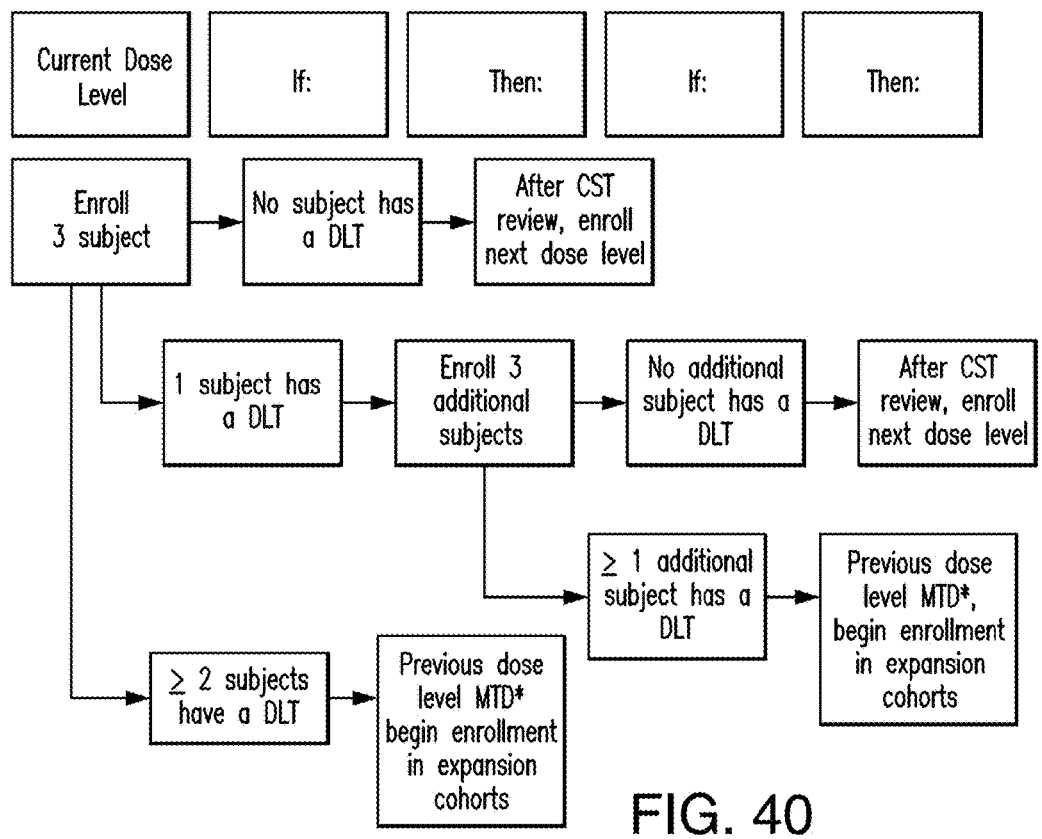
FIG. 40 is a diagram representing the dose escalation scheme. The asterisk indicates that alternatively, a dose level intermediate between the dose level exceeding MTD and the previous does level may be explored and declared MTD if <2 out of 6 subjects experience a DLT at that dose. If only 3 subjects were enrolled at the MTD level, an additional 3 subjects will be enrolled to confirm that <2 of 6 subjects experiences a DLT at this dose.

A schematic of the dose escalation scheme is provided in FIG. 40. The study includes a dose escalation phase to determine MTD followed by expansion cohorts to further evaluate the safety and tolerability of the MTD. The dose escalation phase will utilize a standard "3+3" design. During the dose escalation phase, consented eligible subjects will be enrolled into sequential cohorts of increasing doses of compound 2. Each dose cohort will plan to enroll a minimum of 3 subjects. The first 3 subjects in each cohort enrolled in the dose escalation phase will initially receive a single dose of compound 2 on Day −3 (i.e., 3 days prior to the start of daily dosing) to evaluate concentrations of compound 2, its metabolite, and 2-HG levels; safety also will be assessed, unless notified by the Medical Monitor that this is not required. Continuous daily dosing will begin on C1D1. The initial dosing regimen will be once daily (approximately every 24 hours). If warranted based on the emerging data, alternative dosing schedules (e.g., a loading dose followed by once daily dosing) may be explored in the dose escalation and expansion phases as agreed upon by the Clinical Study Team. If there are multiple subjects in the screening process at the time the third subject within a cohort begins treatment, additional subjects may be enrolled, with approval of the Medical Monitor. For these additional subjects, the Day −3 PK/PD assessments may be considered optional following discussion with the Medical Monitor.

Candidates for the study are adult subjects, 18 years of age or older, with a histologically or cytologically confirmed solid tumor with evaluable disease by RECIST v1.1 for subjects without glioma or by modified RANO criteria for subjects with glioma and subjects with histologically or cytologically confirmed AITL with measurable disease by the revised IWG response criteria for malignant lymphoma.

Confirmation of the primary malignancy is required. Subjects are required to have IDH2 gene-mutated disease, documented by local site testing. Retrospective confirmatory gene mutation analysis will be conducted at a central laboratory to support contemporaneous companion diagnostic development. If local site testing is not available, confirmation can be obtained from the central laboratory prior to treatment, during the screening period.

The safety of dosing will be evaluated by the Clinical Study Team, which is comprised of the Sponsor (Responsible Medical Officer), Study Medical Monitor, and Investigators. The Clinical Study Team will review the emerging safety data from each cohort to determine if dose escalation will occur. If, after the third subject completes the 28-day DLT evaluation period (i.e., Cycle 1), no DLTs are observed, the study will proceed with dose escalation to the next cohort following a review by the Clinical Study Team. If 1 of 3 subjects experiences a DLT during the first cycle, 3 additional subjects will be enrolled in that cohort. If none of the additional 3 subjects experience a DLT (i.e., DLT occurred in <2 of 6 subjects), dose escalation may continue to the next cohort following review by the Clinical Study Team. If 2 or more subjects in a cohort experience DLTs during the first cycle, dose escalation will be halted and the next lower dose level will be declared the MTD. Alternatively, a dose level intermediate between the dose level exceeding MTD and the previous dose level may be explored and declared MTD if <2 out of 6 patients experience a DLT at that dose. If the MTD cohort included only 3 subjects, an additional 3 subjects will be enrolled at that dose level to confirm that <2 of 6 subjects experience a DLT at that dose.

Note that if a given cohort initially enrolled 4 or 5 subjects (i.e., if there were multiple subjects in the screening process at the time the third subject within a cohort began treatment), the same rules for dose escalation apply. If 1 of the 4 (or 5 subjects) experiences a DLT, the cohort will be expanded to include a total of 6 subjects; dose escalation will occur if only 1 of 6 subjects experiences a DLT and will be halted if 2 or more subjects experiences a DLT.

Toxicity severity will be graded according to the National Cancer Institute Common Terminology Criteria for Adverse Events (NCI CTCAE) Version 4.03. A DLT is defined as an event considered related to compound 2 and meeting one of the following criteria: Non-hematologic; All clinically significant non-hematologic toxicities NCI CTCAE≥Grade 3, considered not related to underlying disease or intercurrent illness, with the exception of ≥Grade 3 blood bilirubin increases in subjects with a uridine diphosphate (UDP)-glucuronosyltransferase 1 family, polypeptide A1 (UGT1A1) mutation. In subjects with a UGT1A1 mutation, blood bilirubin increases of >5× upper limit of normal (ULN) may be considered a DLT; Hematologic: drug-related, prolonged myelosuppression of ≥Grade 4 neutropenia or thrombocytopenia lasting beyond Day 28 of Cycle 1 unless related to bone marrow involvement by AITL.

Due to frequent co-morbidities and concurrent medications in the population under study, attribution of adverse events (AEs) to a particular drug can be challenging. Therefore, all AEs that cannot clearly be determined to be unrelated to compound 2 will be considered relevant to determining DLTs and will be reviewed by the Clinical Study Team. The Clinical Study Team also will review any other emergent toxicities that are not explicitly defined by the DLT criteria to determine if any warrant a DLT designation.

The planned study drug doses are summarized in Table 23. The starting dose for this study is 100 mg administered approximately every 24 hours, based on the results of GLP dose range-finding studies and the preliminary results of the ongoing Phase 1 clinical study. Based on evaluation of the safety, tolerability, and PK/PD data of the previous dose levels, it may also be decided that escalation will take place at an intermediate dose level not specified in Table 23.

Increases in the dose of compound 2 for each dose cohort will be guided by an accelerated titration design. The absolute percent increase in the dose across cohorts will be determined by the Clinical Study Team predicated on the type and severity of any toxicity seen in the prior dose cohorts and potentially PK and PK/PD data (but will never exceed 100%) until the MTD is determined. If warranted based on the emerging data, an alternative dosing schedule (e.g., a loading dose followed by once daily dosing) may be explored as agreed upon by the Clinical Study Team. The MTD is the highest dose that causes DLTs in <2 of 6 subjects.

If, after the third subject completes the 28-day DLT evaluation period (i.e., Cycle 1), no DLTs are observed, the study will proceed with dose escalation to the next cohort following safety review by the Clinical Study Team. If 1 of 3 subjects experiences a DLT during the first cycle, 3 additional subjects will be enrolled in that cohort. If none of the additional 3 subjects experience a DLT, dose escalation may continue to the next cohort following safety review by the Clinical Study Team. If 2 or more subjects in a cohort experience DLTs during the first cycle, dose escalation will be halted and the next lower dose level will be declared the MTD. Alternatively, a dose level intermediate between the dose level exceeding MTD and the previous does level may be explored and declared MTD if <2 out of 6 subjects experience a DLT at that dose. If the MTD cohort included only 3 subjects, an additional 3 subjects will be enrolled at that dose level to confirm that <2 of 6 subjects experience a DLT at that dose.

Increases in the dose of compound 2 for each dose cohort will be guided by an accelerated titration design. The absolute percent increase in the dose across cohorts will be determined by the Clinical Study Team predicated on the type and severity of any toxicity seen in the prior dose cohorts and potentially PK and PK/PD data (but will never exceed 100%). If warranted based on the emerging data, an alternative dosing schedule (e.g., a loading dose followed by once daily dosing) may be explored as agreed upon by the Clinical Study Team. The MTD is the highest dose that causes DLTs in <2 of 6 subjects. If no DLTs are identified during the dose escalation phase, dose escalation may continue for at least 2 dose levels above the projected maximum biologically effective exposure, as determined by an ongoing assessment of PK/PD and any observed clinical activity, to determine the recommended Phase 2 dose.

TABLE 23

Planned Dose Escalation Scheme

| Cohort Level | Compound 2 Dose[1, 6] | Number of Subjects |
|---|---|---|
| −1 | 75 mg[2] | 3 to 6 |
| 1 | 100 mg | 3 to 6 |
| 2[3] | 150 mg | 3 to 6 |
| Expansion Cohorts | MTD[4] | 36[5] |

[1]Administered once daily (approximately every 24 hours). If warranted based on the emerging data, alternative dosing schedules (e.g., loading dose followed by once daily dosing) may continue to be explored in the dose escalation and expansion phases as agreed upon by the Clinical Study Team.
[2]If DLTs are observed at Dose Level 1 (100 mg), the dose for the second cohort will be decreased to 75 mg (Dose Level −1).
[3]The absolute percent increase in the dose for subsequent cohorts (beyond Cohort 2) will be determined by the Clinical Study Team predicated on the type and severity of any toxicity seen in the prior dose cohorts, and potentially PK and PK/PD data, until MTD is determined. Dose escalation will never exceed 100%.
[4]Defined as the highest dose that causes DLTs in <1 of 3 or <2 of 6 subjects. If no DLTs are identified, dosing will continue for at least 2 dose levels above the projected maximum biologically effective exposure, as determined by an ongoing assessment of PK/PD and any observed clinical activity to determine the recommended Phase 2 dose.
[5]To include at least 3 cohorts of 12 subjects each.
[6]In this Table, the dose strengths of compound 2 reflect the free-base equivalent strengths (e.g., when the dose strength of compound 2 is listed as 30 mg, this dose reflects 30 mg of free-base compound 1, which is equivalent to 36 mg of compound 2).

Subjects who do not meet any of the treatment withdrawal criteria may continue treatment beyond Cycle 1. To optimize the number of subjects treated at a potentially clinically relevant dose, intra-subject dose escalation will be permitted with approval of the Medical Monitor.

Regularly scheduled teleconferences will serve as a forum for review of safety and other relevant data by the Clinical Study Team. Decisions to escalate the dose will be documented along with a summary of the information supporting the decision.

Following determination of the recommended Phase 2 dose, at least 3 expansion cohorts in solid tumor, glioma, and AITL indications of approximately 12 subjects each will be treated at that dose. The purpose of the expansion cohorts is to evaluate and confirm the safety, tolerability, and clinical activity of the recommended Phase 2 dose in specific disease indications. Subjects enrolled in these cohorts will undergo the same procedures as subjects in the dose escalation cohorts with the exception that the Day −3 to Day 1 PK/PD assessments are optional with Medical Monitor approval.

It is anticipated that the study will be conducted at up to 12 clinical sites in the United States and France.

It is estimated that approximately 45 subjects will be enrolled in the study. This assumes that identification of the MTD requires the evaluation of 2 dose levels of compound 2 with only 3 subjects per dose level, with the exception of the MTD which requires 6 subjects (n=9) and that 12 subjects will be enrolled in the 3 expansion cohorts (n=36). Additional subjects may be needed for cohort expansion during dose escalation, for the replacement of non-evaluable subjects, or for evaluation of alternative dosing regimens other than the planned escalation scheme or the MTD, to optimize the recommended Phase 2 dose.

Following informed consent, subjects will undergo screening procedures within 28 days prior to the start of study drug treatment to determine eligibility. During the screening period, a tumor biopsy should be performed per protocol. If a tumor biopsy cannot be performed during screening, the Medical Monitor is to be notified. In subjects with AITL, a bone marrow biopsy and/or aspirate is to be obtained during screening; subjects with AITL who have skin involvement are also required to have a skin biopsy at screening. Additional screening procedures include medical, surgical, and medication history, radiographic evaluation to determine extent of disease, complete physical examination (including evaluation of hepatomegaly, splenomegaly, lymphadenopathy, and skin involvement in subjects with AITL), vital signs, Eastern Cooperative Oncology Group (ECOG) performance status (PS), 12-lead electrocardiogram (ECG), left ventricular ejection fraction (LVEF), a buccal swab for germ-line mutation analysis, clinical laboratory assessments (hematology, chemistry, coagulation, urinalysis, and serum pregnancy test), blood and urine samples for 2-HG measurement, and blood samples for determination of UGT1A1 mutation status, and plasma cholesterol and 43-OH-cholesterol levels.

Three days prior to starting the continuous daily dosing of compound 2 (Day −3), the first 3 subjects in each cohort in the dose escalation phase will receive a single dose of compound 2 in clinic and have serial blood samples obtained for determination of blood/plasma concentrations of compound 2, its metabolite, and 2-HG unless notified by the Medical Monitor that this is not required. A full 72-hour PK/PD profile will be obtained: subjects will be required to remain at the study site for at least 10 hours on Day −3 and return on Days −2, −1, and 1 for 24-, 48-, and 72-hour samples, respectively. During the in-clinic period on Day −3, clinical observation and serial 12-lead ECGs and vital signs assessments will be conducted over an 8-hour period after the first dose.

Daily treatment with compound 2 will begin on C1D1. The initial dosing regimen will be once daily (approximately every 24 hours). If warranted based on the emerging data, alternative dosing schedules (e.g., loading dose followed by once daily dosing) may be explored in the dose escalation and expansion phases as agreed upon by the Clinical Study Team. Subjects who did not receive the Day −3 dose of compound 2 are to remain in clinic for 8 hours after the C1D1 dose for clinical observation, serial 12-lead ECGs, and vital signs assessments. Safety assessments conducted during the treatment period include physical examination, vital signs, ECOG PS, 12-lead ECGs, evaluation of LVEF, and clinical laboratory assessments (hematology, chemistry, coagulation, and urinalysis).

All subjects will undergo PK/PD assessments over a 10-hour period on C2D1, C4D1, and C6D1. Additional pre-dose urine and/or blood sampling will be conducted on C1D8, C1D15, C1D22, C2D15, C3D1, C3D15, and on Day 1 of all subsequent cycles.

All subjects will undergo computed tomography (CT)/MRI scans to assess the extent of their disease at screening and every 56 days thereafter while on study drug treatment independent of dose delays and/or dose interruptions, and/or at any time when progression of disease is suspected. For subjects with solid tumors other than glioma and subjects with AITL, positron-emission tomography (PET) scans also will be conducted at screening and, if positive, will be conducted post screening at the same time points as CT/MRI scans. For subjects with glioma, 1H-MRS also will be performed at the same time points as CT/MRI scans, and additionally on C1D15 and Day 29, as a part of an exploratory analysis; results of 1H-MRS scans will not be used to make decisions regarding treatment continuation status. The Medical Monitor is to be notified if a site cannot perform 1H-MRS and is enrolling a subject with glioma.

A tumor biopsy (and skin biopsy for subjects with AITL who have active skin involvement at baseline) and a plasma sample will be obtained at screening, at the time of the first assessment of response, at the time of objective response, and at the time of disease progression and/or at the End of Treatment (EOT) Visit. A window of ±3 days around the planned assessment time point is acceptable for all biopsy samples; plasma samples should be obtained at the time of the biopsy. The Medical Monitor is to be notified if a requested tumor biopsy cannot be performed for any reason.

For subjects with AITL, evaluation of the presence or absence of hepatomegaly, splenomegaly, lymphadenopathy, and skin involvement will be conducted throughout treatment as part of the physical examination. Subjects with AITL who experience a complete response (CR) will undergo repeat bone marrow biopsy and/or aspirate to confirm CR.

Subjects may continue treatment with compound 2 until disease progression or development of other unacceptable toxicity. All subjects are to undergo an end of treatment assessment (within approximately 5 days of the last dose of study drug); in addition, a follow-up assessment is to be scheduled 28 days after the last dose.

Response to treatment will be determined by the Investigators based on RECIST v 1.1 (Eisenhauer, et al. 2009) for subjects without glioma or by modified RANO criteria (Wen, et al. 2010) for subjects with gliomas, and by the revised IWG response criteria (Cheson, et al. 2007) for malignant lymphoma for subjects with AITL. Subjects will undergo serial radiographic evaluations to assess the extent of their disease at screening, at specified time points during treatment, and/or at any time when progression of disease is suspected. For subjects with glioma, 1H-MRS will also be performed as a part of an exploratory analysis; results of 1H-MRS scans will not be used to make decisions regarding treatment continuation status. The Medical Monitor is to be notified if a site cannot perform 1H-MRS and is enrolling a subject with glioma.

It is estimated that approximately 45 subjects will be enrolled in the study. Assuming that 50% of patients will not meet inclusion and/or exclusion criteria, i.e., are screen failures, approximately 90 patients will need to be screened to enroll 45. Reasons for screen failure will be captured. Assuming that identification of the MTD requires the evaluation of approximately 2 dose levels of compound 2, and requires the evaluation of only 3 subjects per dose level with the exception of the MTD which requires 6 subjects, then 9 subjects will be enrolled during the dose escalation part of the study. It is anticipated that at least 3 cohorts of 12 additional subjects with specific solid tumors, glioma, and AITL (total 36 subjects) will be enrolled in the cohort expansion part of the study. Additional subjects may be needed for cohort expansion during dose escalation, for the replacement of non-evaluable subjects, or for evaluation of alternative dosing regimens other than the planned escalation scheme or the MTD, to optimize the recommended Phase 2 dose.

Subjects must meet all of the following criteria to be enrolled in the study:
1. Subject must be ≥18 years of age.
2. Subjects must have a histologically or cytologically confirmed advanced solid tumor, including glioma, or AITL that has recurred or progressed following standard therapy, or that has not responded to standard therapy.
3. Subjects must have documented IDH2 gene-mutated disease based on local site testing. (Centralized testing will be performed retrospectively.)
4. Subject must have measurable disease by RECIST v1.1 for subjects with solid tumors without glioma, by modified RANO criteria for subjects with glioma, or by the revised IWG criteria for subjects with AITL.
5. Subjects must be amenable to serial peripheral blood sampling, urine sampling, and biopsies.

6. Subjects must be able to understand and willing to sign an informed consent. A legally authorized representative may consent on behalf of a subject who is otherwise unable to provide informed consent, if acceptable to, and approved by, the site and/or site's Institutional Review Board (IRB).
7. Subjects must have ECOG PS of 0 to 2.
8. Subjects must have expected survival of ≥3 months.
9. Subjects other than those with AITL must have adequate bone marrow function as evidenced by:
   a. Absolute neutrophil count ≥1.0×10$^9$/L;
   b. Hemoglobin ≥9 g/dL (Subjects are allowed to be transfused to this level)
   c. Platelets ≥50×10$^9$/L.
10. Subjects must have adequate hepatic function as evidenced by:
    a. Serum total bilirubin ≤1.5× upper limit of normal (ULN), unless considered due to Gilbert's disease, a gene mutation in UGT1A1, or disease involvement, following approval by the Medical Monitor;
    b. Aspartate aminotransferase (AST), alanine aminotransferase (ALT), and alkaline phosphatase (ALP)≤2.5×ULN. For subjects with bone metastases and/or suspected disease-related liver or biliary involvement, ALP must be ≤5×ULN.
11. Subjects must have adequate renal function as evidenced by:
    a. Serum creatinine ≤2.0×ULN
    OR
    b. Creatinine clearance >40 mL/min based on the Cockroft-Gault glomerular filtration rate (GFR) estimation: (140−Age)×(weight in kg)×(0.85 if female)/72× serum creatinine
12. Subjects must be recovered from any clinically relevant toxic effects of any prior surgery, radiotherapy, or other therapy intended for the treatment of cancer. (For example, subjects with residual Grade 1 toxicity or stable Grade 2 peripheral neuropathy due to prior chemotherapy are allowed with approval of the Medical Monitor.)
13. Female subjects with reproductive potential must have a negative serum pregnancy test within 7 days prior to the start of therapy. Subjects with reproductive potential are defined as one who is biologically capable of becoming pregnant. Women of childbearing potential as well as fertile men and their partners must agree to abstain from sexual intercourse or to use an effective form of contraception during the study and for 90 days (females and males) following the last dose of compound 2.
14. Previous allogeneic stem cell transplant is allowed only if subjects are >100 days from stem cell transplant and do not have uncontrolled acute or chronic graft-versus-host disease.

Subjects who meet any of the following criteria will not be enrolled in the study:
1. Subjects who received systemic anticancer therapy or radiotherapy <21 days prior to their first day of study drug administration.
2. Subjects who received an investigational agent <14 days prior to their first day of study drug administration. In addition, the first dose of compound 2 should not occur before a period ≥5 half-lives of the investigational agent has elapsed.
3. Subjects taking the following sensitive cytochrome P450 (CYP) substrate medications that have a narrow therapeutic range are excluded from the study unless they can be transferred to other medications prior to enrolling: paclitaxel (CYP2C8), warfarin, phenytoin (CYP2C9), S-mephenytoin (CYP2C19), thioridazine (CYP2D6), theophylline and tizanidine (CYP1A2).
4. Subjects taking the P-glycoprotein (P-gp) and breast cancer resistant protein (BCRP) transporter-sensitive substrates digoxin and rosuvastatin should be excluded from the study unless they can be transferred to other medications prior to enrolling.
5. Subjects for whom potentially curative anticancer therapy is available.
6. Subjects who are pregnant or breast feeding.
7. Subjects with an active severe infection that required anti-infective therapy or with an unexplained fever >38.5° C. during screening visits or on their first day of study drug administration (at the discretion of the Investigator, subjects with tumor fever may be enrolled).
8. Subjects with known hypersensitivity to any of the components of compound 2.
9. Subjects with New York Heart Association (NYHA) Class III or IV congestive heart failure or LVEF<40% by echocardiogram (ECHO) or multi-gated acquisition (MUGA) scan within approximately 28 days of C1D1.
10. Subjects with a history of myocardial infarction within the last 6 months.
11. Subjects with uncontrolled hypertension (systolic blood pressure >180 mmHg or diastolic blood pressure >100 mmHg) are excluded. Subjects requiring 2 or more medications to control hypertension are eligible with Medical Monitor approval.
12. Subjects with known unstable or uncontrolled angina pectoris.
13. Subjects with a known history of severe and/or uncontrolled ventricular arrhythmias.
14. Subjects with heart-rate corrected QT (QTc) interval ≥450 ms or other factors that increase the risk of QT prolongation or arrhythmic events (e.g., heart failure, hypokalemia, family history of long QT interval syndrome). Subjects with right bundle branch block and a prolonged QTc interval should be reviewed by the Medical Monitor for potential inclusion.
15. Patients taking medications that are known to prolong the QT interval.
16. Subjects with known infection with human immunodeficiency virus (HIV) or active hepatitis B or C.
17. Subjects with any other medical or psychological condition, deemed by the Investigator to be likely to interfere with a subject's ability to sign informed consent, cooperate, or participate in the study.
18. Subjects with known dysphagia, short-gut syndrome, gastroparesis, or other conditions that limit the ingestion or gastrointestinal absorption of drugs administered orally.
19. Subjects with brain metastases that are untreated, symptomatic, or require therapy to control symptoms; or any radiation, surgery, or other therapy, including those used to control symptoms, within 2 months of first dose. Subjects with glioma who are on a stable, steroid-dosing regimen prior to screening MRI may be permitted to enroll with Medical Monitor approval.
20. In subjects with AITL, evidence of meningeal or cerebral disease or a history of progressive multifocal leukoencephalopathy.
21. Radiotherapy involving <25% of the hematopoietically active bone marrow within 21 days preceding first dose of study treatment.

22. Radiotherapy involving ≥25% of the hematopoietically active bone marrow within 42 days preceding first dose of study treatment.

Compound 2 will be provided as either as tablet formulation 1 (5, 10, 50, and 200 mg free-base equivalent strength) or tablet formulation 2 (25, 50, 100 and/or 150 mg free-base equivalent strength) to be administered orally.

The first 3 subjects in each cohort in the dose escalation portion of the study will receive a single dose of study drug on Day −3, unless notified by the Medical Monitor that this is not required; their next dose of study drug will be administered on C1D1 at which time subjects will start dosing once daily (approximately every 24 hours) on Days 1 to 28 in 28-day cycles, with plans to explore alternative dosing regimens if warranted based on the emerging data. Starting with C1D1, dosing is continuous; there are no inter-cycle rest periods. Subjects who are not required to undergo the Day −3 PK/PD assessments will initiate dosing with compound 2 on C1D1.

All subjects will receive compound 2 administered orally once daily (approximately every 24 hours). If warranted based on the emerging data, an alternative dosing schedule (e.g., a loading dose followed by once daily dosing), may continue to be explored in the dose escalation and expansion phases as agreed upon by the Clinical Study Team. The dose of compound 2 for each subject will be based on the assigned cohort.

Each dose cohort will initially enroll 3 subjects. If there are multiple subjects in the screening process at the time the third subject within a cohort begins study drug treatment, additional subjects may be enrolled with approval of the Medical Monitor.

Additional subjects may be needed for cohort expansion during dose escalation, for the replacement of subjects who are not evaluable for PK/PD, safety or clinical activity, or for evaluation of alternative dosing regimens other than the planned escalation scheme or the MTD, to optimize the recommended Phase 2 dose.

The dose of compound 2 administered to a subject will be dependent upon which dose cohort is open for enrollment when the subject qualifies for the study. The starting dose of compound 2 to be administered to the first cohort of subjects is 100 mg administered orally once a day.

Compound 2 will be administered orally once daily (approximately every 24 hours) on Days 1 to 28 in 28-day cycles. The initial dosing regimen will be once daily (approximately every 24 hours). If warranted based on the emerging data, an alternative dosing schedule (e.g., a loading dose followed by once daily dosing), may continue to be explored in the dose escalation and expansion phases as agreed upon by the Clinical Study Team. Starting with C1D1, dosing is continuous; there are no inter-cycle rest periods. Subjects who do not meet any of the treatment withdrawal criteria may continue treatment beyond Cycle 1.

Subjects are required to fast, meaning each daily dose (including days which involve PK/PD blood sampling) is to be taken 2 hours after fasting (water is allowed). Food intake should be avoided for at least 1 hour after study drug administration. Fasting during dosing may be discontinued once results of an ongoing food effect study are complete.

Subjects should be instructed to take their daily dose at approximately the same time each day. Each dose should be taken with a glass of water and consumed over as short a time as possible. Subjects should be instructed to swallow tablets whole and to not chew the tablets. For subjects who have difficulty swallowing tablet(s), the Medical Monitor should be contacted to discuss administration.

If the subject forgets to take the daily morning dose, then they should take compound 2 within 12 hours after the missed dose. If more than 12 hours have elapsed, then that dose should be omitted, and the subject should resume treatment with the next scheduled dose.

The following therapies are not permitted during the study:
  Other antineoplastic therapy. If alternative therapy is required for treatment of the subject's disease, the subject should be discontinued from study drug treatment.
  Corticosteroids, with the exception of topical cutaneous, ophthalmic, nasal, and inhalational steroids. (Short course steroid therapy to treat co-morbidities, the use of chronic low dose steroids to treat an underlying medical condition that is not a malignancy, and steroid treatment to control symptoms in subjects with glioma, will be permitted with approval of the Medical Monitor.) (Corticosteroids to treat AITL-associated skin rash and/or arthralgias may be permitted with approval of the Medical Monitor.)
  Medications that are known to prolong QT interval: amiodarone, arsenic trioxide, astemizole, azithromycin, bepridil, chloroquine, chlorpromazine, cisapride, citalopram, clarithromycin, disopyramide, dofetilide, domperidone, droperidol, erythromycin, escitalopram, flecainide, halofantrine, haloperidol, ibutilide, levomethadyl, mesoridazine, methadone, moxifloxacin, pentamidine, pimozide, probucol, procainamide, quinidine, sevoflurane, sotalol, sparfloxacin, terfenadine, thioridazine, or vandetanib.
  Sensitive CYP substrate medications that have a narrow therapeutic range: paclitaxel (CYP2C8) warfarin, phenytoin (CYP2C9), S-mephenytoin (CYP2C19), thioridazine (CYP2D6), theophylline and tizanidine (CYP1A2). Coadministration of other CYP2C8, 2C9, 2C19, 2D6, and 1A2 substrates should be used only if medically necessary.
  P-pg and BCRP transporter-sensitive substrates digoxin and rosuvastatin. Coadministration of other P-gp or BCRP substrates should be used only if medically necessary.

Subjects should avoid taking antacids, $H_2$ blockers, or proton pump inhibitors while taking compound 2. Given the solubility profile of compound 2, the exposure can be much lower for subjects with elevated gastric pH.

Medications and treatments other than those specified above are permitted during the study. All intercurrent medical conditions and complications of the underlying malignancy will be treated at the discretion of the Investigator according to acceptable local standards of medical care. Subjects should receive analgesics, antiemetics, anti-infectives, antipyretics, and blood products as necessary. All concomitant medications, including transfusions of blood products, will be recorded on the eCRF.

Growth factors (granulocyte colony-stimulating factor [G-CSF], granulocyte-macrophage colony-stimulating factor [GM-CSF]) can be used to support subjects who have developed dose-limiting Grade 4 neutropenia or Grade 3 neutropenia with fever and/or infection. The use of erythropoiesis stimulating agents is permitted according to the American Society of Clinical Oncology Guidelines (Rizzo, et al. 2010).

A stable dose of steroids to control symptoms of brain metastases or for subjects with glioma is allowed with Medical Monitor approval. Corticosteroids to treat AITL-associated skin rash and/or arthralgias may be permitted with approval of the Medical Monitor.

All concomitant medications, including any procedures performed during the study, including those used to treat AEs, are to be reported on the eCRF.

Compound 2 may cause sensitivity to direct and indirect sunlight. The subjects should be warned to avoid direct sun exposure. When exposure to sunlight is anticipated for longer than 15 minutes, the subject should be instructed to apply factor 30 or higher sunscreen to exposed areas and wear protective clothing and sunglasses.

Criteria for Evaluation

Safety

A complete physical examination, including assessment of weight, will be obtained at screening and at the EOT visit. A limited physical examination, including assessment of weight, will be completed on Day −3 (for subjects undergoing 72-hour PK/PD profile), on Days 1, 8 and 15 of Cycle 1, and on Day 1 of each treatment cycle thereafter. Height will be obtained at the screening visit. For subjects with AITL, all physical examinations will include an assessment of the presence or absence of hepatomegaly, splenomegaly, lymphadenopathy and skin involvement.

Determination of ECOG PS will be performed at screening, on Day −3 (for subjects undergoing 72-hour PK/PD profile), on Days 1 and 15 of Cycle 1, on Day 1 of each treatment cycle thereafter, at the EOT visit, and at the Follow-up visit.

A 12-lead ECG is to be obtained at screening, on Days 8, 15, and 22 of Cycle 1, on Days 1 and 15 of Cycle 2, on Day 1 of each treatment cycle thereafter, at the End of Treatment visit, and at the Follow-up visit. Additionally, serial 12-lead ECGs are to be obtained following the first dose of study treatment (i.e., on Day −3 for subjects undergoing the 72-hour PK/PD profile or on C1D1 for subjects who do not attend the Day −3 assessment) at the following times: predose, and 30±10 minutes and 2, 4, 6, and 8 hours (±15 minutes) post dose. Serial ECGs should be obtained following vital signs assessments. The 12-lead ECGs should be obtained in triplicate following 3 minutes of recumbency or semi-recumbency.

Subjects are to have LVEF determined by ECHO or MUGA within 28 days of C1D1; repeat assessments are to be conducted on C3D1, Day 1 of every other treatment cycle thereafter (e.g., C5D1, D7D1, etc.), at the EOT visit, and at the Follow-up visit. The same procedure to evaluate LVEF should be conducted throughout the study.

The following safety laboratory parameters are to be determined:

Hematology: hematocrit, hemoglobin, red blood cell (RBC) count, white blood cell (WBC) count with differential, platelet count Serum Chemistry: sodium, potassium, chloride, calcium, magnesium, phosphorus, $CO_2$, albumin, total protein, glucose, blood urea nitrogen (BUN), creatinine, uric acid, lactate dehydrogenase (LDH), ALP, ALT, AST, total bilirubin, direct bilirubin, indirect bilirubin Serum Studies: creatinine kinase, cardiac troponin, amylase, and lipase Coagulation Studies: prothrombin time (PT), activated partial thromboplastin time (aPTT), international normalized ratio (INR)

Urinalysis: Color and appearance; pH, specific gravity, ketones, protein, glucose, bilirubin, nitrite, urobilinogen, and occult blood by dipstick; and microscopic inspection of sediment.

Blood for hematology and serum chemistries is to be obtained at screening, Day −3 (for subjects undergoing 72-hour PK/PD profile), Days 1, 8, 15, and 22 of Cycle 1, on Days 1 and 15 of Cycles 2 and 3, on Day 1 of each treatment cycle thereafter, and at the EOT visit.

Blood for creatine kinase, cardiac troponin, amylase, and lipase is to be obtained at screening, Day −3 (for subjects undergoing 72-hour PK/PD profile), on Day 1 of each treatment cycle, and at the End of Treatment visit.

Blood for coagulation studies is to be obtained at screening, Day −3 (for subjects undergoing 72-hour PK/PD profile), Days 1 and 15 of Cycle 1, Day 1 of each treatment cycle thereafter, and at the End of Treatment visit.

Urine for urinalysis is to be obtained at screening, Day −3 (for subjects undergoing 72-hour PK/PD profile), Days 1 and 15 of Cycle 1, Day 1 of each treatment cycle thereafter, and at the End of Treatment visit.

Pregnancy Test: All women of child-bearing potential must have a negative pregnancy test to be eligible. A serum pregnancy test will be performed at screening; a urine pregnancy test must be conducted and confirmed negative on the first day of study drug administration before dosing (Day −3 for subjects undergoing 72-hour PK/PD profile or on C1D1).

Each subject must be carefully monitored for the development of any AEs throughout the study from signing of the informed consent to 28 days after the last dose. In addition, SAEs that are assessed as possibly or probably related to study treatment that occur >28 days post-treatment also are to be reported.

Tumor biopsy (and skin biopsy for subjects with AITL who have active skin involvement at baseline) and plasma sampling will be performed at screening, at the time of the first disease assessment (Day 56), at the time of objective response, and at any time disease progression is suspected and/or at the EOT visit. A window of ±3 days around the planned assessment time point is acceptable for all biopsy samples; plasma samples should be obtained at the time of the biopsy. The Medical Monitor is to be notified if a requested tumor biopsy cannot be performed for any reason.

Tumor tissue will be evaluated locally at the site for morphology, cellular differentiation via hematoxylin and eosin (H & E) staining, and for Ki67 levels via immunohistochemistry (IHC). In addition, samples of tumor tissue will be submitted to the Sponsor (or designee) for evaluation of IDH2 gene mutation status, 2-HG levels and for specific cell-type markers via IHC, gene expression profiling, and histone and DNA methylation. Tumor samples may also be evaluated for metabolic profiling, and, if feasible, intratumoral compound 2 levels.

Plasma samples obtained at the time of tumor biopsy will be evaluated by the Sponsor (or designee) for IDH mutational status and metabolic profiling.

Clinical Activity Assessments

The clinical activity of compound 2 will be evaluated by assessing response to treatment according to RECIST v1.1 (Eisenhauer, et al. 2009) for subjects with solid tumors without glioma, by modified RANO criteria for subjects with glioma (Wen, et al. 2010), or by the revised IWG criteria for subjects with AITL (Cheson, et al. 2007).

Computed tomography or MRI scans to obtain tumor measurements are to be conducted in all subjects at screening and every 56 days thereafter while on study drug treatment, independent of dose-delays and/or dose interruptions, and/or at any time when progression of disease is suspected. An assessment also will be conducted at the EOT visit for subjects who discontinue the study due to reasons other than disease progression.

For subjects with solid tumors (other than glioma) and subjects with AITL, a positron-emission tomography (PET)/CT scan is required at screening. If the subject has PET-avid disease at baseline, serial PET/CT scans should be obtained on the same schedule as CT/MRI scans. Results of PET imaging will be exploratory in nature for subjects with solid tumors as response will be based on RECIST criteria.

For subjects with glioma, 1H-MRS will also be performed as a part of an exploratory analysis on the same schedule as CT/MRI scans with additional scans on C1D15 and Day 29; results of 1H-MRS scans will not be used to make decisions regarding treatment continuation status. The Medical Monitor is to be notified if a site cannot perform 1H-MRS and is enrolling a subject with glioma.

For subjects with AITL, bone marrow biopsies and/or aspirates are to be obtained at screening and, if positive at screening, are to be repeated at the end of Cycle 1 prior to Cycle 2 (C1D28 or C2D1) and at the time of CR to confirm the response. Bone marrow aspirates and core sampling should be performed according to standard of care and analyzed at the local site's laboratory in accordance with the International Council for Standardization in Hematology (ICSH) Guidelines (Lee, et al. 2008).

For subjects with AITL who have known or suspected active skin involvement, a ≥6 mm punch biopsy is required at screening, at the first disease assessment conducted on Day 56, at the time of objective response, and at disease progression and/or at the EOT visit. A window of ±3 days around the planned assessment time point is acceptable for all biopsy samples. The extent of skin disease, including evaluation of total body surface area (BSA) involved and CTCAE grade of the rash, will be conducted at screening, at each disease assessment, at the time of objective response, and at disease progression and/or at the EOT visit. Total BSA will be evaluated based on the following percent involvement by anatomic structure (rule of nines): anterior and posterior head (each 4.5%), anterior and posterior torso (each 18%), anterior and posterior leg (each 9% for each leg), anterior and posterior arm (each 4.5% for each arm), and genitalia/perineum (1%).

For subjects with solid tumors other than glioma, tumor lesions are to be categorized as measurable versus non-measurable and target versus non-target based on RECIST v1.1 (Eisenhauer, et al. 2009).

Tumor Lesions:

Must be accurately measured in at least one dimension (longest diameter in the plane of measurement is to be recorded) with a minimum size of:
- 10 mm by CT scan (CT scan slice thickness no greater than 5 mm).
- 10 mm caliper measurement by clinical exam (lesions which cannot be accurately measured with calipers should be recorded as non-measurable).
- 20 mm by chest X-ray.

Malignant Lymph Nodes:

To be considered pathologically enlarged and measurable, a lymph node must be ≥15 mm on the short axis when assessed by CT scan.

All other lesions, including small lesions (longest diameter <10 mm or pathological lymph nodes with ≥10 to <15 mm short axis) as well as truly non-measurable lesions, including leptomeningeal disease, ascites, pleural or pericardial effusion, inflammatory breast disease, lymphangitic involvement of skin or lung, abdominal masses/abdominal organomegaly identified by physical exam that is not measurable by reproducible imaging techniques.

When more than one measurable lesion is present at baseline all lesions up to a maximum of 5 total (and a maximum of 2 lesions per organ) representative of all involved organs should be identified as target lesions and measured at baseline.

Target lesions should be selected on the basis of their size (lesions with the longest diameter), be representative of all involved organs, but in addition should be those that lend themselves to reproducible repeated measurements.

Pathological lymph nodes which are defined as measurable and identified as target lesions must have a short axis of ≥15 mm by CT scan. Only the short axis of these nodes contributes to the baseline sum.

A sum of the diameters (longest for non-nodal lesions, short axis for nodal lesions) for all target lesions will be calculated and reported as the baseline sum diameters. The baseline sum diameters will be used as reference to further characterize any objective tumor regression in the measurable dimension of the disease.

All other lesions (or sites of disease) including pathological lymph nodes should be identified as non-target lesions and should also be recorded at baseline. Measurements are not required and these lesions should be followed as 'present', 'absent' or 'unequivocal progression'. The following criteria outlined in Table 24 and Table 25 will be used to assess response to treatment.

TABLE 24

RECIST Disease Response Criteria for Target and Non-target Lesions

| | Response Criteria | |
|---|---|---|
| Category | Target Lesions | Non-Target Lesions/Tumor Markers |
| Complete Response (CR) | Disappearance of all target lesions. Any pathological lymph nodes (whether target or non-target) must have reduction in short axis to <10 mm | Disappearance of all non-target lesions, and normalization of tumor marker level All lymph nodes must be non-pathological in size (<10 mm short axis). |
| Partial Response (PR) | A ≥30% decrease in the sum of the diameter of target lesions, taking as reference the baseline sum diameter | N/A |

TABLE 24-continued

RECIST Disease Response Criteria for Target and Non-target Lesions

| | Response Criteria | |
|---|---|---|
| Category | Target Lesions | Non-Target Lesions/Tumor Markers |
| Stable Disease (SD)/ Incomplete Response | Neither sufficient shrinkage to qualify for partial response nor sufficient increase to qualify for progressive disease, taking as reference the smallest sum diameter since the treatment started | Persistence of one or more non-target lesion(s) and/or Maintenance of tumor marker levels above the normal limits |
| Progressive Disease (PD) | A ≥20% increase in the sum of the diameter of target lesions, taking as reference the smallest sum diameter recorded since the treatment started. In addition to the relative increase of 20%, the sum must also demonstrate an absolute increase of at least 5 mm, or The appearance of one or more new lesions | Appearance of one or more new lesions, and/or Unequivocal progression of existing non-target lesions |

TABLE 25

RECIST Overall Disease Response Criteria

| Target Lesions | Non-Target Lesions | New Lesions | Overall Response |
|---|---|---|---|
| CR | CR | No | CR |
| CR | Incomplete response/SD | No | PR |
| PR | Incomplete response/Non-PD | No | PR |
| SD | Incomplete response/Non-PD | No | SD |
| PD | Any | Yes or no | PD |
| Any | PD | Yes or no | PD |
| Any | Any | Yes | PD |

This trial will utilize the criteria recently proposed by the Response Assessment in Neuro-Oncology (RANO) working group (Wen, et al. 2010). The RANO criteria updates its established predecessor, the modified Macdonald criteria (Macdonald, et al. 1990).

Specific lesions must be evaluated serially, and comparative analysis of changes in the area of contrast enhancement, as well as the non-enhancing component, should be performed. As with the Macdonald criteria (Macdonald, et al. 1990), the product of the maximal cross-sectional enhancing diameters will be used to determine the size of the contrast-enhancing lesions.

Measurable Disease:
  Bidimensionally, contrast-enhancing, measurable lesions with clearly defined margins by CT or MRI scan, with a minimal diameter of 1 cm, and visible on 2 axial slices which are at least 5 mm apart with 0 mm skip. Measurement of tumor around a cyst or surgical cavity, if necessary, requires a minimum thickness of 3 mm. If there are too many measurable lesions to measure at each evaluation, the investigator must choose the largest 2 to be followed before a subject is entered on study. The remaining lesions will be considered non-measureable for the purpose of objective response determination.

Non-Measurable Evaluable Disease:
  Unidimensionally measurable lesions, masses with margins not clearly defined, lesions with maximal diameter <1 cm.

Number of Lesions:
  If there are multiple contrast-enhancing lesions, a minimum of the 2 largest lesions should be measured, and the sum of the products of the perpendicular diameters of these lesions should be determined, similar to the criteria proposed for systemic tumors in RECIST v1.1. However, given the heterogeneity of high-grade gliomas and the difficulty in measuring some lesions, a maximum of 5 of the largest lesions may be measured. In general, the largest enlarging lesion(s) should be selected. However, emphasis should also be placed on lesions that allow reproducible repeated measurements. Occasionally, the largest lesions may not lend themselves to reproducible measurements, and the next largest lesions that can be measured reproducibly should be selected. For subjects with recurrent disease who have multiple lesions of which only 1 or 2 are increasing in size, the enlarging lesions will be considered the target lesions for evaluation of response. The other lesions will be considered non-target lesions and should also be recorded.

Response/Progression Categories:
  Note that all measurable and nonmeasurable lesions must be assessed using the same techniques throughout the study.
  Unless progression is observed, objective response can only be determined when all measurable and non-measurable lesions are assessed.
  For assessment of low-grade glioma, the RANO high-grade glioma criteria as outlined below will be used; however, tumor size should be determined by the product of the maximal cross-sectional fluid attenuated inversion recovery (FLAIR) diameters instead of enhancing diameters.

Complete Response (CR):
  All of the following criteria must be met:
  Complete disappearance of all enhancing measurable and non-measurable disease sustained for at least 4 weeks. In the absence of a confirming scan 4 weeks later, this scan will be considered stable disease.
  No new lesions.
  Participants must not be on no steroids or be on physiologic replacement doses only.
  Stable or improved non-enhancing (T2/FLAIR) lesions
  Stable or improved clinically, for clinical signs and symptoms present at baseline and recorded to be disease related.

Subjects with only non-measurable disease cannot have a CR. The best response possible is stable disease.

Partial Response (PR):
 All of the following criteria must be met:
  ≥50% decrease compared to baseline in the sum of products of perpendicular diameters of all measurable enhancing lesions sustained for at least 4 weeks. In the absence of a confirming scan 4 weeks later, this scan will be considered stable disease.
 No progression of non-measurable disease.
 No new lesions.
 The steroid dose at the time of the scan evaluation should be no greater than the dose at time of baseline scan.
 Stable or improved non-enhancing (T2/FLAIR) lesions on same or lower dose of corticosteroids compared to baseline scan.
 Stable or improved clinically, for clinical signs and symptoms present at baseline and recorded to be disease related.

Subjects with only non-measurable disease cannot have a PR. The best response possible is stable disease.

Stable Disease (SD):
 All of the following criteria must be met:
 Does not qualify for CR, PR, or progression.
 Stable non-enhancing (T2/FLAIR) lesions on same or lower dose of corticosteroids compared to baseline scan. In the event that the corticosteroid dose was increased for new symptoms and signs without confirmation of disease progression on neuroimaging, and subsequent follow-up imaging shows that this increase in corticosteroids was required because of disease progression, the last scan considered to show stable disease will be the scan obtained when the corticosteroid dose was equivalent to the baseline dose.
 Stable clinically.

Progressive Disease (PD)
 The following criterion must be met:
  ≥25% increase in sum of the products of perpendicular diameters of enhancing lesions compared with the smallest tumor measurement obtained either at baseline (if no decrease) or best response on stable or increasing doses of corticosteroids and/or one or more of the of the following:
 Significant increase in T2/(FLAIR) non-enhancing lesion on stable or increasing doses of corticosteroids compared to baseline scan or best response following initiation of therapy, not due to co-morbid events (radiation therapy, demyelination, ischemic injury, infection, seizures, post-operative changes, or other treatment effects).
 Any new lesion
 Clear clinical deterioration not attributable to other causes apart from the tumor (e.g., seizures, medication side effects, complications of therapy, cerebrovascular events, infection, etc.) or changes in corticosteroid dose.
 Failure to return for evaluation due to death or deteriorating condition
 Clear progression of nonmeasurable disease.
 Rarely, unequivocal progression of a non-target lesion requiring discontinuation of therapy or development of a new contrast-enhancing lesion may occur, even in the setting of stable disease or partial response in the target lesions. These changes will qualify as progression.

TABLE 26

Summary of RANO Response Criteria

| Criterion: | CR | PR | SD | PD[a] |
|---|---|---|---|---|
| T1 Gadolinium enhancing disease | None | ≥50% decrease | <50% decrease <25% increase | ≥25% increase* |
| T2/FLAIR | Stable or decrease | Stable or decrease | Stable or decrease | Increase* |
| New Lesion | None | None | None | Present* |
| Corticosteroids | None | Stable or decrease | Stable or decrease | NA[b] |
| Clinical Status | Stable or improved | Stable or improved | Stable or decline | Decline* |
| Requirement for Response | All | All | All | Any* |

[a]Progression occurs when any of the criteria with * is present
[b]NA: Increase in corticosteroids alone will not be taken into account in determining progression in the absence of persistent clinical deterioration.

Evaluation of response to treatment in subjects with AITL is to be based on the revised IWG criteria (Cheson, et al. 2007). Lymphadenopathy is the primary abnormality exhibited in lymphoma. Additionally, sites of associated extranodal involvement may be present in the liver, spleen, stomach, bowel, skin, nasal cavity, and other anatomical locations (i.e., extranodal lesions). Diseased nodes, nodal masses, and extranodal lesions identified at baseline for serial imaging are to be classified as Index or Non-Index lesions and further classified as "nodal" or "extranodal" as detailed below.

Identification of Index and Non-Index Lesions

Based on the IWG criteria, abnormal lymph nodes or nodal masses were to be identified based on the following:
 1. Clear measurability in at least 2 perpendicular dimensions with a minimum measurement of >10 mm for the longest dimension;
 2. Location in as disparate regions of the body as possible; and
 3. From mediastinal and retroperitoneal areas of disease whenever these sites were involved.

Index Lesions are to be measured by the maximal linear dimension (major axis) of the lesion and the longest perpendicular dimension (minor axis). The total burden of disease per time point is to be determined using the sum of the products of the diameters (SPD) of index lesions. A maximum of 6 nodal index lesions representing abnormal lymph nodes and/or nodal masses are to be identified. Radiologists are strongly encouraged to select the largest nodes (while following the anatomical location criteria).

Additionally, evidence of measurable disease that is consistent with lymphoma, but exclusive of lymph nodes (>10 mm at baseline) are to be identified as Extranodal Index Lesions, e.g., hepatic nodules, splenic nodules, skin lesions, or any associated pathology found outside the lymphatic system. A maximum of 10 index lesions are to be selected if nodal plus extranodal disease is present or if only extranodal disease is present.

All other assessable disease is to be identified as Non-Index Lesions. The presence, absence, or unequivocal progression of non-index lesions and the appearance of any new lesion are to be noted throughout the study.

TABLE 27

IWG Disease Response Criteria

Response Criteria

| Category | Definition | Nodal Masses | Extra Nodal Masses, Including Spleen, Liver, Skin | Bone Marrow |
|---|---|---|---|---|
| Complete Response (CR) | Disappearance of all evidence of disease | (a) FDG-avid or PET positive prior to therapy; mass of any size permitted if PET negative<br>(b) Variably FDG-avid or PET negative; regression to normal size on CT (≤2.5 cm in the greatest transverse diameter for nodes >1.5 cm at baseline). Previously involved nodes that were 1.1 to 1.5 cm in their long axis and more than 1.0 cm in their short axis before treatment must have decreased to ≤1.0 cm in their short axis after treatment. | Not palpable, nodules disappeared | Infiltrate cleared on repeat biopsy; if indeterminate by morphology, immunohistochemistry should be negative |
| Partial Response (PR) | Regression of measurable disease and no new sites | (a) ≥50% decrease in SPD from baseline of all index lesions (both nodal and extranodal lesions).;<br>(b) No obvious increase (no unequivocal progression) in non-index lesions/disease.<br>(c) FDG-avid or PET positive prior to therapy; one or more PET positive at previously involved site<br>(d) Variably FDG-avid or PET negative; regression on CT<br>(e) No increase in size of liver or spleen | | Irrelevant if positive prior to therapy; cell type should be specified |
| Stable Disease (SD) | Failure to attain CR/PR or PD | (a) FDG-avid or PET positive prior to therapy; PET positive at prior sites of disease and no new sites on CT or PET<br>(b) Variably FDG-avid or PET negative; no change in size of previous lesions on CT | | |
| Relapsed Disease or Progressive Disease (PD) | Any new lesion or increase by ≥50% of previously involved sites from nadir | Appearance of a new lesion(s) >1.5 cm in any axis, ≥50% increase in SPD of more than one node, or ≥50% increase in longest diameter of a previously identified node >1 cm in short axis<br>Lesions PET positive if FDG-avid lymphoma or PET positive prior to therapy | >50% increase from nadir in the SPD of any previous lesions | New or recurrent involvement |

Pharmacokinetic Assessments

Blood Sample Collection and Pharmacokinetic Measurements During Dose Escalation

Serial blood samples will be drawn before and after dosing with compound 2 in order to determine circulating plasma concentrations of compound 2 (and, if technically feasible, the metabolite of compound 2). The blood samples will also be used for the determination of 2-HG concentrations and metabolic profiling, and for evaluation of cholesterol and 4β-OH-cholesterol levels.

For the first 3 subjects enrolled in a cohort during the dose escalation phase, a single dose of compound 2 will be administered on Day −3 (i.e., 3 days prior to their scheduled C1D1 dose), unless notified by the Medical Monitor that this is not required. Blood samples will be drawn prior to the single-dose administration of compound 2 (within 30 minutes) and at the following time points after administration:

30 (±10) minutes and 1, 2, 3, 4, 6, 8, and 10 hours (±10 minutes); and 24, 48, and 72 hours (±1 hour). After 72 hours of blood sample collection, subjects will begin oral daily dosing of compound 2 (i.e., C1D1). The PK/PD profile from Day −3 through Day 1 is optional (following Medical Monitor approval) for additional subjects enrolled in the dose escalation phase (i.e., for any subjects beyond the 3 initial subjects enrolled in a cohort) and for subjects enrolled in the expansion cohorts.

All subjects will undergo 10-hour PK/PD sampling on C2D1, C4D1 and C6D1.

For this profile, one blood sample will be drawn immediately prior to that day's first dose of compound 2 (i.e., dosing with compound 2 will occur at the clinical site); subsequent blood samples will be drawn at the following time points after dosing: 30 (±10) minutes, and 1, 2, 3, 4, 6, 8, and 10 hours (±10 minutes). Blood samples also will be drawn on Days 8, 15 and 22 of Cycle 1, Day 15 of Cycle 2, Days 1 and 15 of Cycle 3, and Day 1 of each cycle thereafter; all samples will be obtained prior to dosing (i.e., dosing with compound 2 will occur at the clinical site). Additionally, one blood sample will be drawn at the EOT Visit.

The timing of blood samples drawn for compound 2 concentration determination may be changed if the emerging data indicates that an alteration in the sampling scheme is needed to better characterize compound 2's PK profile.

Pharmacodynamic Assessments

Blood Samples

Serial blood samples will be drawn before and after dosing with compound 2 in order to determine circulating concentrations of 2-HG. Samples collected for PK assessments also will be used to assess 2-HG levels and metabolic profiles. In addition, subjects will have blood drawn for determination of 2-HG levels at the screening assessment.

The timing of blood samples drawn for 2-HG concentration determination may be changed if the emerging data indicate that an alteration in the sampling scheme is needed to better characterize the 2-HG response to compound 2 treatment.

Urine Samples

Subjects will have urine samples collected for determination of 2-HG levels at the screening assessment and prior to dosing on Day 15 of Cycle 1 and on Day 1 of Cycle 2 and Day 1 of each cycle thereafter. At least 20 mL of urine will be collected for each sample.

The volume of each collection will be measured and recorded and sent to a central laboratory for determination of urinary 2-HG concentration. An aliquot from each collection will be analyzed for urinary creatinine concentration.

Tumor and Skin Biopsy Samples

Tumor and skin biopsy specimens also will be assessed for 2-HG levels, metabolic profiling, and, if feasible, intratumoral compound 2 levels.

Evaluation of Cholesterol and 4β-OH-Cholesterol

Serial blood samples will be drawn to obtain plasma cholesterol and 4β-OH-cholesterol levels as a potential CYP3A4 induction marker. Samples collected for PK assessments also will be used to assess cholesterol and 4β-OH-cholesterol levels. Specifically, samples obtained on Day −3 predose (within 30 minutes), and at 24, 48, and 72 hours (±1 hour) will be assessed for cholesterol and 4β-OH-cholesterol levels as will predose samples on Days 8, 15 and 22 of Cycle 1, Days 1 and 15 of Cycles 2 and 3, and Day 1 of every cycle thereafter.

In addition, subjects will have blood drawn for determination of cholesterol and 4β-OH-cholesterol levels at the screening assessment.

Adverse Events

Monitoring of AEs will be conducted throughout the study. Adverse events and SAEs will be recorded in the eCRF from time of the signing informed consent through 28 days after the last study drug dose. In addition, SAEs that are assessed as possibly or probably related to study treatment that occur >28 days post-treatment also are to be reported. All AEs should be monitored until they are resolved or are clearly determined to be due to a subject's stable or chronic condition or intercurrent illness(es).

An adverse event (AE) is any untoward medical occurrence associated with the use of a drug in humans, whether or not considered drug related. An AE (also referred to as an adverse experience) can be any unfavorable and unintended sign (e.g., an abnormal laboratory finding), symptom, or disease temporally associated with the use of a drug, without any judgment about causality. An AE can arise from any use of the drug (e.g., off-label use, use in combination with another drug) and from any route of administration, formulation, or dose, including an overdose.

A suspected adverse reaction is any AE for which there is a reasonable possibility that the drug caused the AE. For the purposes of expedited safety reporting, 'reasonable possibility' means there is evidence to suggest a causal relationship between the drug and the AE.

An unexpected AE is one for which the nature or severity of the event is not consistent with the applicable product information, e.g., the Investigator's Brochure.

An AE or suspected adverse reaction is considered serious (SAE) if, in the view of either the Investigator or Sponsor, it results in any of the following outcomes:

Death.

Life-threatening. Life-threatening means that the subject was at immediate risk of death from the reaction as it occurred, i.e., it does not include a reaction which hypothetically might have caused death had it occurred in a more severe form.

In-patient hospitalization or prolongation of existing hospitalization. Hospitalization admissions and/or surgical operations scheduled to occur during the study period, but planned prior to study entry are not considered AEs if the illness or disease existed before the subject was enrolled in the study, provided that it did not deteriorate in an unexpected manner during the study (e.g., surgery performed earlier than planned).

A persistent or significant incapacity or substantial disruption of the ability to conduct normal life functions.

Congenital anomaly/birth defect.

Important medical event. An important medical event is an event that may not result in death, be life-threatening, or require hospitalization but may be considered an SAE when, based upon appropriate medical judgment, it may jeopardize the patient or subject and may require medical or surgical intervention to prevent one of the outcomes listed in the definitions for SAEs. Examples of such medical events include allergic bronchospasm requiring intensive treatment in an emergency room or at home, blood dyscrasias or convulsions that do not result in in-patient hospitalization, or the development of drug dependency or drug abuse.

Statistical Methods

Sample Size Estimation

Based on the planned dose escalation scheme, it is estimated that approximately 45 subjects will be enrolled in the study. This assumes that identification of the MTD requires the evaluation of 2 dose levels of compound 2 with only 3 subjects per dose level, with the exception of the MTD which required 6 subjects (n=9) with 12 subjects enrolled per cohort in the expansion phase (n=36). Additional subjects may be needed for cohort expansion during dose escalation, for the replacement of non-evaluable subjects, or for evaluation of alternative dosing regimens other than the planned escalation scheme or the MTD, to optimize the recommended Phase 2 dose.

Figure 41:
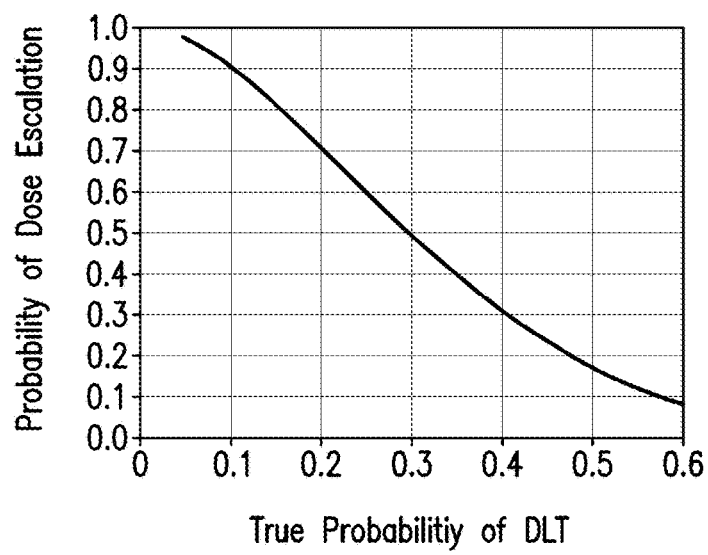
FIG. 41 is a graphical representation of the probability of escalation from a lower dose to the next higher dose, for a range of true rates of DLT, in the standard 3+3 dose-escalation design.

FIG. 41 presents the probability of escalation from a lower dose to the next higher dose, for a range of true rates of DLT, in the standard 3+3 dose-escalation design. For example, if the true DLT rate were 0.20 (20%), then the chance of dose escalation would be approximately 0.70 (70%).

To ensure that the toxicity at the MTD or other doses and regimens that may be used in further studies, up to 36 additional subjects will be accrued at the MTD. The estimation of toxicity rates will be based on 36 additional subjects and the 6 subjects previously dosed at the MTD; toxicity rates can be estimated with a maximum margin or error of ±13.4% (90% exact confidence interval) for n=42. The sample size of n=42 would allow the detection of at least one AE with a true incidence of 6.9% with 95% confidence. With a sample size of n=42 and with a true incidence of 6.9%, there is a 95% chance of observing at least one AE.

The following subject populations (i.e., analysis sets) will be evaluated and used for presentation of the data:

Intent-to-Treat (ITT) Analysis Set: All subjects who were enrolled and received at least one dose of study treatment. The ITT analysis set will be the primary set for the analysis of safety data.

Per-Protocol (PP) Analysis Set: All subjects in the ITT Analysis Set who had no major protocol violations. Results of the potential clinical activity of compound 2 will be primarily based on the PP analysis set.

No imputation will be performed for missing data elements.

When tabulating AE data, partial dates will be handled as follows. If the day of the month is missing, the onset day will be set to the first day of the month unless it is the same month and year as study treatment. In this case, in order to conservatively report the event as treatment emergent, the onset date will be assumed to be the date of treatment. If the onset day and month are both missing, the day and month will be assumed to be January 1, unless the event occurred in the same year as the study treatment. In this case, the event onset will be coded to the day of treatment in order to conservatively report the event as treatment emergent. A missing onset date will be coded as the day of treatment.

There will be no formal interim analyses of the data. Interim safety reviews will be conducted by the Clinical Study Team following completion of each dosing cohort prior to dose escalation and enrollment in the next cohort. Evaluation of PK and PD variables will also be conducted as needed to evaluate the potential relationship between levels of compound 2 and 2-HG levels.

Statistical analyses will be primarily descriptive in nature since the goal of the study is to determine the MTD of compound 2. This will be achieved by the results of a deterministic algorithm; thus, statistical hypothesis testing is neither intended for assessment of MTD.

Tabulations will be produced separately for the dose escalation and expansion phases of the study for appropriate disposition, demographic, baseline, safety, PK, PD, and clinical activity parameters. For the dose escalation phase, data will be summarized by dose level and overall, and for the expansion phase, by malignancy type and overall. Categorical variables will be summarized by frequency distributions (number and percentages of subjects) and continuous variables will be summarized by descriptive statistics (mean, standard deviation, median, minimum, and maximum).

All data will be provided in by-subject listings.

A tabulation of the disposition of subjects will be presented, including the number enrolled, the number treated, and the reasons for study discontinuation will be reported. Entry criteria and protocol deviations will be listed.

Demographic and baseline disease characteristic data summarization will be performed in order to descriptively assess the comparability of dose groups. Data to be tabulated will include sex, age, and race and ethnicity, as well as disease-specific information.

A summary of study drug exposure, including number of doses administered, total dose, duration of treatment, compliance, and the proportion of subjects with dose modifications will be produced.

Adverse events will be summarized by Medical Dictionary for Regulatory Activities (MedDRA) system organ class and preferred term. Separate tabulations will be produced for all treatment-emergent AEs (TEAEs), treatment-related AEs (those considered by the Investigator as at least possibly drug related), SAEs, discontinuations due to AEs, and AEs of at least Grade 3 severity. By-subject listings will be provided for deaths, SAEs, DLTs, and AEs leading to discontinuation of treatment.

Descriptive statistics will be provided for clinical laboratory, ECG interval, LVEF, and vital signs data, presented as both actual values and changes from baseline relative to each on-study evaluation and to the last evaluation on study.

Shift tables of laboratory data from baseline to worst value and from baseline to last value on treatment will be presented based on CTCAE v 4.03 grading. Shift tables also will be provided for ECOG PS from baseline to worst value, baseline to best, and baseline to last value on treatment.

Pharmacokinetic Analyses

Descriptive statistics (i.e., number of subjects, mean, standard deviation, geometric mean and coefficient of variation, median, minimum, and maximum) will be used to summarize PK parameters for each dose group and, where appropriate, for the entire population. Such parameters will include (but are not limited to) $C_{max}$, $T_{max}$, AUC, elimination half-life. The relationships between dose and both $C_{max}$ and AUC will be explored graphically for dose-proportionality.

Pharmacodynamic Analyses

The potential relationship between plasma levels of compound 2 and blood/plasma or urine 2-HG levels will be explored with descriptive and graphical methods.

Clinical Activity Analyses

Response to treatment as assessed by the site Investigator's using RECIST, modified RANO or revised IWG criteria will be tabulated. Two-sided 90% confidence intervals on the response rates will be calculated for each dose level and overall. Data will also be summarized by type of malignancy.

Descriptive statistics will be used to summarize Ki67 levels from tumor biopsies.

Details on evaluation of exploratory analyses, including evaluation of early clinical activity and possible relationships with PD biomarkers, will be described in the statistical analysis plan.

Example 4

5 mg and 10 mg dose strength tablets (free-base equivalent) may be prepared using a dry blend process described in Table A.

TABLE A

| Component | Weight Composition | 5 mg tablet* Amount per tablet (mg) | 10 mg tablet* Amount per tablet (mg) |
|---|---|---|---|
| Compound 2 | 6% | 6.0 | 12.0 |
| Microcrystalline Cellulose | 80% | 80.0 | 160.0 |
| Hydroxypropyl Cellulose | 2% | 2.0 | 4.0 |
| Sodium Starch Glycolate | 8% | 8.0 | 16.0 |
| Sodium Lauryl Sulfate | 1% | 1.0 | 2.0 |
| Hypromellose Acetate Succinate (Hydroxypropyl Methylcellulose Acetate Succinate) | 1% | 1.0 | 2.0 |
| Colloidal Silicon Dioxide | 1% | 1.0 | 2.0 |
| Magnesium Stearate | 1% | 1.0 | 2.0 |
| TOTAL | 100% | 100.0 | 200.0 |

*Free-base equivalent 50 mg and 200 mg dose strength tablets (free-base equivalent) may be prepared using a dry granulation process described in Table B

TABLE B

| | Component | Weight Composition | 50 mg tablet* Amount per tablet (mg) | 200 mg tablet* Amount per tablet (mg) |
|---|---|---|---|---|
| Intragranule | Compound 2 | 40% | 60.0 | 240.0 |
| | Microcrystalline Cellulose | 35% | 52.5 | 210.0 |
| | Hydroxypropyl Cellulose | 2% | 3.0 | 12.0 |
| | Sodium Starch Glycolate | 6% | 9.0 | 36.0 |
| | Sodium Lauryl Sulfate | 1% | 1.5 | 6.0 |
| | Hypromellose Acetate Succinate | 1% | 1.5 | 6.0 |
| | Colloidal Silicon Dioxide | 1.50% | 2.25 | 9.0 |
| | Magnesium Stearate | 0.75% | 1.125 | 4.5 |
| Extragranule | Microcrystalline Cellulose | 9.50% | 14.25 | 57.0 |
| | Sodium Starch Glycolate | 2% | 3.0 | 12.0 |
| | Colloidal Silicon Dioxide | 0.50% | 0.75 | 3.0 |
| | Magnesium Stearate | 0.75% | 1.125 | 4.5 |
| | TOTAL | 100% | 150.0 | 600.0 |

*Free-base equivalent 25 mg, 50 mg, 100 mg and 150 mg dose strength tablets (free-base equivalent) may be prepared using a dry granulation common blend as described in Table C.

TABLE C

| Component | Weight Composition | 100 mg tablet* Amount per tablet (mg) | 150 mg tablet* Amount per tablet (mg) |
|---|---|---|---|
| Compound 2 | 30% | 120.0 | 180.0 |
| Microcrystalline Cellulose | 45% | 180.0 | 270.0 |
| Hydroxypropyl Cellulose | 2% | 8.0 | 12.0 |
| Sodium Starch Glycolate | 6% | 24.0 | 36.0 |
| Sodium Lauryl Sulfate | 1% | 4.0 | 6.0 |
| Hypromellose Acetate Succinate | 1% | 4.0 | 6.0 |
| Colloidal Silicon Dioxide | 1.50% | 6.0 | 9.0 |
| Magnesium Stearate | 0.75% | 3.0 | 4.5 |
| Microcrystalline Cellulose | 9.50% | 38.0 | 57.0 |
| Sodium Starch Glycolate | 2% | 8.0 | 12.0 |
| Colloidal Silicon Dioxide | 0.50% | 2.0 | 3.0 |
| Magnesium Stearate | 0.75% | 3.0 | 4.5 |
| TOTAL | 100% | 400.0 | 600.0 |

*Free-base equivalent

While the foregoing invention has been described in some detail for purposes of clarity and understanding, these particular embodiments are to be considered as illustrative and not restrictive. It will be appreciated by one skilled in the art from a reading of this disclosure that various changes in form and detail can be made without departing from the true scope of the invention, which is to be defined by the appended claims rather than by the specific embodiments.

The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present disclosure, including definitions, will control.

The invention claimed is:

1. A method of treating a solid tumor characterized by the presence of a mutant allele of isocitrate dehydrogenase 2 (IDH2) comprising administering to a subject a therapeutically effective dose of a crystalline form of 2-methyl-1-[(4-[6-(trifluoromethyl)pyridin-2-yl]-6-{[2-(trifluoromethyl)pyridin-4-yl] amino}-1,3,5-triazin-2-yl)amino]propan-2-ol, wherein the crystalline form is selected from
  a) the crystalline form characterized by an X-ray powder diffraction pattern having peaks at 2θ angles of 6.8, 10.6, 13.6, 14.2, and 19.2°±0.2°, b) the crystalline form characterized by an X-ray powder diffraction pattern having peaks at 2θ angles of 8.9, 13.0, 18.9, 23.8, and 28.1°±0.2°, c) the crystalline form characterized by an X-ray powder diffraction pattern having peaks at 2θ angles of 12.7, 17.1, 19.2, 23.0, and 24.2°±0.2°, d) the crystalline form characterized by an X-ray powder diffraction pattern having peaks at 2θ angles of 7.2, 13.6, 18.5, 19.3, 21.9, and 23.5°±0.2°, e) the crystalline form characterized by an X-ray powder diffraction pattern having peaks at 2θ angles of 6.4, 8.4, 9.8, 17.8, and 19.7°±0.2°, and f) the crystalline form characterized by an X-ray powder diffraction pattern having peaks at 2θ angles of 8.1, 14.1, 16.4, 17.3, 20.5, and 24.1°±0.2°, wherein the therapeutically effective dose is from about 30 mg to about 300 mg.

2. The method of claim 1, wherein the crystalline form is selected from
   a) the crystalline form characterized by an X-ray powder diffraction pattern substantially similar to FIG. 1,
   b) the crystalline form characterized by an X-ray powder diffraction pattern substantially similar to FIG. 2,
   c) the crystalline form characterized by an X-ray powder diffraction pattern substantially similar to FIG. 34,
   d) the crystalline form characterized by an X-ray powder diffraction pattern substantially similar to FIG. 37,
   e) the crystalline form characterized by an X-ray powder diffraction pattern substantially similar to FIG. 38, and
   f) the crystalline form characterized by an X-ray powder diffraction pattern substantially similar to FIG. 39.

3. The method of claim 1, wherein the solid tumor is brain tumor, melanoma, chondrosarcoma, or cholangiocarcinoma.

4. The method of claim 3, wherein the brain tumor is glioma.

5. The method of claim 3, wherein the brain tumor is glioblastoma multiforme.

6. The method of claim 3, wherein the brain tumor is astrocytic tumor, oligodendroglial tumor, oligoastrocytic tumor, ependymoma, medulloblastoma; primitive neuroectodermal tumor, schwannoma, meningioma, meatypical meningioma, anaplastic meningioma; or pituitary adenoma.

7. The method of claim 1, wherein the crystalline form of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol is administered orally.

8. The method of claim 7, wherein the therapeutically effective dose is about 30 mg, or about 50 mg, or about 75 mg, or about 100 mg, or about 125 mg, or about 150 mg, or about 175 mg, or about 200 mg, or about 225 mg, or about 250 mg or about 275 mg, or about 300 mg.

9. A method of treating a solid tumor characterized by the presence of a mutant allele of isocitrate dehydrogenase 2 (IDH2) comprising administering to a subject a therapeutically effective dose of the crystalline form of 2-methyl-1-[(4-[6-(trifluoromethyl)pyridin-2-yl]-6-{[2-(trifluoromethyl)pyridin-4-yl]amino}-1,3,5-triazin-2-yl)amino]propan-2-ol methanesulfonate, wherein the crystalline form is selected from
   a) the crystalline form characterized by an X-ray powder diffraction pattern having peaks at 2θ angles of 7.5, 9.3, 14.5, 18.8, 21.3, and 24.8°±0.2°,
   b) the crystalline form characterized by an X-ray powder diffraction pattern having peaks at 2θ angles of 6.5, 19.0, 19.4, 19.9, and 24.7°±0.2°,
   c) the crystalline form characterized by an X-ray powder diffraction pattern having peaks at 2θ angles of 7.1, 14.5, 17.1, and 21.8°±0.2°,
   d) the crystalline form characterized by an X-ray powder diffraction pattern having peaks at 2θ angles of 6.3, 7.2, 8.1, 12.7, and 14.9°±0.2°,
   e) the crystalline form characterized by an X-ray powder diffraction pattern having peaks at 2θ angles of 14.1, 19.1, 21.8, 23.5, and 25.7°±0.2°,
   f) the crystalline form characterized by an X-ray powder diffraction pattern having peaks at 2θ angles of 9.0, 9.2, 21.9, 22.1, 24.2, and 24.6°±0.2°,
   g) the crystalline form characterized by an X-ray powder diffraction pattern having peaks at 2θ angles of 6.5, 19.6, 20.1, and 21.6°±0.2°,
   h) the crystalline form characterized by an X-ray powder diffraction pattern having peaks at 2θ angles of 6.7, 9.1, 10.8, 19.9, and 21.9°±0.2°,
   i) the crystalline form characterized by an X-ray powder diffraction pattern having peaks at 2θ angles of 6.3, 20.0, 20.2, 20.5, 21.2, and 26.5°±0.2°,
   j) the crystalline form characterized by an X-ray powder diffraction pattern having peaks at 2θ angles of 7.2, 7.4, 8.0, 8.2, 16.5, and 18.6°±0.2°,
   k) the crystalline form characterized by an X-ray powder diffraction pattern having peaks at 2θ angles of 6.3, 12.7, 20.3, 20.8, and 26.5°±0.2°,
   l) the crystalline form characterized by an X-ray powder diffraction pattern having peaks at 2θ angles of 6.6, 17.5, 20.8 and 23.3°±0.2°, and
   m) the crystalline form characterized by an X-ray powder diffraction pattern having peaks at 2θ angles of 6.4, 12.9, 20.2, and 26.1°±0.2°, wherein the therapeutically effective dose is from about 30 mg to about 300 mg.

10. The method of claim 9, wherein the crystalline form is selected from
   a) the crystalline form characterized by an X-ray powder diffraction pattern substantially similar to FIG. 5,
   b) the crystalline form characterized by an X-ray powder diffraction pattern substantially similar to FIG. 9,
   c) the crystalline form characterized by an X-ray powder diffraction pattern substantially similar to FIG. 11,
   d) the crystalline form characterized by an X-ray powder diffraction pattern substantially similar to FIG. 13,
   e) the crystalline form characterized by an X-ray powder diffraction pattern substantially similar to FIG. 15,
   f) the crystalline form characterized by an X-ray powder diffraction pattern substantially similar to FIG. 17,
   g) the crystalline form characterized by an X-ray powder diffraction pattern substantially similar to FIG. 19,
   h) the crystalline form characterized by an X-ray powder diffraction pattern substantially similar to FIG. 21,
   i) the crystalline form characterized by an X-ray powder diffraction pattern substantially similar to FIG. 23,
   j) the crystalline form characterized by an X-ray powder diffraction pattern substantially similar to FIG. 26,
   k) the crystalline form characterized by an X-ray powder diffraction pattern substantially similar to FIG. 28,
   l) the crystalline form characterized by an X-ray powder diffraction pattern substantially similar to FIG. 30, and
   m) the crystalline form characterized by an X-ray powder diffraction pattern substantially similar to FIG. 32.

11. The method of claim 9, wherein the solid tumor is brain tumor, melanoma, chondrosarcoma, or cholangiocarcinoma.

12. The method of claim 11, wherein the brain tumor is glioma.

13. The method of claim 11, wherein the brain tumor is glioblastoma multiforme.

14. The method of claim 11, wherein the brain tumor is astrocytic tumor, oligodendroglial tumor, oligoastrocytic tumor, ependymoma, medulloblastoma; primitive neuroectodermal tumor, schwannoma, meningioma, meatypical meningioma, anaplastic meningioma; or pituitary adenoma.

15. The method of claim 9, wherein the crystalline form of 2-methyl-1-[(4-[6-(trifluoromethyl)pyridin-2-yl]-6-{[2-(trifluoromethyl)pyridin-4-yl] amino}-1,3,5-triazin-2-yl) amino]propan-2-ol is administered orally.

16. The method of claim 15, wherein the therapeutically effective dose is about 30 mg, or about 50 mg, or about 75 mg, or about 100 mg, or about 125 mg, or about 150 mg, or about 175 mg, or about 200 mg, or about 225 mg, or about 250 mg or about 275 mg, or about 300 mg.

17. A method of treating angioimmunoblastic T-cell lymphoma (AITL) characterized by the presence of a mutant allele of isocitrate dehydrogenase 2 (IDH2) comprising administering to a subject a therapeutically effective dose of the crystalline form of 2-methyl-1-[(4-[6-(trifluoromethyl) pyridin-2-yl]-6-{[2-(trifluoromethyl)pyridin-4-yl] amino}-1,3,5-triazin-2-yl)amino]propan-2-ol, wherein the crystalline form is selected from
   a) the crystalline form characterized by an X-ray powder diffraction pattern having peaks at 2θ angles of 6.8, 10.6, 13.6, 14.2, and 19.2°±0.2°,
   b) the crystalline form characterized by an X-ray powder diffraction pattern having peaks at 2θ angles of 8.9, 13.0, 18.9, 23.8, and 28.1°±0.2°,
   c) the crystalline form characterized by an X-ray powder diffraction pattern having peaks at 2θ angles of 12.7, 17.1, 19.2, 23.0, and 24.2°±0.2°,
   d) the crystalline form characterized by an X-ray powder diffraction pattern having peaks at 2θ angles of 7.2, 13.6, 18.5, 19.3, 21.9, and 23.5°±0.2°,
   e) the crystalline form characterized by an X-ray powder diffraction pattern having peaks at 2θ angles of 6.4, 8.4, 9.8, 17.8, and 19.7°±0.2°, and
   f) the crystalline form characterized by an X-ray powder diffraction pattern having peaks at 2θ angles of 8.1, 14.1, 16.4, 17.3, 20.5, and 24.1°±0.2°,
wherein the therapeutically effective dose is from about 30 mg to about 300 mg.

18. The method of claim 17, wherein the crystalline form is selected from
   a) the crystalline form characterized by an X-ray powder diffraction pattern substantially similar to FIG. 1,
   b) the crystalline form characterized by an X-ray powder diffraction pattern substantially similar to FIG. 2,
   c) the crystalline form characterized by an X-ray powder diffraction pattern substantially similar to FIG. 34,
   d) the crystalline form characterized by an X-ray powder diffraction pattern substantially similar to FIG. 37,
   e) the crystalline form characterized by an X-ray powder diffraction pattern substantially similar to FIG. 38, and
   f) the crystalline form characterized by an X-ray powder diffraction pattern substantially similar to FIG. 39.

19. The method of claim 17, wherein the crystalline form of 2-methyl-1-[(4-[6-(trifluoromethyl)pyridin-2-yl]-6-{[2-(trifluoromethyl)pyridin-4-yl] amino}-1,3,5-triazin-2-yl) amino]propan-2-ol is administered orally.

20. The method of claim 19, wherein the therapeutically effective dose is about 30 mg, or about 50 mg, or about 75 mg, or about 100 mg, or about 125 mg, or about 150 mg, or about 175 mg, or about 200 mg, or about 225 mg, or about 250 mg or about 275 mg, or about 300 mg.

21. A method of treating angioimmunoblastic T-cell lymphoma (AITL) characterized by the presence of a mutant allele of isocitrate dehydrogenase 2 (IDH2) comprising administering to a subject a therapeutically effective dose of the crystalline form of 2-methyl-1-[(4-[6-(trifluoromethyl) pyridin-2-yl]-6-{[2-(trifluoromethyl)pyridin-4-yl] amino}-1,3,5-triazin-2-yl)amino]propan-2-ol methanesulfonate, wherein the crystalline form is selected from
   a) the crystalline form characterized by an X-ray powder diffraction pattern having peaks at 2θ angles of 7.5, 9.3, 14.5, 18.8, 21.3, and 24.8°±0.2°,
   b) the crystalline form characterized by an X-ray powder diffraction pattern having peaks at 2θ angles of 6.5, 19.0, 19.4, 19.9, and 24.7°±0.2°,
   c) the crystalline form characterized by an X-ray powder diffraction pattern having peaks at 2θ angles of 7.1, 14.5, 17.1, and 21.8°±0.2°,
   d) the crystalline form characterized by an X-ray powder diffraction pattern having peaks at 2θ angles of 6.3, 7.2, 8.1, 12.7, and 14.9°±0.2°,
   e) the crystalline form characterized by an X-ray powder diffraction pattern having peaks at 2θ angles of 14.1, 19.1, 21.8, 23.5, and 25.7°±0.2°,
   f) the crystalline form characterized by an X-ray powder diffraction pattern having peaks at 2θ angles of 9.0, 9.2, 21.9, 22.1, 24.2, and 24.6°±0.2°,
   g) the crystalline form characterized by an X-ray powder diffraction pattern having peaks at 2θ angles of 6.5, 19.6, 20.1, and 21.6°±0.2°,
   h) the crystalline form characterized by an X-ray powder diffraction pattern having peaks at 2θ angles of 6.7, 9.1, 10.8, 19.9, and 21.9°±0.2°,
   i) the crystalline form characterized by an X-ray powder diffraction pattern having peaks at 2θ angles of 6.3, 20.0, 20.2, 20.5, 21.2, and 26.5°±0.2°,
   j) the crystalline form characterized by an X-ray powder diffraction pattern having peaks at 2θ angles of 7.2, 7.4, 8.0, 8.2, 16.5, and 18.6°±0.2°,
   k) the crystalline form characterized by an X-ray powder diffraction pattern having peaks at 2θ angles of 6.3, 12.7, 20.3, 20.8, and 26.5°±0.2°,
   l) the crystalline form characterized by an X-ray powder diffraction pattern having peaks at 2θ angles of 6.6, 17.5, 20.8 and 23.3°±0.2°, and
   m) the crystalline form characterized by an X-ray powder diffraction pattern having peaks at 2θ angles of 6.4, 12.9, 20.2, and 26.1°±0.2°,
wherein the therapeutically effective dose is from about 30 mg to about 300 mg.

22. The method of claim 21, wherein the crystalline form is selected from
   a) the crystalline form characterized by an X-ray powder diffraction pattern substantially similar to FIG. 5,
   b) the crystalline form characterized by an X-ray powder diffraction pattern substantially similar to FIG. 9,
   c) the crystalline form characterized by an X-ray powder diffraction pattern substantially similar to FIG. 11,
   d) the crystalline form characterized by an X-ray powder diffraction pattern substantially similar to FIG. 13,
   e) the crystalline form characterized by an X-ray powder diffraction pattern substantially similar to FIG. 15,
   f) the crystalline form characterized by an X-ray powder diffraction pattern substantially similar to FIG. 17,
   g) the crystalline form characterized by an X-ray powder diffraction pattern substantially similar to FIG. 19, h) the crystalline form characterized by an X-ray powder diffraction pattern substantially similar to FIG. 21, i) the crystalline form characterized by an X-ray powder diffraction pattern substantially similar to FIG. 23, j) the crystalline form characterized by an X-ray powder diffraction pattern substantially similar to FIG. 26, k) the crystalline form characterized by an X-ray powder diffraction pattern substantially similar to FIG. 28, l) the crystalline form characterized by an X-ray powder diffraction pattern substantially similar to FIG. 30, and m) the crystalline form characterized by an X-ray powder diffraction pattern substantially similar to FIG. 32.

23. The method of claim 21, wherein the crystalline form of 2-methyl-1-[(4-[6-(trifluoromethyl)pyridin-2-yl]-6-{[2-(trifluoromethyl)pyridin-4-yl] amino}-1,3,5-triazin-2-yl) amino]propan-2-ol is administered orally.

24. The method of claim 23, wherein the therapeutically effective dose is about 30 mg, or about 50 mg, or about 75 mg, or about 100 mg, or about 125 mg, or about 150 mg, or about 175 mg, or about 200 mg, or about 225 mg, or about 250 mg or about 275 mg, or about 300 mg.

\* \* \* \* \*